US009889189B2

(12) United States Patent
Kang et al.

(10) Patent No.: US 9,889,189 B2
(45) Date of Patent: Feb. 13, 2018

(54) UNIVERSAL INFLUENZA VACCINE BASED ON HETEROLOGOUS MULTIPLE M2E PROTEINS

(71) Applicant: GEORGIA STATE UNIVERSITY RESEARCH FOUNDATION, Atlanta, GA (US)

(72) Inventors: Sang-Moo Kang, Lilburn, GA (US); Min-Chul Kim, Decatur, GA (US)

(73) Assignee: Georgia State University Research Foundation, Atlanta, GA (US)

( * ) Notice: Subject to any disclaimer, the term of this patent is extended or adjusted under 35 U.S.C. 154(b) by 131 days.

(21) Appl. No.: 14/440,114

(22) PCT Filed: Oct. 30, 2013

(86) PCT No.: PCT/US2013/067435
§ 371 (c)(1),
(2) Date: May 1, 2015

(87) PCT Pub. No.: WO2014/070848
PCT Pub. Date: May 8, 2014

(65) Prior Publication Data

US 2015/0273048 A1 Oct. 1, 2015

Related U.S. Application Data

(60) Provisional application No. 61/738,139, filed on Dec. 17, 2012, provisional application No. 61/722,602, filed on Nov. 5, 2012.

(51) Int. Cl.

| | |
|---|---|
| *A61K 39/12* | (2006.01) |
| *A61K 39/145* | (2006.01) |
| *C12N 7/00* | (2006.01) |
| *C07K 14/005* | (2006.01) |
| *A61K 39/00* | (2006.01) |

(52) U.S. Cl.
CPC ............ *A61K 39/145* (2013.01); *A61K 39/12* (2013.01); *C07K 14/005* (2013.01); *C12N 7/00* (2013.01); *A61K 2039/5254* (2013.01); *A61K 2039/5258* (2013.01); *A61K 2039/54* (2013.01); *A61K 2039/543* (2013.01); *A61K 2039/545* (2013.01); *A61K 2039/55516* (2013.01); *A61K 2039/58* (2013.01); *A61K 2039/6068* (2013.01); *A61K 2039/6075* (2013.01); *A61K 2039/70* (2013.01); *C07K 2319/00* (2013.01); *C07K 2319/40* (2013.01); *C12N 2760/16123* (2013.01); *C12N 2760/16134* (2013.01); *C12N 2799/026* (2013.01)

(58) Field of Classification Search
None
See application file for complete search history.

(56) References Cited

U.S. PATENT DOCUMENTS

| | | | | |
|---|---|---|---|---|
| 7,449,188 B2 * | 11/2008 | De Filette | C07K 14/005 | 424/192.1 |
| 8,420,102 B2 * | 4/2013 | Song | A61K 39/0258 | 424/192.1 |
| 9,101,578 B2 * | 8/2015 | Galarza | A61K 39/145 | |
| 2010/0143393 A1 | 6/2010 | Smith et al. | | |
| 2012/0052082 A1 * | 3/2012 | Compans | A61K 39/145 | 424/186.1 |
| 2014/0255441 A1 * | 9/2014 | Compans | C07K 14/195 | 424/186.1 |
| 2016/0220660 A1 * | 8/2016 | Song | A61K 39/0258 | |

FOREIGN PATENT DOCUMENTS

| | | |
|---|---|---|
| WO | 2006061723 A2 | 6/2006 |
| WO | 2006069262 A2 | 6/2006 |

OTHER PUBLICATIONS

International Search Report and Written Opinion for International Application No. PCT/US2013/067435 dated Jan. 29, 2014.
NCBI, GenBank Accession No. ADC45370 (Apr. 1, 2010).
Song, J.M. et al, "Influenza Virus-Like Particles Containing M2 Induce Broadly Cross Protective Immunity", PLoS One, 2011, vol. 6, Issue 1, Article Number e14538.
Song, J.M. et al, "Vaccination Inducing Broad and Improved Cross Protection against Multiple Subtypes of Influenza A Virus", PNAS, 2011, vol. 108, No. 2, pp. 757-761.
Shim, B.S. et al, "Sublingual Immunization with M2-Based Vaccine Induces Broad Protective Immunity against Influenza", PLos ONE, 2011, vol. 6, Issue 11, Article Number e27953.
Kim, et al., "Virus-like Particles Containing Multiple M2 Extracellular Domains Confer Improved Cross-protection Against Various Subtypes of Influenza Virus", Molecular Therapy, 2013, vol. 21, No. 2, pp. 485-492.
Viboud et al., "Preliminary Estimates of Mortality and Years of Life Lost Associated with the 2009 A/H1N1 Pandemic in the US and Comparison with Past Influenza Seasons", Version 1, PLoS Curr. 2010, RRN1153.
Osterholm, "Preparing for the Next Pandemic", N Engl J Med, 2005, 352, 1839-1842.
Fouchier, et al., "Characterization of a Novel Influenza A Virus Hemagglutinin Subtype (H16) Obtained from Black-Headed Gulls", Journal of Virology, 2005, vol. 79, No. 5, pp. 2814-2822.
Plotkin, et al., "Codon bias and frequency-dependent selection on the hemagglutinin epitopes of influenza A virus", PNAS, 2003, vol. 100, No. 12, pp. 7152-7157.

(Continued)

*Primary Examiner* — Agnieszka Boesen
(74) *Attorney, Agent, or Firm* — Thomas | Horstemeyer, LLC

(57) ABSTRACT

Disclosed are universal influenza A vaccines capable of providing broader crossprotection. The vaccine contains a fusion protein comprising tandem repeats of heterologous M2e epitope sequences that have been molecularly and genetically designed to provide broad cross-protection. The fusion protein may be incorporated into virus-like particles (VLPs) or a replicating live attenuated influenza virus vaccine, and administered alone or in combination with other influenza vaccines.

40 Claims, 20 Drawing Sheets

(56) References Cited

OTHER PUBLICATIONS

Liu, et al., "Sequence comparison between the extracellular domain of M2 protein human and avian influenza A virus provides new information for bivalent influenza vaccine design", Microbes and Infection, 2005, vol. 7, pp. 171-177.
Neirynck et al., "A Universal influenza A Vaccine based on the extracellular domain of the M2 protein", Nature Medicine, 1999, vol. 5, pp. 1157-1163.
Fan, et al., "Preclinical study of influenza virus A M2 peptide conjugate vaccines in mice, ferrets, and rhesus monkeys", Vaccine, 2004, vol. 22, pp. 2993-3003.
De Fillete, M, et al., "Improved design and intranasal delivery of an M2e-based human influenza A vaccine", Vaccine 2006, 24:6597-601.
Jegerlehner, et al., "Influenza A vaccine based on the extracellular domain of M2: weak protection mediated via antibody-dependent NK cell activity", J Immunol 2004, 172:5598-5605.
Ionescu et al., Pharmaceutical and immunological evaluation of human papillomavirus viruslike particle as an antigen carrier. J Pharm Sci 2006, 95:70-79.
Bessa, et al, "Efficient induction of mucosal and systemic immune responses by virus-like particles administered intranasally: implications for vaccine design", Eur J Immunol 2008, 38:114-126.
Tompkins, et al. "Matrix protein 2 vaccination and protection against influenza viruses, including subtype H5N1", Emerg Infect Dis 2007, 13:426-435.
Fu, et al., "Comparative immunogenicity evaluations of influenza A virus M2 peptide as recombinant virus like particle or conjugate vaccines in mice and monkeys", Vaccine 2009 27:1440-1447.
Wa, et al., "Protection against H1, H5, H6 and H9 influenza A infection with liposomal matrix 2 epitope vaccines", Vaccine 2006 24:5158-5168.
Eliasson, et al., "CTA1-M2e-DD: A novel mucosal adjuvant targeted influenza vaccine", Vaccine 2008 26: 1243-1252.
Huleatt, et al. "Potent immunogenicity and efficacy of a universal influenza vaccine candidate comprising a recombinant fusion protein linking influenza M2e to the TLR5 ligand flagellin", Vaccine 2008 26:201-214.
Turley, et al., "Safety and immunogenicity of a recombinant M2eflagellin influenza vaccine (STF2.4xM2e) in healthy adults", Vaccine 2011 29: 5145-5152.
Wu, et al., "The co-administration of CpG-ODN influenced protective activity of influenza M2e vaccine", Vaccine 2009 27:4320-4324.
Liu, et al., "High epitope density in a single recombinant protein molecule of the extracellular domain of influenza A viurs M2 protein significantly enhances protective immunity", Vaccine 2004 23:366-371.
De Filette, et al., "Universal influenza A vaccine: optimization of M2-based constructs", Virology 2005 337:149-161.
Heinen, et al., "Vaccination of pigs with a DNA construct expressing an influenza virus M2-nucleoprotein fusion protein exacerbates disease after challenge with influenza A virus", J Gen Virol 2002 83:1851-1859.
Fiers, et al., "A "universal" human influenza A vaccine", Virus Res 2004 103:173-176.
De Filette, et al., "The universal influenza vaccine M2e-HBc administered intranasally in combination with the adjuvant CTA1—DD provides complete protection", Vaccine 2006 24:544-551.
De Filette, et al., "An influenza A vaccine based on tetrameric ectodomain of matrix protein 2", J Biol Chem 2008 283:11382-11387.
Wang, et al., "Incorporation of high levels of chimeric human immunodeficiency virus envelope glycoproteins into virus-like particles", J Virol 2007 81:10869-10878.
Takada, et al., "Intranasal immunization with formali-inactivated virus vaccine induces a broad spectrum of heterosubtypic immunity against influenza A virus infection in mice", Vaccine 2003 21:3212-3218.
Tumpey, et al., "Mucosal delivery of inactivated influenza vaccine induces B-cell-dependent heterosubtypic crossprotection against lethal influenza A H5N1 virus infection", J Virol 2001 75: 5141-5150.
Sendl, et al., "Intranasal influenza vaccine in a working population", Clin Infect Dis 2004 38:974-980.
El Bakkouri, et al., "Universal vaccine based on ectodomain of matrix protein 2 of influenza A: Fc receptors and alveolar macrophages mediate protection", Journal of immunology 2011 186:1022-1031.
Song, et al., "Improved protection against avian influenza H5N1 virus by a single vaccination with virus-like particles in skin using microneedles", Antiviral Res 2010 88:244-247.
Quan, et al., "Induction of heterosubtypic immunity to influenza virus by intranasal immunization", J Virol 2008 82:1350-1359.
Wen, et al., "Mouse adaptation of the Asian influenza virus", The Journal of infectious diseases 1959 105:9-17.
Quan, et al., "Stabilization of influenza vaccine enhances protection by microneedle delivery in the mouse skin", PLoS One 2009 4:e7152.
Song, et al., "Protective immunity against H5N1 influenza virus by a single dose vaccination with virus-like particles", Virology 2010 405:165-175.
Andersson, et al., "Increased immunogenicity and protective efficacy of influenza M2e fused to a tetramerizing protein", PLoS One. 2012;7(10):e46395.
Extended European Search Report, issued in European application No. EP 13851144.9 dated Jun. 1, 2016.
Kim Min-Chul et al., "Multiple heterologous M2 extracellular domains presented on virus-like particles confer broader and stronger M2 immunity than live influenza A virus infection," Antiviral Research, vol. 99, No. 3, 2013, pp. 328-335.

* cited by examiner

LANE 1: TL-M2e5x VLP (250ng)

LANE 2: M2e5x VLP (250ng)

LANE 1: DUAL VECTOR-EXPRESSED M2e5x VLP (DUAL M2e5x INFECTION, 500ng)

LANE 2: MONOMERIC VECTOR-EXPRESSED M2e5x VLP (M2e5x CO-INFECTION, 1 ug)

SEQUENCE LISTING

```
<160> NUMBER OF SEQ ID NOS: 28

<210> SEQ ID NO 1
<211> LENGTH: 11
<212> TYPE: PRT
<213> ORGANISM: Artificial Sequence
<220> FEATURE:
<223> OTHER INFORMATION: Synthetic Construct

<400> SEQUENCE: 1

Pro Ile Arg Asn Glu Trp Gly Ser Arg Ser Asn
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Synthetic Construct

<400> SEQUENCE: 2

Pro Thr Arg Ser Glu Trp Glu Ser Arg Ser Ser
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is Asn, His, or Lys
<220> FEATURE:
<221> NAME/KEY: MISC_FEATURE
<222> LOCATION: (5)..(5)
<223> OTHER INFORMATION: Xaa is Glu or Gly

<400> SEQUENCE: 3

Pro Thr Arg Xaa Xaa Trp Glu Ser Arg Ser Ser
1               5                   10
```

```
<210> SEQ ID NO 4
<211> LENGTH: 11
<212> TYPE: PRT
<213> ORGANISM: Artificial Sequence
<220> FEATURE:
<223> OTHER INFORMATION: Synthetic Construct

<400> SEQUENCE: 4

Leu Thr Arg Asn Gly Trp Gly Cys Arg Cys Ser
1               5                   10

<210> SEQ ID NO 5
<211> LENGTH: 23
<212> TYPE: PRT
<213> ORGANISM: Artificial Sequence
<220> FEATURE:
<223> OTHER INFORMATION: Synthetic Construct

<400> SEQUENCE: 5

Ser Leu Leu Thr Glu Val Glu Thr Pro Ile Arg Asn Glu Trp Gly Ser
1               5                   10                  15

Arg Ser Asn Asp Ser Ser Asp
            20

<210> SEQ ID NO 6
<211> LENGTH: 23
<212> TYPE: PRT
<213> ORGANISM: Artificial Sequence
<220> FEATURE:
<223> OTHER INFORMATION: Synthetic Construct

<400> SEQUENCE: 6

Ser Leu Leu Thr Glu Val Glu Thr Pro Thr Arg Ser Glu Trp Glu Ser
1               5                   10                  15

Arg Ser Ser Asp Ser Ser Asp
            20

<210> SEQ ID NO 7
<211> LENGTH: 23
<212> TYPE: PRT
<213> ORGANISM: Artificial Sequence
<220> FEATURE:
<223> OTHER INFORMATION: Synthetic Construct

<400> SEQUENCE: 7

Ser Leu Leu Thr Glu Val Glu Thr Pro Thr Arg Asn Glu Trp Glu Ser
1               5                   10                  15

Arg Ser Ser Asp Ser Ser Asp
            20

<210> SEQ ID NO 8
<211> LENGTH: 23
<212> TYPE: PRT
<213> ORGANISM: Artificial Sequence
<220> FEATURE:
<223> OTHER INFORMATION: Synthetic Construct

<400> SEQUENCE: 8

Ser Leu Leu Thr Glu Val Glu Thr Pro Thr Arg Asn Gly Trp Glu Cys
1               5                   10                  15

Arg Cys Ser Asp Ser Ser Asp
            20

<210> SEQ ID NO 9
<211> LENGTH: 23
```

<212> TYPE: PRT
<213> ORGANISM: Artificial Sequence
<220> FEATURE:
<223> OTHER INFORMATION: Synthetic Construct

<400> SEQUENCE: 9

Ser Leu Leu Thr Glu Val Glu Thr Pro Thr Arg His Glu Trp Glu Cys
1               5                   10                  15

Arg Cys Ser Asp Ser Ser Asp
            20

<210> SEQ ID NO 10
<211> LENGTH: 23
<212> TYPE: PRT
<213> ORGANISM: Artificial Sequence
<220> FEATURE:
<223> OTHER INFORMATION: Synthetic Construct

<400> SEQUENCE: 10

Ser Leu Leu Thr Glu Val Glu Thr Pro Thr Arg Lys Glu Trp Glu Cys
1               5                   10                  15

Arg Cys Ser Asp Ser Ser Asp
            20

<210> SEQ ID NO 11
<211> LENGTH: 23
<212> TYPE: PRT
<213> ORGANISM: Artificial Sequence
<220> FEATURE:
<223> OTHER INFORMATION: Synthetic Construct

<400> SEQUENCE: 11

Ser Leu Leu Thr Glu Val Glu Thr Leu Thr Arg Asn Gly Trp Gly Cys
1               5                   10                  15

Arg Cys Ser Asp Ser Ser Asp
            20

<210> SEQ ID NO 12
<211> LENGTH: 27
<212> TYPE: PRT
<213> ORGANISM: Artificial Sequence
<220> FEATURE:
<223> OTHER INFORMATION: Synthetic Construct

<400> SEQUENCE: 12

Met Lys Phe Leu Val Asn Val Ala Leu Val Phe Met Val Val Tyr Ile
1               5                   10                  15

Ser Tyr Ile Tyr Ala Asp Pro Ile Asn Met Thr
            20                  25

<210> SEQ ID NO 13
<211> LENGTH: 33
<212> TYPE: PRT
<213> ORGANISM: Artificial Sequence
<220> FEATURE:
<223> OTHER INFORMATION: Synthetic Construct

<400> SEQUENCE: 13

Gly Gly Leu Lys Gln Ile Glu Asp Lys Leu Glu Glu Ile Leu Ser Lys
1               5                   10                  15

Leu Tyr His Ile Glu Asn Glu Leu Ala Arg Ile Lys Lys Leu Leu Gly
            20                  25                  30

Glu

<210> SEQ ID NO 14
<211> LENGTH: 37
<212> TYPE: PRT
<213> ORGANISM: Artificial Sequence
<220> FEATURE:
<223> OTHER INFORMATION: Synthetic Construct

<400> SEQUENCE: 14

```
Ile Leu Ala Ile Tyr Ser Thr Val Ala Ser Ser Leu Val Leu Leu Val
1               5                   10                  15

Ser Leu Gly Ala Ile Ser Phe Trp Met Cys Ser Asn Gly Ser Leu Gln
            20                  25                  30

Cys Arg Ile Cys Ile
        35
```

<210> SEQ ID NO 15
<211> LENGTH: 273
<212> TYPE: PRT
<213> ORGANISM: Artificial Sequence
<220> FEATURE:
<223> OTHER INFORMATION: Synthetic Construct

<400> SEQUENCE: 15

```
Thr Lys Cys Gln Thr Pro Leu Gly Ala Ile Asn Ser Ser Leu Pro Tyr
1               5                   10                  15

Gln Asn Ile His Pro Val Thr Ile Gly Glu Cys Pro Lys Tyr Val Arg
            20                  25                  30

Ser Ala Lys Leu Arg Met Val Thr Gly Leu Arg Asn Asn Pro Ser Ile
        35                  40                  45

Gln Ser Arg Gly Leu Phe Gly Ala Ile Ala Gly Phe Ile Glu Gly Gly
    50                  55                  60

Trp Thr Gly Met Ile Asp Gly Trp Tyr Gly Tyr His His Gln Asn Glu
65                  70                  75                  80

Gln Gly Ser Gly Tyr Ala Ala Asp Gln Lys Ser Thr Gln Asn Ala Ile
                85                  90                  95

Asn Gly Ile Thr Asn Lys Val Asn Thr Val Ile Glu Lys Met Asn Ile
            100                 105                 110

Gln Phe Thr Ala Val Gly Lys Glu Phe Asn Lys Leu Glu Lys Arg Met
        115                 120                 125

Glu Asn Leu Asn Lys Lys Val Asp Asp Gly Phe Leu Asp Ile Trp Thr
    130                 135                 140

Tyr Asn Ala Glu Leu Leu Val Leu Leu Glu Asn Glu Arg Thr Leu Asp
145                 150                 155                 160

Phe His Asp Ser Asn Val Lys Asn Leu Tyr Glu Lys Val Lys Ser Gln
                165                 170                 175

Leu Lys Asn Asn Ala Lys Glu Ile Gly Asn Gly Cys Phe Glu Phe Tyr
            180                 185                 190

His Lys Cys Asp Asn Glu Cys Met Glu Ser Val Arg Asn Gly Thr Tyr
        195                 200                 205

Asp Tyr Pro Lys Tyr Ser Glu Glu Ser Lys Leu Asn Arg Glu Lys Val
    210                 215                 220

Asp Gly Val Lys Leu Glu Ser Met Gly Ile Tyr Gln Ile Leu Ala Ile
225                 230                 235                 240

Tyr Ser Thr Val Ala Ser Ser Leu Val Leu Leu Val Ser Leu Gly Ala
                245                 250                 255

Ile Ser Phe Trp Met Cys Ser Asn Gly Ser Leu Gln Cys Arg Ile Cys
            260                 265                 270
```

Ile

<210> SEQ ID NO 16
<211> LENGTH: 248
<212> TYPE: PRT
<213> ORGANISM: Artificial Sequence
<220> FEATURE:
<223> OTHER INFORMATION: Synthetic Construct

<400> SEQUENCE: 16

```
Met Lys Phe Leu Val Asn Val Ala Leu Val Phe Met Val Val Tyr Ile
1               5                   10                  15

Ser Tyr Ile Tyr Ala Asp Pro Ile Asn Met Thr Thr Ser Val Asp Gly
            20                  25                  30

Thr Ser Leu Leu Thr Glu Val Glu Thr Pro Ile Arg Asn Glu Trp Gly
        35                  40                  45

Ser Arg Ser Asn Asp Ser Ser Asp Ala Ala Gly Gly Ala Ala Ser
    50                  55                  60

Leu Leu Thr Glu Val Glu Thr Pro Ile Arg Asn Glu Trp Gly Ser Arg
65                  70                  75                  80

Ser Asn Asp Ser Ser Asp Ala Ala Pro Gly Ala Ala Ser Leu Leu
                85                  90                  95

Thr Glu Val Glu Thr Pro Thr Arg Ser Glu Trp Glu Ser Arg Ser Ser
            100                 105                 110

Asp Ser Ser Asp Ala Ala Ala Gly Gly Ala Ala Ser Leu Leu Thr Glu
                115                 120                 125

Val Glu Thr Pro Thr Arg Asn Glu Trp Glu Ser Arg Ser Ser Asp Ser
    130                 135                 140

Ser Asp Ala Ala Ala Pro Gly Ala Ala Ser Leu Leu Thr Glu Val Glu
145                 150                 155                 160

Thr Leu Thr Arg Asn Gly Trp Gly Cys Arg Cys Ser Asp Ser Ser Asp
                165                 170                 175

Gly Gly Leu Lys Gln Ile Glu Asp Lys Leu Glu Glu Ile Leu Ser Lys
                180                 185                 190

Leu Tyr His Ile Glu Asn Glu Leu Ala Arg Ile Lys Lys Leu Leu Gly
            195                 200                 205

Glu Leu Glu Ile Leu Ala Ile Tyr Ser Thr Val Ala Ser Ser Leu Val
    210                 215                 220

Leu Leu Val Ser Leu Gly Ala Ile Ser Phe Trp Met Cys Ser Asn Gly
225                 230                 235                 240

Ser Leu Gln Cys Arg Ile Cys Ile
                245
```

<210> SEQ ID NO 17
<211> LENGTH: 20
<212> TYPE: PRT
<213> ORGANISM: Artificial Sequence
<220> FEATURE:
<223> OTHER INFORMATION: Synthetic Construct

<400> SEQUENCE: 17

```
Met Val Ser Ala Ile Val Leu Tyr Val Leu Leu Ala Ala Ala Ala His
1               5                   10                  15

Ser Ala Phe Ala
            20
```

<210> SEQ ID NO 18

```
<211> LENGTH: 20
<212> TYPE: PRT
<213> ORGANISM: Artificial Sequence
<220> FEATURE:
<223> OTHER INFORMATION: Synthetic Construct

<400> SEQUENCE: 18

Met Pro Leu Tyr Lys Leu Leu Asn Val Leu Trp Leu Val Ala Val Ser
1               5                   10                  15

Asn Ala Ile Pro
            20

<210> SEQ ID NO 19
<211> LENGTH: 37
<212> TYPE: PRT
<213> ORGANISM: Artificial Sequence
<220> FEATURE:
<223> OTHER INFORMATION: Synthetic Construct

<400> SEQUENCE: 19

Gln Met Asp Arg Val Val Lys Glu Met Arg Arg Gln Leu Glu Met Ile
1               5                   10                  15

Asp Lys Leu Thr Thr Arg Glu Ile Glu Gln Val Glu Leu Leu Lys Arg
            20                  25                  30

Ile Tyr Asp Lys Leu
        35

<210> SEQ ID NO 20
<211> LENGTH: 73
<212> TYPE: PRT
<213> ORGANISM: Artificial Sequence
<220> FEATURE:
<223> OTHER INFORMATION: Synthetic Construct

<400> SEQUENCE: 20

Leu Asn Pro Leu Asp Trp Thr Gln Tyr Phe Ile Phe Ile Gly Val Gly
1               5                   10                  15

Ala Leu Leu Leu Val Ile Val Leu Met Ile Phe Pro Ile Val Phe Gln
            20                  25                  30

Cys Leu Ala Lys Ser Leu Asp Gln Val Gln Ser Asp Leu Asn Val Leu
        35                  40                  45

Leu Leu Lys Lys Lys Gly Gly Asn Ala Ala Pro Ala Ala Glu Met
    50                  55                  60

Val Glu Leu Pro Arg Val Ser Tyr Thr
65                  70

<210> SEQ ID NO 21
<211> LENGTH: 30
<212> TYPE: PRT
<213> ORGANISM: Artificial Sequence
<220> FEATURE:
<223> OTHER INFORMATION: Synthetic Construct

<400> SEQUENCE: 21

Phe Met Phe Gly His Val Val Asn Phe Val Ile Ile Leu Ile Val Ile
1               5                   10                  15

Leu Phe Leu Tyr Cys Met Ile Arg Asn Arg Asn Arg Gln Tyr
            20                  25                  30

<210> SEQ ID NO 22
<211> LENGTH: 18
<212> TYPE: PRT
<213> ORGANISM: Artificial Sequence
```

<220> FEATURE:
<223> OTHER INFORMATION: Synthetic Construct

<400> SEQUENCE: 22

```
Ile Asn Asn Asn Leu Gln Arg Val Arg Glu Leu Ala Val Gln Ser Ala
1               5                   10                  15

Asn Ser
```

<210> SEQ ID NO 23
<211> LENGTH: 6
<212> TYPE: PRT
<213> ORGANISM: Artificial Sequence
<220> FEATURE:
<223> OTHER INFORMATION: Synthetic Construct

<400> SEQUENCE: 23

```
Ala Ala Pro Gly Ala Ala
1               5
```

<210> SEQ ID NO 24
<211> LENGTH: 273
<212> TYPE: PRT
<213> ORGANISM: Artificial Sequence
<220> FEATURE:
<223> OTHER INFORMATION: Synthetic Construct

<400> SEQUENCE: 24

```
Met Lys Phe Leu Val Asn Val Ala Leu Val Phe Met Val Val Tyr Ile
1               5                   10                  15

Ser Tyr Ile Tyr Ala Asp Pro Ile Asn Met Thr Thr Ser Ile Asn Asn
            20                  25                  30

Asn Leu Gln Arg Val Arg Glu Leu Ala Val Gln Ser Ala Asn Ser Ala
        35                  40                  45

Ala Ala Pro Gly Ala Ala Val Asp Gly Thr Ser Leu Leu Thr Glu Val
    50                  55                  60

Glu Thr Pro Thr Arg Asn Glu Trp Glu Ser Arg Ser Ser Asp Ser Ser
65                  70                  75                  80

Asp Ala Ala Ala Gly Gly Ala Ala Ser Leu Leu Thr Glu Val Glu Thr
                85                  90                  95

Pro Thr Arg Asn Glu Trp Glu Ser Arg Ser Ser Asp Ser Ser Asp Ala
            100                 105                 110

Ala Ala Pro Gly Ala Ala Ser Leu Leu Thr Glu Val Glu Thr Pro Thr
        115                 120                 125

Arg His Glu Trp Glu Ser Arg Ser Ser Asp Ser Ser Asp Ala Ala Ala
    130                 135                 140

Gly Gly Ala Ala Ser Leu Leu Thr Glu Val Glu Thr Pro Thr Arg His
145                 150                 155                 160

Glu Trp Glu Ser Arg Ser Ser Asp Ser Ser Asp Ala Ala Ala Pro Gly
                165                 170                 175

Ala Ala Ser Leu Leu Thr Glu Val Glu Thr Pro Thr Arg Asn Gly Trp
            180                 185                 190

Lys Cys Lys Cys Ser Asp Ser Ser Asp Gly Gly Leu Lys Gln Ile Glu
        195                 200                 205

Asp Lys Leu Glu Glu Ile Leu Ser Lys Leu Tyr His Ile Glu Asn Glu
    210                 215                 220

Leu Ala Arg Ile Lys Lys Leu Leu Gly Glu Leu Glu Ile Leu Ala Ile
225                 230                 235                 240

Tyr Ser Thr Val Ala Ser Ser Leu Val Leu Leu Val Ser Leu Gly Ala
```

|  |  |  | 245 |  |  |  | 250 |  |  |  | 255 |  |
| --- | --- | --- | --- | --- | --- | --- | --- | --- | --- | --- | --- | --- |
| Ile | Ser | Phe | Trp | Met | Cys | Ser | Asn | Gly | Ser | Leu | Gln | Cys | Arg | Ile | Cys |
|  |  |  | 260 |  |  |  | 265 |  |  |  | 270 |  |

Ile

<210> SEQ ID NO 25
<211> LENGTH: 819
<212> TYPE: DNA
<213> ORGANISM: Artificial Sequence
<220> FEATURE:
<223> OTHER INFORMATION: Synthetic Construct

<400> SEQUENCE: 25

| atgaagtttc tggtgaacgt tgccctggtt tttatggttg tttacatttc ctacatttac | 60 |
| --- | --- |
| gctgacccga ttaacatgac gactagtatt aacaataacc tgcagcgtgt ccgcgaactg | 120 |
| gccgtgcaaa gtgcaaattc cgcagcagca ccgggtgctg cagtcgacgg taccagcctg | 180 |
| ctgacggaag tcgaaacccc gacgcgtaac gaatgggaat ctcgcagctc tgatagttcc | 240 |
| gacgcagcag ctggcggtgc agccagtctg ctgaccgaag tggaaacccc gacgcgtaat | 300 |
| gaatgggaat cccgctcatc ggatagctct gacgcagctg caccgggtgc agcatcactg | 360 |
| ctgacggaag ttgaaacccc gacgcgtcat gaatgggaat cgcgcagttc cgattcatcg | 420 |
| gacgctgcag ccgcggtgc agccagcctg ctgaccgaag ttgaaacgcc gacccgtcat | 480 |
| gaatgggaaa gccgttctag cgacagttcc gatgccgcag caccgggtgc tgcgagcctg | 540 |
| ctgaccgaag tcgaaacgcc gacgcgtaat ggttggaaat gcaagtgtag cgattcatcg | 600 |
| gacggcggtc tgaaacagat tgaagataag ctggaagaaa tcctgagtaa actgtaccat | 660 |
| atcgaaaacg aactggcgcg catcaaaaag ctgctgggcg aactcgagat tctggccatc | 720 |
| tactcaaccg tggcgagctc tctggtgctg ctggtttcgc tgggtgcaat ctccttctgg | 780 |
| atgtgttcta acggttccct gcaatgtcgt atctgtatc | 819 |

<210> SEQ ID NO 26
<211> LENGTH: 771
<212> TYPE: DNA
<213> ORGANISM: Artificial Sequence
<220> FEATURE:
<223> OTHER INFORMATION: Synthetic Construct

<400> SEQUENCE: 26

| gccgccacca tgagtcttct aaccgaggtc gaaacgtacg ttctctctat catcccgtca | 60 |
| --- | --- |
| ggcccccctca aagccgagat cgcacagaga cttgaagatg tctttgcagg gaagaacacc | 120 |
| gatcttgagg ttctcatgga atggctaaag acaagaccaa tcctgtcacc tctgactaag | 180 |
| gggattttag gatttgtgtt cacgctcacc gtgcccagtg agcgaggact acagcgtaga | 240 |
| cgctttgtcc aaaatgccct taatgggaac ggcgatccaa taacatgga caaagcagtt | 300 |
| aaactgtata ggaagctcaa gagggagata acatttcatg gggccaaaga aatctcactc | 360 |
| agttattctg ctggtgcact tgccagttgt atgggcctca tatacaacag gatggggct | 420 |
| gtgaccactg aagtggcatt tggcctggta tgtgcaacct gtgaacagat tgctgactcc | 480 |
| cagcatcggt tcatagggca atggtgaca acaaccaacc cactaatcag acatgagaac | 540 |
| agaatggttt tagccagcac tacagctaag gctatggagc aaatggctgg atcgagtgag | 600 |
| caagcagcag aggctatgga ggttgctagt caggctaggc aaatggtgca agcgatgaga | 660 |
| accattggga ctcatcctag ctccagtgct ggtctgaaaa atgatcttct tgaaaatttg | 720 | caggcctatc agaaacgaat gggggtgcag atgcaacggt tcaagtgatg a    771

<210> SEQ ID NO 27
<211> LENGTH: 252
<212> TYPE: PRT
<213> ORGANISM: Artificial Sequence
<220> FEATURE:
<223> OTHER INFORMATION: Synthetic Construct

<400> SEQUENCE: 27

Met Ser Leu Leu Thr Glu Val Glu Thr Tyr Val Leu Ser Ile Ile Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Val Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Lys Ala
                85                  90                  95

Val Lys Leu Tyr Arg Lys Leu Lys Arg Glu Ile Thr Phe His Gly Ala
            100                 105                 110

Lys Glu Ile Ser Leu Ser Tyr Ser Ala Gly Ala Leu Ala Ser Cys Met
        115                 120                 125

Gly Leu Ile Tyr Asn Arg Met Gly Ala Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Gln
        195                 200                 205

Ala Arg Gln Met Val Gln Ala Met Arg Thr Ile Gly Thr His Pro Ser
    210                 215                 220

Ser Ser Ala Gly Leu Lys Asn Asp Leu Leu Glu Asn Leu Gln Ala Tyr
225                 230                 235                 240

Gln Lys Arg Met Gly Val Gln Met Gln Arg Phe Lys
                245                 250

<210> SEQ ID NO 28
<211> LENGTH: 17
<212> TYPE: PRT
<213> ORGANISM: Artificial Sequence
<220> FEATURE:
<223> OTHER INFORMATION: Synthetic Construct

<400> SEQUENCE: 28

Met Lys Ala Asn Leu Leu Val Leu Leu Cys Ala Leu Ala Ala Ala Asp
1               5                   10                  15

Ala

UNIVERSAL INFLUENZA VACCINE BASED ON HETEROLOGOUS MULTIPLE M2E PROTEINS

CROSS-REFERENCE TO RELATED APPLICATIONS

This application claims benefit of U.S. Provisional Application No. 61/722,602, filed Nov. 5, 2012, and of U.S. Provisional Application No. 61/738,139, filed Dec. 17, 2012, which are hereby incorporated herein by reference in their entirety.

STATEMENT REGARDING FEDERALLY SPONSORED RESEARCH OR DEVELOPMENT

This invention was made with Government Support under Grant No. AI093772 and Grant No. A1087782 awarded to Sang-Moo Kang by the National Institutes of Health. The Government has certain rights in the invention.

TECHNICAL FIELD

This application is generally in the field of influenza vaccines.

BACKGROUND

Influenza virus causes one of the most important respiratory viral diseases in humans, with significant medical and economic burdens. Approximately 10% to 20% of the world population is estimated to be infected during seasonal epidemics. Influenza virus causes 250,000-500,000 deaths worldwide annually; a global pandemic could kill millions (Osterholm, M. T. N Engl J Med. 2005 352:1839-1842; Viboud, C., et al. PLoS Curr 2010 RRN1153). In the US, influenza kills an average of 17,000-51,000 people in the United States (US) per year, causes an average of over 100,000 influenza-related hospitalizations and results in an economic cost of $12 billion per year (Thompson, W. W., et al. JAMA 2004 292:1333-1340).

Influenza is a lipid-enveloped virus with a segmented negative sense RNA genome, which belongs to the family Orthomyxoviridae. The envelope of the virion contains two types of surface glycoproteins, which play essential roles in viral infection. The hemagglutinin (HA) is responsible for attachment of the virus to sialic acid-containing receptors and viral entry by membrane fusion, whereas the neuraminidase (NA) is a receptor-destroying enzyme which plays important roles in viral release and cell-to-cell spread (Matrosovich, M. N., et al. J Virol 2004 78:12665-12667; Palese, P., et al. J Gen Virol 1976 33:159-163). There are 16 identified HA subtypes and 9 recognized NA subtypes. All of these subtype combinations have been isolated in birds. Currently circulating influenza viruses in human populations contain HA and NA combinations out of three different HA subtypes (H1, H2 and H3) and 2 different NA (N1 and N2) subtypes. However, there are often outbreaks of transmissions of avian host derived influenza viruses to human population from the poultry farms (Abdel-Ghafar, A. N., et al. N Engl J Med 2008 358:261-273).

Influenza viruses undergo changes over time, allowing them to evade the host immune system and to reduce the effectiveness of immunity to prior infections or vaccinations. Influenza A viruses can change by two different means: "antigenic drift" and "antigenic shift." Point mutations in the HA and/or NA antigens generate antigenically new influenza viruses with antigenic drift that occur during viral replication. The regular recurrence of influenza epidemics is thought to be caused by antigenic drift. Over some years sufficient changes accumulate in the virus to allow repeated infections of the host with antigenically different influenza viruses. These "major antigenic shifts" result in novel antigenic subtypes of the HA and/or NA glycoproteins that had not previously infected most of the human population, and therefore can spread rapidly causing global disease pandemics. Three global pandemics of influenza occurred during the 20$^{th}$ century, and were caused by H1N1 subtype viruses in 1918, H2N2 viruses in 1957, and H3N2 viruses in 1968. In addition to the circulating human influenza subtypes, other avian origin influenza viruses including H5N1, H7N2, H7N3, H7N7 and H9N2 subtypes have been shown to cause human infections on multiple occasions (Cheung, C. L., et al. J Infect Dis 2006 193:1626-1629; de Jong, M. D., et al. N Engl J Med 353:2667-2672 2005; Fouchier, R. A., et al. Proc Natl Acad Sci USA 2004 101:1356-1361; Le, Q. M., et al. Nature 2005 437:1108; Peiris, M., et al. Lancet 1999 354:916-917; Wong, S. S., et al. Chest 2006 129:156-168). The emergence or re-emergence of highly pathogenic avian influenza H5N1 viruses in domestic poultry and the increasing numbers of direct transmission of avian viruses to humans underscore a persistent threat to public health (Claas, E. C., et al. Vaccine 1998 16:977-978; Subbarao, K., et al. Science 1998 279: 393-396). Most recently, the 2009 outbreak of a new H1N1 virus illustrates how fast a new pandemic virus can spread in the human population once it acquires the ability to transmit among humans (Nava, G. M., et al. Euro Surveill 2009 14; Solovyov, A., et al. Euro Surveill 2009 14).

Inactivated influenza A and B virus vaccines have been extensively used in humans. The vaccines consist of purified virus that has been chemically inactivated with formalin or β-propiolactone, and in most vaccines the virus is also detergent-treated to produce soluble forms of the viral surface antigens. Influenza epidemics in human population contain two influenza A subtypes (H1N1 and H3N2) and one variant of influenza B virus, which become major components of being a trivalent current influenza vaccine. As an alternative approach to influenza immunization, live attenuated influenza virus (LAIV) vaccines administered by nasal spray (FluMist®) have been successfully developed. The vaccine is trivalent, containing influenza virus reassortants of the strains recommended for the current season. The currently used influenza vaccines induce immune responses to the viral surface glycoproteins HA and NA; although protective, the immunity is highly strain specific. Because these proteins undergo extensive antigenic variation, frequent changes are necessary in the vaccine composition. Although the current vaccines include proteins of the two currently circulating subtypes of influenza A viruses, they are not effective in protecting against the spectrum of different antigenic subtypes of influenza A viruses that are abundant in avian species which could potentially cause new influenza pandemics in humans.

Drifted strains that are not matched with the seasonal vaccine can appear following annual formulation of the vaccine composition, significantly compromising the vaccination efficacy. It has been suggested that approximately once every decade the mismatch between virus and vaccine is high enough to reduce vaccine effectiveness by 70%. The major limitations of the current vaccines include the need to produce new vaccines every season, the uncertainty in choice of the correct strains, long production times as well as the fact that the vaccines are produced by a slow process requiring embryonated eggs. Improved vaccines are needed, not only for seasonal influenza, but also for a potential influenza pandemic.

In contrast to HA, the influenza A M2 protein has a highly conserved extracellular domain of 23 amino acids (M2e). However, due to its small size and low immunogenicity, previous studies have focused on M2e peptide fusion constructs using a variety of carrier molecules: hepatitis B virus core (De Filette, M., et al. Vaccine 2006 24:544-551; Fan, J., et al. Vaccine 2004 22:2993-3003; Neirynck, S., et al. Nat Med 1999 5:1157-1163), human papillomavirus L protein (Ionescu, R. M., et al. J Pharm Sci 2006 95:70-79), keyhole limpet hemocyanin (Tompkins, S. M., et al. Emerg Infect Dis 2007 13:426-435), bacterial outer membrane complex (Fan, J., et al. Vaccine 2004 22:2993-3003; Fu, T. M., et al. Vaccine 2009 27:1440-1447), liposome (Ernst, W. A., et al. Vaccine 2006 24:5158-5168), and flagellin (Huleatt, J. W., et al. Vaccine 2008 26:201-214). M2 vaccines based on M2e fusion carriers or combinations of M2 expressing DNA and recombinant vectors were reported to provide cross protection against lethal infection with different strains (Ernst, W. A., et al. Vaccine 2006 24:5158-5168; Fan, J., et al. Vaccine 2004 22:2993-3003; Frace, A. M., et al. Vaccine 1999 17:2237-2244; Tompkins, S. M., et al. Emerg Infect Dis 2007 13:426-435). These studies suggested that M2e antibodies played an important role in providing protection. However, previous studies on M2e conjugate vaccines used potent adjuvants such as cholera toxins or heat labile endotoxins' derivatives, saponin QS21, Freund's adjuvants, or bacterial protein conjugates (De Filette, M., et al. Vaccine 2006 24:544-551; Eliasson, D. G., et al. Vaccine 2008 26:1243-1252; Fan, J., et al. Vaccine 2004 22:2993-3003; Fu, T. M., et al. Vaccine 2009 27:1440-1447; Huleatt, J. W., et al. Vaccine 2008 26:201-214; Mozdzanowska, K., et al. Virol J 2007 4:118). Such adjuvants that nonspecifically elicit host responses including inflammation and undesirable side effects are potentially adverse in developing a widely applicable prophylactic influenza vaccine. Moreover, the longevity and breadth of cross-protection mediated by M2 immunity remain unknown.

SUMMARY

Disclosed are universal influenza A vaccines capable of providing broad cross-protection in the absence of adjuvant. In particular, vaccine constructs have been molecularly designed and genetically engineered to comprise a fusion protein that contains three or more (e.g., 3, 4, 5, 6, 7, 8, 9, 10 or more) different influenza virus matrix protein 2 extracellular (M2e) domains (i.e., heterologous M2e domains). The fusion protein contains heterologous M2e domains to increase antigenicity and cross-protection. For example, the fusion protein can contain one or more M2e domains from a human influenza A subtype, one or more M2e domains from a swine influenza A subtype, and one or more M2e domains from an avian influenza A subtype.

The disclosed fusion protein may be displayed on the surface of a particle. For example, the fusion protein may be expressed in a membrane-anchored form and incorporated in virus-like particles (VLPs). Therefore, in some embodiments, the fusion protein further comprises a membrane anchor domain, such as a transmembrane domain and optional cytoplasmic domain of a viral envelope protein. For example, fusion proteins containing M2e domains with the transmembrane domain and cytoplasmic domain of influenza A hemagglutinin (HA) have been shown to incorporate into VLPs at a higher rate than wild type M2 protein. Alternatively, the fusion protein may be in a secreted form lacking a membrane anchor domain.

In some embodiments, the fusion protein is presented in a replicating live attenuated influenza virus vaccine. Therefore, a nucleic acid encoding the disclosed fusion protein can be inserted in the genome of a replicating live attenuated influenza virus. Thus, also disclosed is a recombinant virus comprising a nucleic acid encoding a fusion protein comprising heterologous M2e domains as disclosed herein. The fusion protein can further comprise a HA protein.

The fusion protein may also contain a signal peptide at the N-terminus to facilitate secretion. For example, the fusion protein may contain a mellitin signal peptide.

Influenza M2 is naturally a homotetramer. Therefore, in some embodiments, the fusion protein also contains an oligomer stabilization domain. For example, the fusion protein may contain a leucine zipper tetramerization motif, such as GCN4 to stabilize oligomers of the fusion proteins on the surface of a VLP.

The disclosed vaccines are highly effective in inducing M2e specific antibodies reactive to different influenza viruses, mucosal and systemic immune responses, and cross-protection regardless of influenza virus subtypes in the absence of adjuvant. In some embodiments, the vaccine is cross-protective against two or more (e.g., 2, 3, 4, 5, or 6) subtypes of influenza A with or without the use of an adjuvant. In addition, supplementing commercial human vaccines with the disclosed vaccine can significantly improve cross-protection.

Also disclosed are isolated polynucleotides encoding the disclosed fusion proteins and cells containing these polynucleotides. Also disclosed are methods of vaccinating a subject for influenza A by administering to a subject in need thereof a composition comprising the disclosed vaccine. The disclosed vaccine may be administered alone or in combination with one or more additional influenza vaccines.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A is a schematic showing the structure of M2e5x VLP and M2WT VLP. "SP"=mellitin signal peptide (Wang et al, 2007); "H"=Human influenza A type M2e; "S"=Swine influenza A type M2e; "A I"=Avian influenza A type I M2e; "A II"=Avian influenza A type II M2e; "TM-tail"=A/PR8 HA transmembrane and tail domains; "-"=linker; and "TM"=transmembrane. Although not shown, the M2e5x constructs can also contain a Toll-like receptor ligand (TL) sequence (TL-M2e5x; see FIG. 15B). FIG. 1B is a Western blot of influenza H3N2 virus, M2e5x and M2WT VLPs using mouse anti-M2 monoclonal antibody (14C2). Lane 1-3=influenza A/Philippines/2/82 (H3N2) virus (10 μg, 5 μg and 1 μg, respectively), Lane 4=TL-M2e5x VLP (100 ng), Lane 5=M2WT VLP (1 μg) and Lane 6=negative (VLPs without M2). "kD"=kilodalton. FIGS. 1C and 1D are graphs showing M2 reactivity to TL-M2e5x VLP (FIG. 1C) and M2WT VLP and influenza A/Philippines/2/82 (H3N2) virus (FIG. 1D) calculated by ELISA using M2 monoclonal antibody (Abcam 14C2). "OD"=optical density. FIG. 1E is a Western blot of TL-M2e5x recombinant protein produced using the Yeast expression system.

FIG. 2A shows peptide-specific ELISA wherein IgG antibodies specific to M2e were measured in boost immune sera using human, swine, avian I, or avian II type peptide as a coating antigen. FIGS. 2B and 2C are showing total IgG antibodies specific to the human type M2e peptide antigen after vaccination with to TL-M2e5x VLP (FIG. 2B) or M2WT VLP (FIG. 2C). FIG. 2D is a graph showing IgG isotype responses, wherein sera were serially diluted and ELISA was performed for serum antibodies specific to human type peptide. Error bars indicates mean±SEM.

FIGS. 3A and 3B are graphs showing TL-M2e5x VLP immunized sera (FIG. 3A) and M2WT VLP immunized sera (FIG. 3B). Sera were collected 3 weeks after prime boost vaccination. Serum was serially diluted and ELISA was performed. Error bars indicates mean±SEM. N=8 for all immunized groups.

FIGS. 5A and 5B are bar graphs showing levels of IgG (FIG. 5A) and IgA (FIG. 5B) determined by ELISA using human type M2e peptide as a coating antigen. FIG. 5C is a bar graph showing lung viral titers determined by an egg inoculation assay at day 5 after challenge. FIG. 5D is a bar graph showing IL-6 in BALF determined by a cytokine ELISA. Data represent mean±SEM. "BALF"=bronchoalveolar lavage fluid; "EID"=egg infectious dose; "IL"=interleukin; "IM"=intramuscular; "pg"=picogram.

FIGS. 6A to 6D are bar graphs showing IFN-γ secreting cells in splenocytes (N=6) (FIG. 6A), IL-4 secreting cells in splenocytes (N=6) (FIG. 6B), IFN-γ secreting cells in lung cells (FIG. 6C), and IL-4 secreting cells in lung cells (FIG. 6D). Splenocytes and lung cells were isolated from mice at day 5 post-challenge. Cytokine-producing cell spots were counted by ELISPOT reader. Data represent mean±SEM. "IFN"=interferon; "IL"=interleukin.

FIGS. 7A and 7B are graphs showing M2e peptide (FIG. 7A) and influenza virus-specific IgG antibody responses (FIG. 7B) in sera at 8 months after boost immunizations (N=4). FIGS. 7C and 7D are graphs showing body weight changes (FIG. 7C) and survival rates (FIG. 7D) after challenge with $4 \times LD_{50}$ of influenza A/Philippines/2/82 (H3N2) virus (N=4). Data represent mean±SEM.

FIGS. 8A-8D are graphs showing body weight (%) of mice (N=4) intranasally infected with $6 \times LD_{50}$ of influenza virus mixed with immune sera (TL-M2e5x or M2WT VLP) or naïve sera and monitored for 14 days. Immune sera collected from vaccinated mice at 3 weeks (FIGS. 8A-8B) and 8 months (FIGS. 8C-8D) after boost immunization were incubated with influenza viruses, A/PR/8/34(H1N1) (FIGS. 8A, 8C) and reassortant ANietnam/1203/2004 (H5N1) (FIGS. 8B, 8D).

FIG. 9 shows that supplementing TL-M2e5x VLP vaccines increased M2e immunity of human influenza vaccines.

FIG. 10 shows that supplementing TL-M2e5x VLP vaccines enhanced cross protective efficacy of commercial human 2009 pandemic influenza vaccine.

FIG. 11 shows that human vaccine (2009 pandemic vaccine) supplemented with TL-M2e5x VLPs conferred long-term (12 months) cross protection.

FIG. 12 shows that skin vaccination of commercial human vaccine (2009 pandemic virus) supplemented with TL-M2e5x VLPs conferred enhanced cross protection.

FIG. 13 shows that microneedle skin vaccination with TL-M2e5x VLP vaccine induced comparable or better cross protection compared to conventional intramuscular injection.

FIG. 14 shows that TL-M2e5x VLP vaccine provides enhanced cross protection in the presence of 2009 pandemic virus pre-existing immunity.

DETAILED DESCRIPTION

Figure 1A:
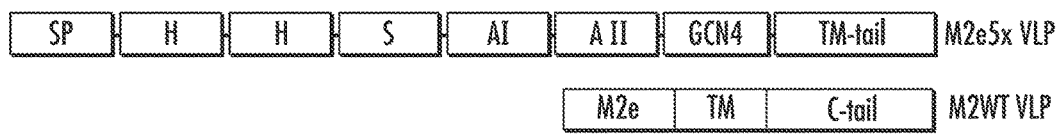
FIGS. 1A to 1E show characterization of tandem repeat M2e5x and M2WT virus like particles (VLPs).

Due to limitations of current vaccines in inducing cross protection against antigenically different influenza viruses, a universal vaccine that is based on the relatively conserved domains of the influenza virus is disclosed. The extracellular domain of the influenza M2 protein (M2e) remains nearly invariant among different strains (Liu, W., et al. Microbes Infect 2005 7:171-177), suggesting that M2 would be a promising candidate antigen for developing universal influenza vaccines. Previous studies have focused on influenza A vaccines based on the small extracellular domain of M2 (M2e), attempting to develop universal vaccines. Due to poor immunogenicity of M2e, chemical or genetic conjugates of M2e to carrier vehicles were most often used and protective efficacies were determined using a mouse model. However, severe weight loss and incomplete protection were reported even with using potent adjuvants (Andersson, A. M., et al. PloS one 2012 7:e46395; De Filette, M., et al. Vaccine 2006; De Filette, M., et al. J Biol Chem 283:11382-11387 2008; Eliasson, D. G., et al. Vaccine 2008 26:1243-1252; Ernst, W. A., et al. Vaccine 2006 24:5158-5168; Fan, J., et al. Vaccine 2004 22:2993-3003; Jegerlehner, A., et al. J Immunol 2004 172:5598-5605; Tompkins, S. M., et al. Emerg Infect Dis 2007 13:426-435; Wu, F., et al. Vaccine 2009 27:4320-4324). In the virion, M2 immunogenicity is low because it is a small protein potentially masked by the major surface glycoproteins, and because it is presented in low amounts. Disclosed are molecular design and genetic engineering techniques that overcome challenging difficulties of low immunogenicity of M2e as a universal vaccine.

Definitions

It must be noted that as used herein and in the appended claims, the singular forms "a," "an," and "the" include plural referents unless the context clearly dictates otherwise. Thus, for example, reference to "a peptide" includes a plurality of such peptides, reference to "the peptide" is a reference to one or more peptides and equivalents thereof known to those skilled in the art, and so forth.

In this specification and in the claims that follow, reference will be made to a number of terms that shall be defined to have the following meanings:

"Optional" or "optionally" means that the subsequently described event or circumstance can or cannot occur, and that the description includes instances where the event or circumstance occurs and instances where it does not. For example, the phrase "optionally a signal peptide" means that the signal peptide may or may not be included.

The term "universal influenza A vaccine" refers to vaccine capable of providing cross-protection against at least two, including three, four, five or more, subtypes of influenza A.

The term "individual," "host," "subject," and "patient" are used interchangeably to refer to any individual who is the target of administration, treatment, or vaccination. The subject can be a vertebrate, for example, a mammal. Thus, the subject can be a human or veterinary patient.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The terms "peptide," "protein," and "polypeptide" are used interchangeably to refer to a natural or synthetic molecule comprising two or more amino acids linked by the carboxyl group of one amino acid to the alpha amino group of another.

The term "protein domain" refers to a portion of a protein, portions of a protein, or an entire protein showing structural integrity; this determination may be based on amino acid composition of a portion of a protein, portions of a protein, or the entire protein.

The term "nucleic acid" refers to a natural or synthetic molecule comprising a single nucleotide or two or more nucleotides linked by a phosphate group at the 3' position of one nucleotide to the 5' end of another nucleotide. The nucleic acid is not limited by length, and thus the nucleic acid can include deoxyribonucleic acid (DNA) or ribonucleic acid (RNA).

The term "variant" refers to an amino acid sequence having conservative amino acid substitutions, non-conservative amino acid substitutions (i.e. a degenerate variant), or a peptide having 60%, 65%, 70%, 71%, 72%, 73%, 74%, 75%, 76%, 77%, 78%, 79%, 80%, 81%, 82%$, 83%, 84%, 85%, 86%, 87%, 88%, 89%, 90%, 91%, 92%, 93%, 94%, 95%, 96%, 97%, 98%, or 99% sequence identity to the recited sequence.

The term "percent (%) sequence identity" or "homology" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods. For purposes herein, the % sequence identity of a given nucleotides or amino acids sequence C to, with, or against a given nucleic acid sequence D (which can alternatively be phrased as a given sequence C that has or comprises a certain % sequence identity to, with, or against a given sequence D) is calculated as follows:

100 times the fraction W/Z, where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

A "fusion protein" refers to a polypeptide formed by the joining of two or more polypeptides through a peptide bond formed between the amino terminus of one polypeptide and the carboxyl terminus of another polypeptide. The fusion protein can be formed by the chemical coupling of the constituent polypeptides or it can be expressed as a single polypeptide from nucleic acid sequence encoding the single contiguous fusion protein. A single chain fusion protein is a fusion protein having a single contiguous polypeptide backbone. Fusion proteins can be prepared using conventional techniques in molecular biology to join the two genes in frame into a single nucleic acid, and then expressing the nucleic acid in an appropriate host cell under conditions in which the fusion protein is produced.

A "spacer" as used herein refers to a peptide that joins the proteins of a fusion protein. Generally a spacer has no specific biological activity other than to join the proteins or to preserve some minimum distance or other spatial relationship between them. However, the constituent amino acids of a spacer may be selected to influence some property of the molecule, such as the folding, net charge, or hydrophobicity of the molecule.

M2e Constructs

The disclosed vaccine contains heterologous M2 ectodomain (M2e) epitope sequences molecularly designed to cover a broad range of antigenically different subtypes of infleunza viruses. For example, the M2e epitope sequences can be derived from human, swine, avian host species, or any combination thereof.

Therefore, in some embodiments, the disclosed vaccine comprises a fusion protein containing heterologous M2 ectodomain (M2e) epitope sequences from different influenza types. For example, the fusion protein can contain at least 2, 3, 4, 5, 6, 7, 8, 9, 10, or more different M2e peptides from 2, 3, 4 or more influenza types. For example, the fusion protein can comprise at least five or at least ten heterologous M2e domains. In some embodiments, the fusion protein contains M2e peptides from human, swine, and avian (e.g., H5, H7, H9, or any combination thereof) influenza subtypes. As an example, the fusion protein can contain the following five influenza A virus subtype M2e sequences: 2× Human, 1× Swine, 1× Avian Type I, and 1× Avian Type II (FIG. 1).

In some embodiments, the human M2e sequence comprises the amino acid sequence PIRNEWGSRSN (SEQ ID NO:1), or a conservative variant thereof having at least about 70%, 80%, or 90% sequence identity to SEQ ID NO:1 (i.e., one, two, or three conservative amino acid substitutions). For example, human M2e isolates H1N1 (A/PR8, A/NC/99) and H3N2 (A/Phil/82) have the amino acid sequence SLLTEVET PIRNEWGSRSN DSSD (SEQ ID NO:5).

In some embodiments, amino acids that are conserved across species are maintained, e.g., Arg at position three and nine, Trp at position six, and Cys at position eight of SEQ ID NO:1. In other embodiments, conserved residues are conservatively substituted, e.g., Arg to Lys. In some embodiments, amino acids that are unique to a given species are conserved to increase heterogeneity and cross-protection, e.g., Ile at position two and Asp at position eleven of SEQ ID NO:1. Candidate sequence variants containing conserved substitutions may be tested using antibodies against the reference protein. In some embodiments, immune sera against M2e may be tested against the M2e variants for the cross-reactivity.

In some embodiments, the swine M2e sequence comprises the amino acid sequence PTRSEWESRSS (SEQ ID NO:2), or a conservative variant thereof having at least 70%, 80%, or 90% sequence identity to SEQ ID NO:2. For example, swine M2e isolates from the 2009 H1N1 pandemic (A/California/4/2009) have the amino acid sequence SLLTEVET PTRSEWESRSS DSSD (SEQ ID NO:6).

In some embodiments, the avian M2e sequence (referred to herein as "avian type I") comprises the amino acid sequence PTRX$_1$X$_2$WESRSS (SEQ ID NO:3), wherein X$_1$ is N, H, or K, wherein X$_2$ is E or G, or a conservative variant thereof having at least 70%, 80%, or 90% sequence identity to SEQ ID NO:3. For example, avian type I M2e isolates from H5N1 (A/Vietnam/1203/04, A/Indonesia/05, A/mandarin/kr/2010, A/ck/kr/2006) have the amino acid sequence SLLTEVET PTRNEWESRSS DSSD (SEQ ID NO:7). Avian type I M2e isolates from H7N3 (A/dk/Kr/2007), H9N2 (A/ck/Kr/2012) have the amino acid sequence SLLTEVET PTRNGWECRCS DSSD (SEQ ID NO:8). Avian type I M2e isolates from H5N1 (A/ck/Kr/Gimje/2008) have the amino acid sequence SLLTEVET PTRHEWECRCS DSSD (SEQ ID NO:9). Avian type I M2e isolates from H5N1 (A/ck/Vietnam/2011) have the amino acid sequence SLLTEVET PTRKEWECRCS DSSD (SEQ ID NO:10).

In some embodiments, the avian M2e sequence (referred to herein as "avian type II") comprises the amino acid sequence LTRNGWGCRCS (SEQ ID NO:4), or a conservative variant thereof having at least 70%, 80%, or 90% sequence identity to SEQ ID NO:4. For example, avian type II M2e isolates from H5N1 (A/HK/156/97), H9N2 (A/HK/1073/99) have the amino acid sequence SLLTEVET LTRNGWGCRCS DSSD (SEQ ID NO:11).

To increase heterogeneity, the fusion protein can contain at least one avian type I M2e domain comprising the amino acid sequence SEQ ID NO:3 or an amino acid sequence having at least 70%, 80%, or 90% sequence identity to SEQ ID NO:3, and at least one avian type II M2e domain comprising the amino acid sequence SEQ ID NO:4 or an amino acid sequence having at least 70%, 80%, or 90% sequence identity to SEQ ID NO:4.

The fusion protein may further comprise a signal peptide at the N-terminus to facilitate secretion. For example, the fusion protein may contain a mellitin signal peptide. In some embodiments, the melittin signal peptide has the amino acid sequence MKFLVNVALVFMVVYISYIYADPINMT (SEQ ID NO:12), or a conservative variant thereof having at least 72%, 76%, 80%, 84%, 88%, 92%, or 96% sequence identity to SEQ ID NO:12. Alternatively, the fusion protein may contain a baculovirus gp64 signal peptide (MVSAIVLYV-LLAAAAHSAFA, SEQ ID NO:17) or a chitinase signal peptide (MPLYKLLNVLWLVAVSNAIP, SEQ ID NO:18) (Wang, B., et al. J Virol 2007 81: 10869-10878), or a conservative variant thereof having at least 70%, 75%, 80%, 85%, 90%, or 95% sequence identity to SEQ ID NO:17 or SEQ ID NO:18.

Influenza M2 is naturally a homotetramer. Therefore, in some embodiments, the fusion protein also contains an oligomer stabilization domain. In some embodiments, the disclosed vaccine contains a tetramer stabilizing domain called GCN4 (leucine zipper tetramerization motif) (De Filette, M., et al. J Biol Chem 2008 283:11382-11387). For example, the GCN4 domain can have the amino acid sequence GGLKQIEDKLEEILSKLYHIENELARIK-KLLGE (SEQ ID NO:13), or a conservative variant thereof having at least 70%, 73%, 76%, 79%, 82%, 85%, 88%, 91%, 94%, or 97% sequence identity to SEQ ID NO:13. In some embodiments, the disclosed vaccine contains a NSP498-135 fragment of rotavirus (QMDRVVKEMRRQLEMIDKLT-TREIEQVELLKRIYDKL, SEQ ID NO:19) (Andersson, A. M., K. O. Hakansson, et al. (2012). PLoS One 7(10): e46395.), or a conservative variant thereof having at least 70%, 73%, 76%, 79%, 82%, 85%, 88%, 91%, 94%, or 97% sequence identity to SEQ ID NO:19, as the parallel tetrameric coiled-coil stabilizing domain.

To anchor multiple copies of heterologous tandem repeat M2e on the surface of a particle, the fusion protein may be expressed in a membrane-anchored form and incorporated in virus-like particles (VLPs). Therefore, in some embodiments, the fusion protein further comprises a membrane anchor domain, such as a transmembrane domain and optional cytoplasmic domain of a viral envelope protein. For example, fusion proteins containing M2e domains with the transmembrane domain and cytoplasmic domain of influenza A hemagglutinin (HA) have been shown to incorporate into VLPs at a higher rate than wild type M2 protein. In some embodiments, the membrane anchor domain comprises the full HA protein sequence. The transmembrane-cytoplasmic domain from hemaglutinin of A/PR/8/34 virus can have the amino acid sequence ILAIYSTVASSLVLL-VSLGAISFWMCSNGSLQCRICI (SEQ ID NO:14), or a conservative variant thereof having at least 76%, 79%, 82%, 85%, 88%, 91%, 94%, or 97% sequence identity to SEQ ID NO:14. The disclosed fusion protein may also comprise a HA stalk domain. The HA stalk domain can have the following amino acid sequence TKCQTPLGAINSSLPY-QNIHPVTIGECPKYVRSAKLRMVTGLRNNPSIQSR-GLFGAIAGFI EGGWTGMIDGWYGYHHQNEQGSG-YAADQKSTQNAINGITNKVNTVIEKMNIQFTAVG KEFNKLEKRMENLNKKVDDGFLDIWTYNAELLVL-LENERTLDFHDSNVKNLYEKVKS QLKNNA-KEIGNGCFEFYHKCDNECMESVRNGTYDYPKY-SEESKLNREKVDGVKLESM GIYQILAIYSTVASSLVLLVSLGAISFWMCSNG-SLQCRICI (SEQ ID NO:15), or a conservative variant thereof having at least 70%, 71%, 72%, 73%, 74%, 75%, 76%, 77%, 78%, 79%, 80%, 81%, 82%$, 83%, 84%, 85%, 86%, 87%, 88%, 89%, 90%, 91%, 92%, 93%, 94%, 95%, 96%, 97%, 98%, or 99% sequence identity to SEQ ID NO:15. Alternatively, the fusion protein may be in a secreted form lacking a membrane anchor domain. The membrane anchor domain can also comprise the mouse mammary tumor virus (MMTV) envelope glycoprotein (LNPLD-WTQYFIFIGVGALLLVIVLMIFPIVFQCLAK-SLDQVQSDLNVLLLKKKKGGNAA PAAEMVELPRV-SYT, SEQ ID NO:20), baculovirus glycoprotein gp64 FMFGHVVNFVIILIVILFLYCMI RNRNRQY, SEQ ID NO:21) (Wang, B., et al. J Virol 2007 81: 10869-10878), or a conservative variant thereof having at least 70%, 71%, 72%, 73%, 74%, 75%, 76%, 77%, 78%, 79%, 80%, 81%, 82%$, 83%, 84%, 85%, 86%, 87%, 88%, 89%, 90%, 91%, 92%, 93%, 94%, 95%, 96%, 97%, 98%, or 99% sequence identity to SEQ ID NO:20 or SEQ ID NO:21.

The fusion protein can comprise an amino acid sequence having a formula selected from the group consisting of:

$X_1$-([hM2e]$_n$-[sM2e]$_n$-[aM2e]$_n$)$_n$-$X_2$-$X_3$, $X_1$-([hM2e]$_n$-[aM2e]$_n$-[sM2e]$_n$)$_n$-$X_2$-$X_3$, $X_1$-([sM2e]$_n$-[hM2e]$_n$-[aM2e]$_n$)$_n$-$X_2$-$X_3$, $X_1$-([sM2e]$_n$-[aM2e]$_n$-[hM2e]$_n$)$_n$-$X_2$-$X_3$, $X_1$-([aM2e]$_n$-[sM2e]$_n$-[hM2e]$_n$)$_n$-$X_2$-$X_3$, and $X_1$-([aM2e]$_n$-[hM2e]$_n$-[sM2e]$_n$)$_n$-$X_2$-$X_3$;

wherein "$X_1$" consists of nothing or a signal peptide,
wherein "hM2e" consists of a human M2e domain,
wherein "sM2e" consists of a swine M2e domain,
wherein "aM2e" consists of an avian M2e domain,
wherein "$X_2$" consists of nothing or an oligomer stabilization domain,
wherein "$X_3$" consists of nothing or a membrane anchor domain,
wherein each "n" is independently an integer from one to five (e.g., 1, 2, 3, 4, or 5), and
wherein "-" consists of a peptide linker or a peptide bond.

In some embodiments, the fusion protein comprises an amino acid sequence having the following formula:

$$X_1\text{-}(hM2e\text{-}hM2e\text{-}sM2e\text{-}aM2e\text{-}aM2e)_n\text{-}X_2\text{-}X_3.$$

In a particular embodiment, the disclosed vaccine comprises the amino acid sequence: MKFLVNVALVFMVVYI-SYIYADPINMTTSVDGTSLLTEVETPIRNEWG-SRSNDSSDAAA GGAASLLTEVETPIRNEWGSRSNDSSDAAAP-GAASLLTEVETPTRSEWESRSSDSSDAAA GGAASLLTEVETPTRNEWESRSSDSSDAAAP-GAASLLTEVETLTRNGWGCRCSDSSDGG LKQIED-KLEEILSKLYHIENELARIKKLLGELEILAIYSTVASS-LVLLVSLGAISFWMCSNG SLQCRICI (M2e5x, SEQ ID NO:16), or a conservative variant thereof having at least 70%, 71%, 72%, 73%, 74%, 75%, 76%, 77%, 78%, 79%, 80%, 81%, 82%$, 83%, 84%, 85%, 86%, 87%, 88%, 89%, 90%, 91%, 92%, 93%, 94%, 95%, 96%, 97%, 98%, or 99% sequence identity to SEQ ID NO:16.

In some embodiments, the disclosed vaccine comprises a Toll-like receptor ligand (TL) sequence. For example, the disclosed vaccine can contain the TL sequence INNN-LQRVRELAVQSANS (SEQ ID NO:22). The vaccine can also contain one or more linkers. Therefore, in some embodiments, the disclosed vaccine comprises the amino acid sequence: MKFLVNVALVFMVVYISYIYADPIN-MTTSINNNLQRVRELAVQSANSAAAPGAAVDGT SLLTEVETPIRNEWGSRSNDSSDAAAGGAASLLTE-VETPIRNEWGSRSNDSSDAAAPGA ASLLTEVETP-TRSEWESRSSDSSDAAAGGAASLLTEVETPTRNEW-ESRSSDSSDAAAPGA ASLLTEVETLTRNGWGCRCSDSSDGGLKQIEDKLEE-ILSKLYHIENELARIKKLLGELEIL AIYSTVASSLVLL-VSLGAISFWMCSNGSLQCRICI (TL-M2e5x, SEQ ID NO:24), or a conservative variant thereof having at least 70%, 71%, 72%, 73%, 74%, 75%, 76%, 77%, 78%, 79%, 80%, 81%, 82%$, 83%, 84%, 85%, 86%, 87%, 88%, 89%, 90%, 91%, 92%, 93%, 94%, 95%, 96%, 97%, 98%, or 99% sequence identity to SEQ ID NO:24.

Also disclosed are polynucleotides comprising nucleic acid sequences encoding the disclosed fusion proteins. For example, the nucleic acid sequences can be operably linked to expression control sequences. Thus, also disclosed are expression vectors for producing the disclosed fusion proteins as well as cells containing these polynucleotides and vectors for replicating the polynucleotides and vectors or to produce the disclose fusion proteins and/or VLPs. Therefore, the disclosed cell can also contain nucleic acid sequences encoding an M1 protein, including a vector comprising the nucleic acid sequences encoding an M1 protein.

Also disclosed is a dual vector comprising a first nucleic acid sequence encoding the disclosed fusion protein and a second nucleic acid sequence encoding an M1 protein. For example, the M1 protein can have the amino acid sequence SEQ ID NO:27, or a conservative variant thereof having at least 70%, 71%, 72%, 73%, 74%, 75%, 76%, 77%, 78%, 79%, 80%, 81%, 82%$, 83%, 84%, 85%, 86%, 87%, 88%, 89%, 90%, 91%, 92%, 93%, 94%, 95%, 96%, 97%, 98%, or 99% sequence identity to SEQ ID NO:27. The nucleic acid sequence encoding the M1 protein can comprise the nucleic acid sequence SEQ ID NO:26, or a conservative variant thereof having at least 70%, 71%, 72%, 73%, 74%, 75%, 76%, 77%, 78%, 79%, 80%, 81%, 82%$, 83%, 84%, 85%, 86%, 87%, 88%, 89%, 90%, 91%, 92%, 93%, 94%, 95%, 96%, 97%, 98%, or 99% sequence identity to SEQ ID NO:26. In some embodiments, the nucleic acid sequence encoding the disclosed fusion protein is operably linked to a first expression control sequence; and the nucleic acid sequence encoding an M1 protein is operably linked to a second expression control sequence.

The cell can be a prokaryotic or eukaryotic cell. For example, the cell can be a bacterium, an insect cell, a yeast cell, or a mammalian cell. The cell can be a human cell. Suitable vectors can be routinely selected based on the choice of cell used to produce the VLP. For example, where insect cells are used, suitable vectors include baculoviruses.

Fusion Proteins

Fusion proteins, also known as chimeric proteins, are proteins created through the joining of two or more genes which originally coded for separate proteins. Translation of this fusion gene results in a single polypeptide with function properties derived from each of the original proteins. Recombinant fusion proteins can be created artificially by recombinant DNA technology for use in biological research or therapeutics.

The functionality of fusion proteins is made possible by the fact that many protein functional domains are modular. In other words, the linear portion of a polypeptide which corresponds to a given domain, such as a tyrosine kinase domain, may be removed from the rest of the protein without destroying its intrinsic enzymatic capability. Thus, any of the herein disclosed functional domains can be used to design a fusion protein.

A recombinant fusion protein is a protein created through genetic engineering of a fusion gene. This typically involves removing the stop codon from a cDNA sequence coding for the first protein, then appending the cDNA sequence of the second protein in frame through ligation or overlap extension PCR. That DNA sequence will then be expressed by a cell as a single protein. The protein can be engineered to include the full sequence of both original proteins, or only a portion of either.

If the two entities are proteins, often linker (or "spacer") peptides are also added which make it more likely that the proteins fold independently and behave as expected. Especially in the case where the linkers enable protein purification, linkers in protein or peptide fusions are sometimes engineered with cleavage sites for proteases or chemical agents which enable the liberation of the two separate proteins.

Virus Like Particles (VLPs)

The disclosed construct of heterologous M2e sequences may be expressed on the surface of a particle to mimic the natural conformation of M2 on influenza virions. For example, the disclosed fusion proteins may be incorporated into virus-like particles (VLPs) by including within the fusion protein a membrane anchor domain, such as a transmembrane domain and optional cytoplasmic domain of a viral envelope protein.

Non-replicating VLPs resemble infectious virus particles in structure and morphology, and contain immunologically relevant viral structural proteins. VLPs have been produced from both non-enveloped and enveloped viruses. Envelopes of VLPs are derived from the host cells similar to the way as enveloped viruses such as influenza A virus obtain their lipid envelopes from their host cells. Therefore, membrane-anchored proteins on the surfaces of enveloped viruses will be expressed in a native-like conformation if they are expressed in a membrane-anchored form.

Influenza VLPs involve lipid bilayers and host cell membrane proteins (Song, J. M., et al. J Proteome Res 2011 10:3450-3459). For example, Influenza VLPs containing the wild type M2 protein have been described (Song, J. M., et al. Proc Natl Acad Sci USA 2011 108:757-761; Song, J. M., et al. PLoS One 2011 6:e14538). Enveloped VLPs may be composed of influenza matrix 1 (M1) protein as a particle forming core. These VLPs are produced, for example, by coinfecting insect cells with one or more recombinant baculoviruses co-expressing M1 proteins and the disclosed fusion proteins, culturing the insect cells under physiological conditions, and purifying the VLPs from insect cell culture supernatants.

Influenza virus hemagglutinin (HA) and neuraminidase (NA) are large proteins that have the potential to mask smaller M2e proteins. Therefore, in some embodiments, HA and NA are not immobilized on the surface of the VLP.

Vaccine Compositions

Disclosed are vaccine compositions that comprise one or more of the fusion proteins described above. Although not required, the vaccine compositions optionally contain one or more immunostimulants. An immunostimulant refers to essentially any substance that enhances or potentiates an immune response (antibody or cell-mediated) to an exogenous antigen. One preferred type of immunostimulant is an adjuvant.

Many adjuvants contain a substance designed to protect the antigen from rapid catabolism, such as aluminum hydroxide or mineral oil, and a stimulator of immune responses, such as lipid A, *Bordetella pertussis* or *Mycobacterium tuberculosis* derived proteins. The adjuvant may be a submicron oil-in-water emulsion of a metabolizable oil and an emulsifying agent. For example, the adjuvant may comprise MF59™, which is a sub-micron oil-in-water emulsion of a squalene, polyoxyethylene sorbitan monooleate (Tween™ 80) and sorbitan trioleate. The adjuvant may also be a combination of the TLR4 agonist MPL (3-O-desacyl-4'-monophosphoryl lipid A) and aluminum salt, e.g., ASO4 (GlaxoSmithKline, Philadelphia, Pa.).

Certain adjuvants are commercially available as, for example, Freund's Incomplete Adjuvant and Complete Adjuvant (Difco Laboratories, Detroit, Mich.); Merck Adjuvant 65 (Merck and Company, Rahway, N.J.); AS01, AS02, AS03, and ASO4 (GlaxoSmithKline, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF, interleukin-2, -7, -12, and other like growth factors, may also be used as adjuvants.

The adjuvant composition can be a composition that induces an anti-inflammatory immune response (antibody or cell-mediated). Accordingly, high levels of anti-inflammatory cytokines (anti-inflammatory cytokines may include, but are not limited to, interleukin 4 (IL-4), interleukin 5 (IL-5), interleukin 10 (IL-10), and transforming growth factor beta (TGFβ). Optionally, an anti-inflammatory response would be mediated by CD4+ T helper cells. Bacterial flagellin has been shown to have adjuvant activity (McSorley et al., J. Immunol. 169:3914-19, 2002). Also disclosed are polypeptide sequences that encode flagellin proteins that can be used in adjuvant compositions.

Optionally, the adjuvants increase lipopolysaccharide (LPS) responsiveness. Illustrative adjuvants include but are not limited to, monophosphoryl lipid A (MPL), aminoalkyl glucosaminide 4-phosphates (AGPs), including, but not limited to RC-512, RC-522, RC-527, RC-529, RC-544, and RC-560 (Corixa, Hamilton, Mont.).

In addition, the adjuvant composition can be one that induces an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a subject will support an immune response that includes Th1- and Th2-type responses. Optionally, the level of Th1-type cytokines will increase to a greater extent than the level of Th2-type cytokines. The levels of these cytokines may be readily assessed using standard assays. Certain adjuvants for eliciting a predominantly Th1-type response include, for example, a combination of monophosphoryl lipid A, preferably 3-de-O-acylated monophosphoryl lipid A, together with an aluminum salt adjuvants are available from Corixa Corporation (Seattle, Wash.). CpG-containing oligonucleotides (in which the CpG dinucleotide is unmethylated) also induce a predominantly Th1 response. Another adjuvant comprises a saponin, such as Quil A, or derivatives thereof, including QS21 and QS7 (Aquila Biopharmaceuticals Inc., Framingham, Mass.); Escin; Digitonin; or *Gypsophila* or *Chenopodium quinoa* saponins Additional illustrative adjuvants for use in the disclosed vaccine compositions include Montamide ISA 720 (Seppic, France), SAF (Chiron, Calif., United States), ISCOMS (CSL), MF-59 (Chiron), the SBAS series of adjuvants (e.g., SBAS-2 or SBAS-4, available from GlaxoSmithKline, Philadelphia, Pa.), Detox (Enhanzyn™) (Corixa, Hamilton, Mont.), RC-529 (Corixa, Hamilton, Mont.) and other aminoalkyl glucosaminide 4-phosphates (AGPs).

In some embodiments, the adjuvant is incorporated into the VLP in a membrane-anchored form. For example, GM-CSF or a bacterial flagellin protein containing a membrane anchor can be incorporated into the disclosed VLPs.

Pharmaceutical Compositions

The disclosed vaccines can be used therapeutically in combination with a pharmaceutically acceptable carrier. By "pharmaceutically acceptable" is meant a material that is not biologically or otherwise undesirable, i.e., the material may be administered to a subject without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The materials may be in solution, suspension (for example, incorporated into microparticles, liposomes, or cells). Suitable carriers and their formulations are described in Remington: The Science and Practice of Pharmacy (22nd ed.) eds. Loyd V. Allen, Jr., et al., Pharmaceutical Press, 2012. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of vaccines to humans, including solutions such as sterile water, saline, and buffered solutions at physiological pH. Pharmaceutical compositions may include carriers, thickeners, diluents, buffers, preservatives, surface active agents and the like in addition to the vaccine. Pharmaceutical compositions may also include one or more active ingredients such as antimicrobial agents, antiinflammatory agents, anesthetics, and the like.

The disclosed vaccines are preferably formulated for delivery via intranasal, intramuscular, subcutaneous, transdermal or sublingual administration.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Combinations

The disclosed vaccine can be used to supplement existing human vaccines to improve cross protection. Therefore, the disclosed vaccine can further include (or be administered in combination with) a whole inactivated virus, split viral vaccine, live attenuated influenza vaccine, or another influenza virus-like particle (VLP) vaccine. For example, the disclosed vaccine can be combined with a trivalent inactivated vaccine (TIV) (e.g., containing killed A/H1N1, A/H3N2, and B), trivalent live attenuated influenza vaccine, trivalent split vaccines, or trivalent subunit influenza vaccines.

The disclosed vaccine can further include (or be administered in combination with) one or more of classes of antibiotics, steroids, analgesics, anti-inflammatory agents, anti-histaminic agents, or any combination thereof. Antibiotics include Aminoglycosides, Cephalosporins, Chloramphenicol, Clindamycin, Erythromycins, Fluoroquinolones, Macrolides, Azolides, Metronidazole, Penicillins, Tetracyclines, Trimethoprim-sulfamethoxazole, and Vancomycin. Suitable steroids include andranes, such as testosterone. Narcotic and non-narcotic analgesics include morphine, codeine, heroin, hydromorphone, levorphanol, meperidine, methadone, oxydone, propoxyphene, fentanyl, methadone, naloxone, buprenorphine, butorphanol, nalbuphine, and pentazocine. Anti-inflammatory agents include alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, decanoate, deflazacort, delatestryl, depo-testosterone, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, mesterolone, methandrostenolone, methenolone, methenolone acetate, methylprednisolone suleptanate, momiflumate, nabumetone, nandrolone, naproxen, naproxen sodium, naproxol, nimazone, olsalazine sodium, orgotein, orpanoxin, oxandrolane, oxaprozin, oxyphenbutazone, oxymetholone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, stanozolol, sudoxicam, sulindac, suprofen, talmetacin, talniflumate, talosalate, tebufelone, tenidap, tenidap sodium, tenoxicam, tesicam, tesimide, testosterone, testosterone blends, tetrydamine, tiopinac, tixocortol pivalate, tolmetin, tolmetin sodium, triclonide, triflumidate, zidometacin, and zomepirac sodium. Anti-histaminic agents include ethanolamines (e.g., diphenhydrmine carbinoxamine), Ethylenediamine (e.g., tripelennamine pyrilamine), Alkylamine (e.g., chlorpheniramine, dexchlorpheniramine, brompheniramine, triprolidine), other anti-histamines like astemizole, loratadine, fexofenadine, bropheniramine, clemastine, acetaminophen, pseudoephedrine, triprolidine).

Methods of Vaccinating a Subject

A method of vaccinating a subject for influenza A is disclosed that involves administering the disclosed cross-protective influenza vaccine to a subject in need thereof. The disclosed vaccine may be administered in a number of ways. For example, the disclosed vaccine can be administered intramuscularly, intranasally, or by microneedle in the skin. The compositions may be administered orally, intravenously, subcutaneously, transdermally (e.g., by microneedle), intraperitoneally, ophthalmically, vaginally, rectally, sublingually, or by inhalation.

Parenteral administration of the composition, if used, is generally characterized by injection. Injectables can be prepared in conventional forms, either as liquid solutions or suspensions, solid forms suitable for solution of suspension in liquid prior to injection, or as emulsions. A revised approach for parenteral administration involves use of a slow release or sustained release system such that a constant dosage is maintained.

The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein. For example, effective dosages and schedules for administering the compositions may be determined empirically, and making such determinations is within the skill in the art. The dosage ranges for the administration of the compositions are those large enough to produce the desired effect in which the symptoms disorder are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. A typical dosage of the disclosed vaccine used alone might range from about 1 μg/kg to up to 100 mg/kg of body weight or more per vaccination, such as 10 μg/kg to 50 mg/kg, or 50 μg/kg to 10 mg/kg, depending on the factors mentioned above.

A number of embodiments of the invention have been described. Nevertheless, it will be understood that various modifications may be made without departing from the spirit and scope of the invention.

EXAMPLES

Example 1: Preparation of Virus-Like Particles Containing Tandem Repeat M2 Extracellular Domains Materials and Methods
Cells, Viruses, and Reagents

*Spodoptera frugiperda* sf9 insect cells (ATCC, CRL-1711) were maintained in SF900-II serum free medium (Invitrogen, Carlsbad, Calif.) at 27° C. and used for production of recombinant baculoviruses (rBVs) and VLPs. Ten-day-old embryonated chicken eggs were used for virus propagation and viral titration. Influenza A viruses, A/California/4/2009 (2009 pandemic H1N1 virus), mouse adapted A/Philippines/2/1982 (H3N2) and A/PR/8/34 (H1N1) were provided. Reassortant H5N1 virus HA and NA derived from ANietnam/1203/2004, and the remaining backbone genes from A/PR/8/34 virus were obtained as described (Song J M, et al. (2010). *Antiviral Res* 88: 244-247). Inactivation of the purified virus was performed by mixing the virus with formalin at a final concentration of 1:4000 (v/v) (Quan F S, et al. (2008). *J Virol* 82: 1350-1359). Genes for five tandem repeats of M2 ectodomain (M2e5x) and 4 sets of M2e peptide (a2-20), human type-SLLTEVET PIRNEWGSRSN DSSD (SEQ ID NO:5), Swine type-SLLTEVET PTRSEWESRSS DSSD (SEQ ID NO:6), Avian I type-SLLTEVET PTRNEWESRSS DSSD (SEQ ID NO:7) and Avian II type-SLLTEVET LTRNGWGCRCS DSSD (SEQ ID NO:11), were chemically synthesized (GenScript, Piscataway, N.J.), and used in this study.

Preparation of TL-M2e5x VLP

TL-M2e5x VLPs with influenza matrix protein M1 were prepared as described (Song J M, et al. (2011). *PLoS One* 6: e14538). A synthesized DNA fragment of TL-M2e5x construct was cloned into the pFastBac™ vector plasmid which was subsequently used to make recombinant Bacmid baculovirus DNAs (rAcNPV) using DH10Bac competent cells (Invitrogen, Carlsbad, Calif.). A recombinant baculovirus (rBV) expressing TL-M2e5x was generated by transfection of sf9 insect cells following the manufacturer's instruction. To produce influenza VLPs containing TL-M2e5x protein, rBVs expressing M1 and TL-M2e5x protein were co-infected into sf9 insect cells at multiplication of infection of 1:2. At 2 days post-infection, the infected cell culture supernatants were clarified by centrifugation (6000 rpm, 30 min) and then were concentrated by the QuixStand™ hollow fiber based ultrafiltration system (GE Healthcare, Piscataway, N.J.). TL-M2e5x VLPs were purified by sucrose gradient ultracentrifugation with layers of 20% and 60% (wt/vol) as previously described (Song J M, et al. (2011). *PLoS One* 6: e14538). Influenza A virus M2 monoclonal antibody 14C2 (Abcam Inc., Cambridge, Mass.) was used for detection of TL-M2e5x protein by western blot.

Statistical Analysis

To determine the statistical significance, a two-tailed Student's t-test was used when comparing two different conditions. A p value less than 0.05 was considered to be significant.

Results

Preparation of VLPs Containing Tandem Repeat M2e

To improve M2 VLP vaccines, an M2 construct was designed at a molecular level and genetically constructed. A tandem repeat of M2e (TL-M2e5x) was introduced to increase the density and variation of M2e epitopes. The TL-M2e5x is composed of heterologous M2e sequences including conserved sequences derived from human, swine, and avian origin influenza A viruses (FIG. 1A). Also, a domain (GCN4, SEQ ID NO:6) known to stabilize oligomer formation was linked to the C-terminal part of TL-M2e5x. The signal peptide from the honeybee protein mellitin (SEQ ID NO:5) was added to the N-terminus of TL-M2e5x for efficient expression on insect cell surfaces, thus enhancing incorporation into VLPs (Wang B Z, et al. (2007). *J Virol* 81: 10869-10878). Finally, the transmembrane and cytoplasmic tail domains were replaced with those derived from hemagglutinin (HA) (SEQ ID NO:7) of A/PR/8/34 virus to increase the incorporation into VLPs (FIG. 1A).

Figure 1B:
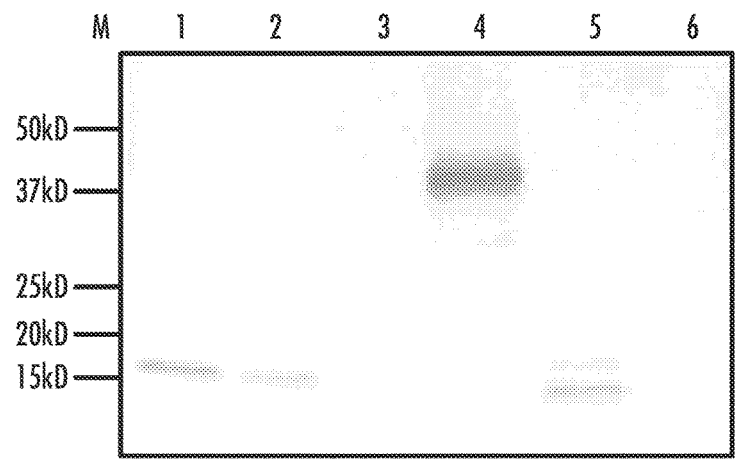
Figure 1C:
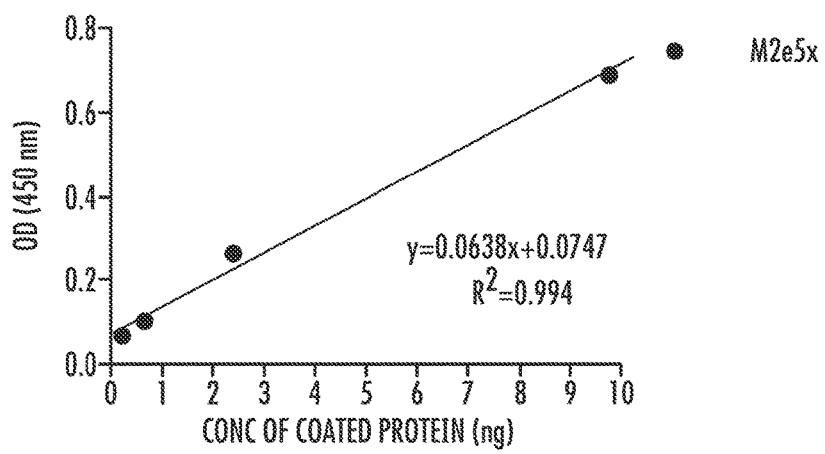
Figure 1D:
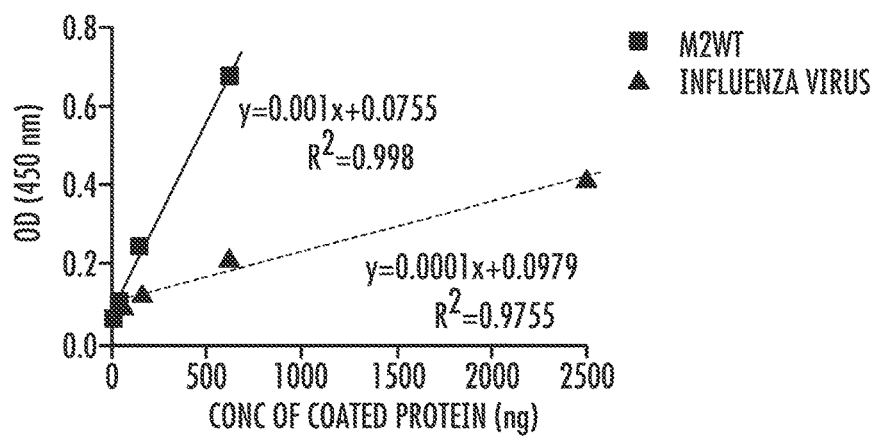

TL-M2e5x VLPs produced in Sf9 insect cells were found to be incorporated into VLPs at higher levels than the wild type M2 VLP (M2WT VLP) and influenza virus as determined by western blot using anti-M2 monoclonal antibody 14C2 (FIG. 1B). For quantitative comparison of M2e epitopes in VLP vaccines or virus, we compared M2e specific monoclonal antibody reactivity by ELISA using TL-M2e5x and M2WT VLPs and influenza virus (FIG. 1C, 1D). It was estimated that the reactivity of M2 monoclonal antibody 14C2 to TL-M2e5x VLP was at least 60 fold higher than that to M2WT VLP. Compared to that of A/Philippines/ 2/82 virus, the reactivity 14C2 M2 antibody to TL-M2e5x VLP was approximately 500 fold higher (FIG. 1C, 1D). The M2 antibody 14C2 reactivity to TL-M2e5x VLP was not increased by membrane-disrupting detergent treatment, indicating the reactivity to the surface-expressed M2e epitopes on VLPs. These results indicate that the tandem repeat of heterologous M2e may be presented on the VLPs in a conformation highly reactive to M2e recognizing antibody 14C2.

Figure 1E:

For expression of recombinant TL-M2e5x universal vaccines using an alternative production system, the DNA construct of TL-M2e5x was cloned into the yeast expression shuttle vector (pPIC9-5M2e). This recombinant yeast shuttle vector was transformed into yeast cells (*Pichia pastoris* GS115). A recombinant yeast cell GS115 expressing TL-M2e5x was selected and grown to produce TL-M2e5x recombinant subunit vaccines. The TL-M2e5x protein vaccines secreted into culture supernatants were run on a SDS-PAGE (sodium dodecyl sulfate polyacrylamide gel electrophoresis) and western blot (FIG. 1E).

Example 2: TL-M2e5x VLPs Induce M2e Specific Antibody Responses

Materials and Methods
Immunization and Challenge

For animal experiments, 6-8 week old female BALB/c mice (Harlan Laboratories, Indianapolis, Ind.) were intramuscularly immunized with 10 µg (total protein) of TL-M2e5x VLP or M2WT VLP at a 4-week interval. Three weeks after prime or boost immunization, mice were bled to test immune responses. Six weeks after boost immunization, mice (n=8) were challenged with 4×LD$_{50}$ (50% mouse lethal dose LD$_{50}$) of A/Philippines/2/82 (H3N2) and A/California/ 4/2009 (H1N1) influenza viruses. To determine the long-term protective efficacy, additional groups of mice were challenged with a lethal dose (4 LD$_{50}$) of A/Philippines/2/82 influenza virus 8 months post boost vaccination. Mice were monitored daily to record weight changes and mortality (25% loss in body weight as the Institutional Animal Care and Use Committee (IACUC) endpoint).

Determination of Antibody Responses

M2e specific serum antibody responses were determined by ELISA using synthetic human, swine, avian I and avian II type M2e peptides or inactivated purified virions (4 mg/ml) as a coating antigen as previously described (Song J M, et al. (2011). *PLoS One* 6: e14538). Briefly, HRP-conjugated goat anti-mouse IgG, IgG1, or IgG2a were used as secondary antibodies to determine total IgG or IgG isotype antibodies. The substrate TMB (Sigma-Aldrich, St. Louis, Mo.) was used to develop color and 1M H$_3$PO$_4$ was used to stop developing color reaction. The optical density at 450 nm was read using an ELISA reader.

Results

Figure 2A:
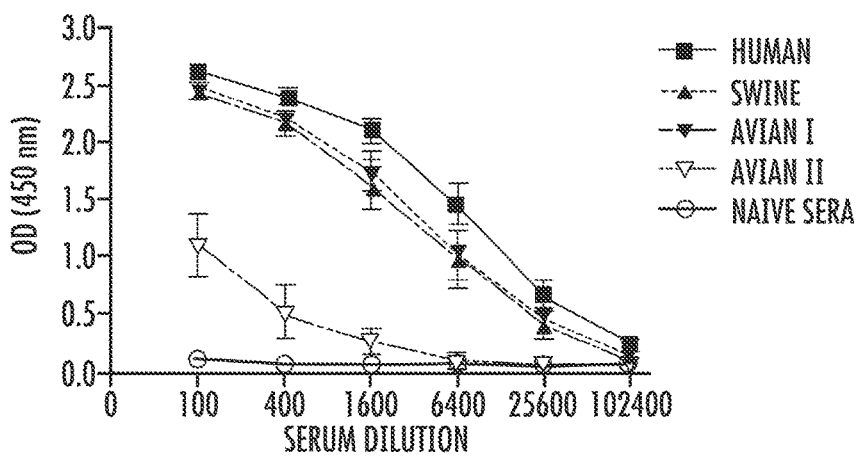
FIGS. 2A to 2D show M2e-specific total IgG and IgG isotype antibody responses. BALB/c mice (N=8) were immunized with 10 µg of TL-M2e5x VLP and M2WT VLP.

Although the M2 ectodomain (M2e) is highly conserved among human influenza A strains, there are some amino acid replacements in the swine or avian origin influenza viruses (Liu W, et al. (2005). *Microbes Infect* 7: 171-177). Thus, the reactivity of TL-M2e5x VLP immune sera with M2e peptide sequences of swine or avian influenza A virus was tested (FIG. 2). Immune sera collected from mice boosted with TL-M2e5x VLPs showed substantial levels of antibody reactivity to swine and avian type I M2e peptides (FIG. 2*a*). The reactivity to the avian type II M2e peptide was found to be lower than others. This low reactivity might be due to the fact that the avian type II peptide epitope is located at the most proximal region to the membrane in the TL-M2e5x construct (FIG. 15B). The reactivity to human type M2e peptide antigen was approximately 2 fold higher than the other types, possibly due to its most external location, implicating positional effects on immunogenicity.

Figure 2B:
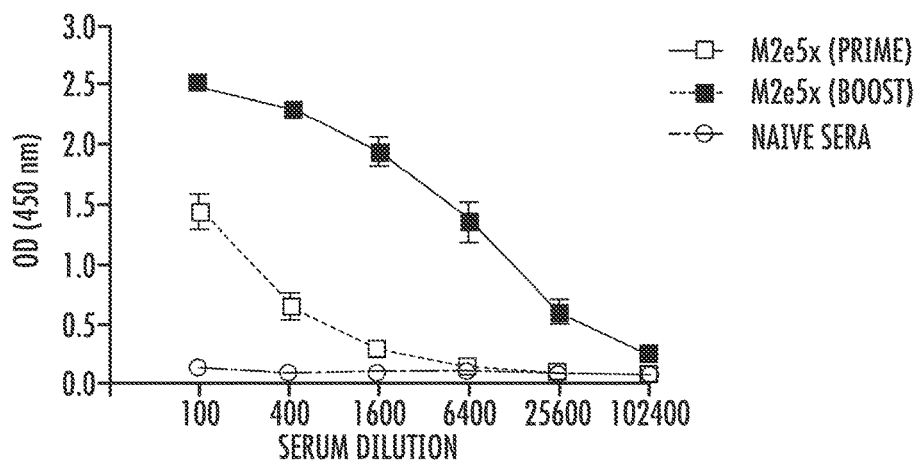
Figure 2C:
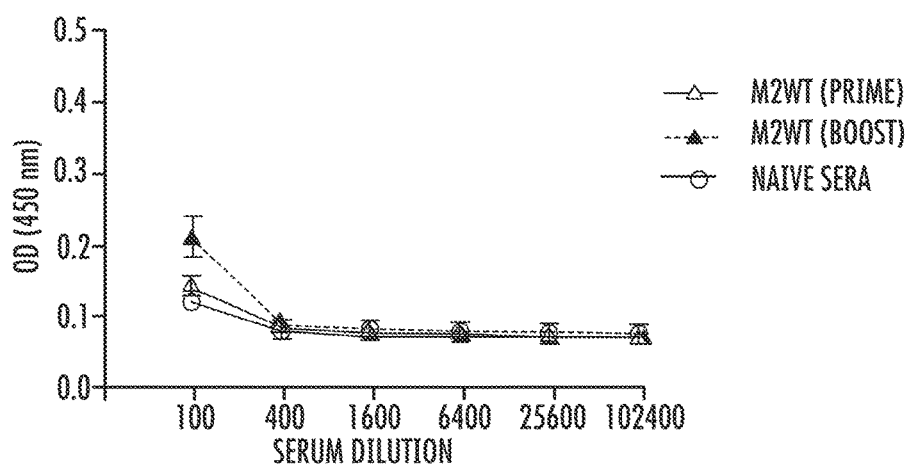

To determine the immunogenicity of influenza VLPs containing TL-M2e5x and M2WT proteins, groups of mice (8 BALB/c mice per group) were intramuscularly immunized with 10 µg of VLPs twice at weeks 0 and 4. Levels of M2e specific IgG antibodies were analyzed in immune sera by ELISA using an M2e peptide antigen that is highly conserved among human influenza A viruses. At 3 weeks after priming, M2e specific antibodies were detected at significant levels in the group of mice immunized with TL-M2e5x VLPs (FIG. 2B). In contrast, immunization with M2WT VLPs induced only marginal levels of M2e specific antibodies (FIG. 2C). After boost immunization, antibodies specific to M2e were observed at significantly increased levels, over 60 fold higher compared to those observed after priming in the TL-M2e5x VLP group (FIG. 2B). The M2WT VLPs were not highly effective in inducing boost immune responses (FIG. 2C).

Figure 2D:
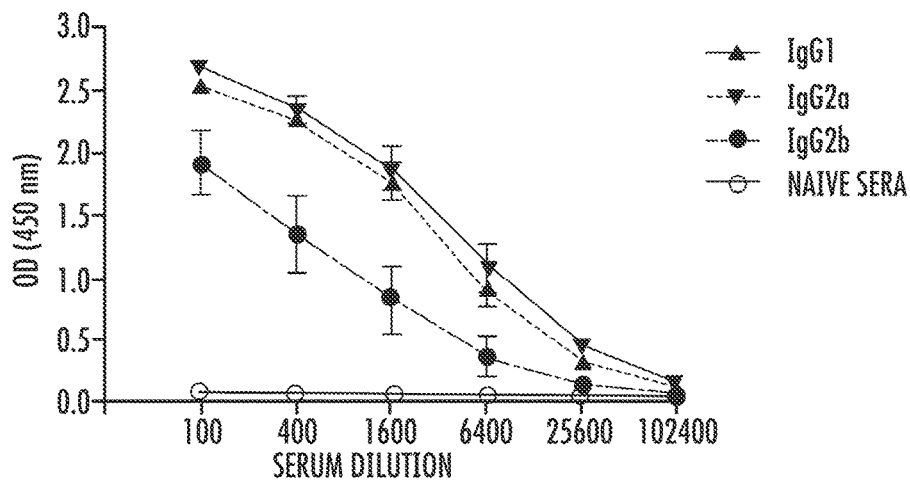

When IgG isotypes (IgG1, IgG2a, IgG2b) specific to M2e peptide antigen were determined, the level of IgG1 was found to be similar to that of IgG2a in boost immune sera (FIG. 2D). Also, IgG2b isotype antibody was observed at a substantial level. Thus, TL-M2e5x VLP vaccines seem to be effective in inducing balanced IgG1 and IgG2a as well as IgG2b antibody responses.

Example 3: TL-M2e5x VLP-Induced Antibody is Cross-Reactive with Different Influenza Viruses Materials and Methods
Cross Protective Efficacy Test of Immune Sera To test cross protective efficacy of immune sera in vivo, serum samples were collected from mice immunized with TL-M2e5x VLP and M2WT VLP on 3 weeks and 8 months after boost immunization. The 4 or 8 times diluted sera were heat-inactivated at 56° C. for 30 min and the serum samples were mixed with same volume of six lethal dose (6 LD$_{50}$) of influenza virus and incubated at room temperature for 30 min as described (Quan F S, et al. (2008). J Virol 82: 1350-1359). A mixture (6 LD$_{50}$) of a lethal infectious dose of A/PR/8/34 (H1N1) or A/Vietnam/1203/04 (H5N1) influenza virus with sera was administered to naive mice (N=4 BALB/c), and body weight and survival rates were monitored daily.

Results

Figure 3A:
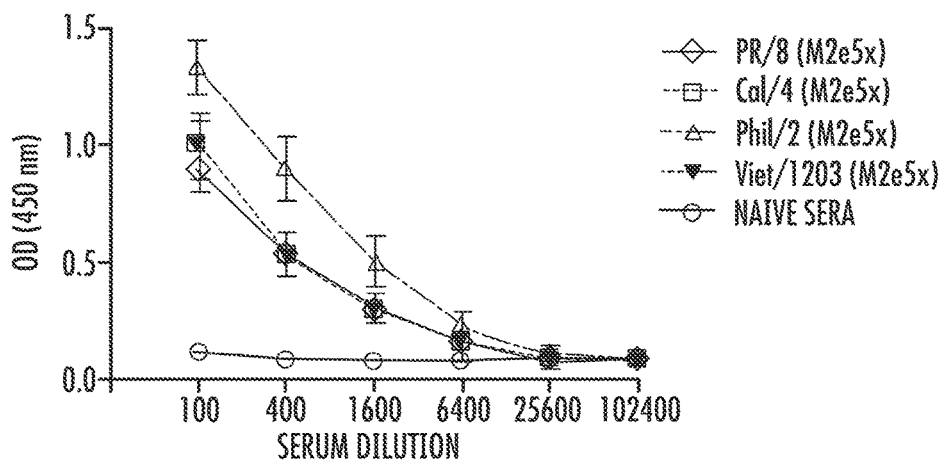
FIGS. 3A to 3B show IgG antibody responses reactive to influenza viruses. Inactivated influenza viruses, A/PR/8/34 (H1N1), A/California/4/2009(H1N1), A/Philippines/2/82 (H3N2) and reassortant A/Vietnam/1203/2004(H5N1), were used as coating antigen for antibody detection.
Figure 3B:
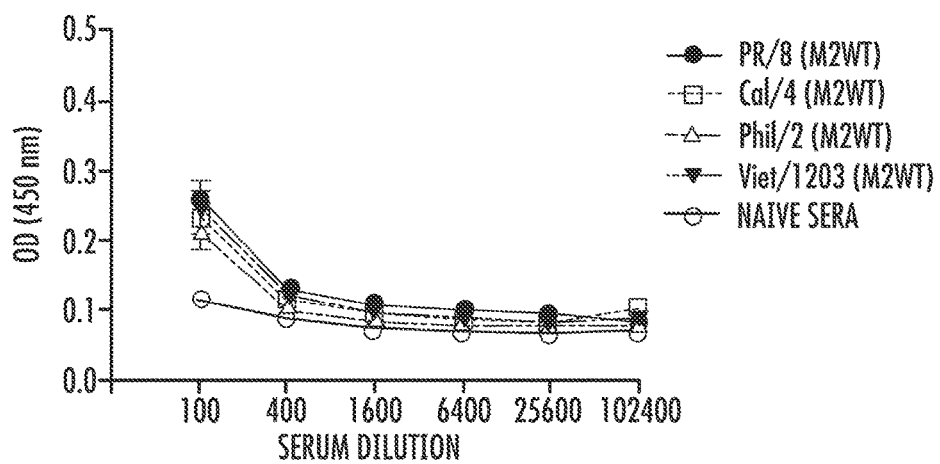

It is important to determine the reactivity of M2e specific antibodies to different strains of influenza viruses, which may provide correlative insight into the efficacy of cross protection. Whole inactivated virus A/California/4/2009 (H1N1), A/PR/8/34 (H1N1), A/Philippines/2/82 (H3N2), and A/Vietnam/1203/2004 (H5N1) were used as ELISA coating antigens (FIG. 3). Immune sera showed high levels of antibody responses cross-reactive to virus particles (FIG. 3A). Cross-reactivity to A/Philippines/2/82 virus was approximately 4 fold higher than that to the swine origin A/California/2009 virus or other viruses which showed similar binding properties to TL-M2e5x VLP boost immune sera (FIG. 3A). In contrast, M2WT VLP immune sera showed low levels of reactivity to viral antigens although these levels were higher than naïve sera (FIG. 3B). Therefore, these results indicate that TL-M2e5x VLPs are highly immunogenic and capable of inducing antibodies reactive to influenza A virions in the absence of adjuvant regardless of HA subtype.

Figure 4A:
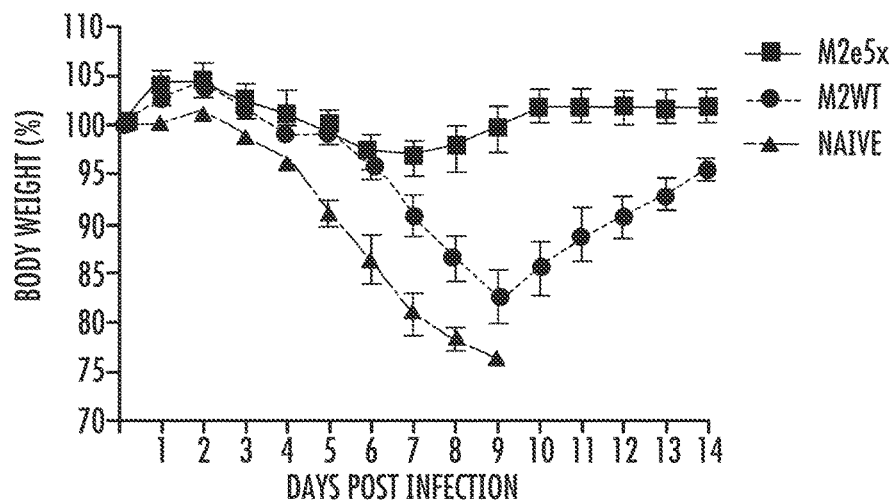
FIGS. 4A to 4D show TL-M2e5x VLP vaccination induces improved cross protection. At 6 weeks after boost vaccination, groups of mice (N=4) were challenged with a lethal dose ($4 \times LD_{50}$) of influenza viruses A/Philippines/2/82 (H3N2) (FIGS. 4A-4B) or A/California/4/2009 (H1N1) (FIGS. 4C-4D) Average body weight changes (FIGS. 4A and 4C) and survival rates (FIGS. 4B and 4D) were monitored for 14 days. Error bars indicates SEM. LD, lethal dose.
Figure 4B:
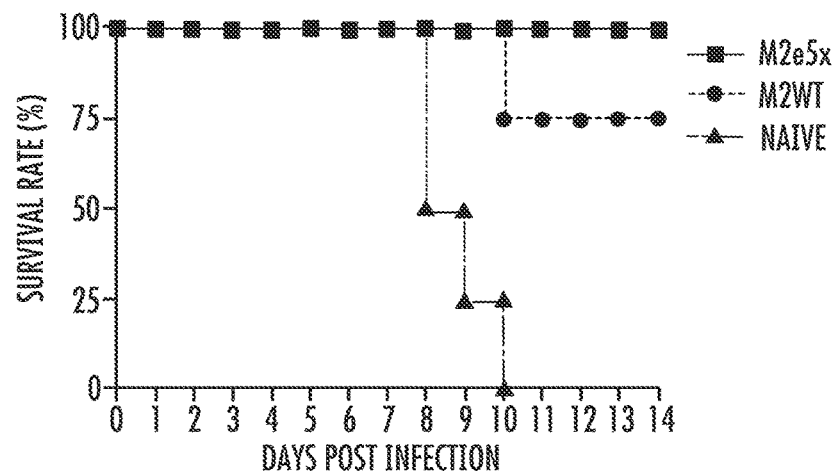
Figure 4C:
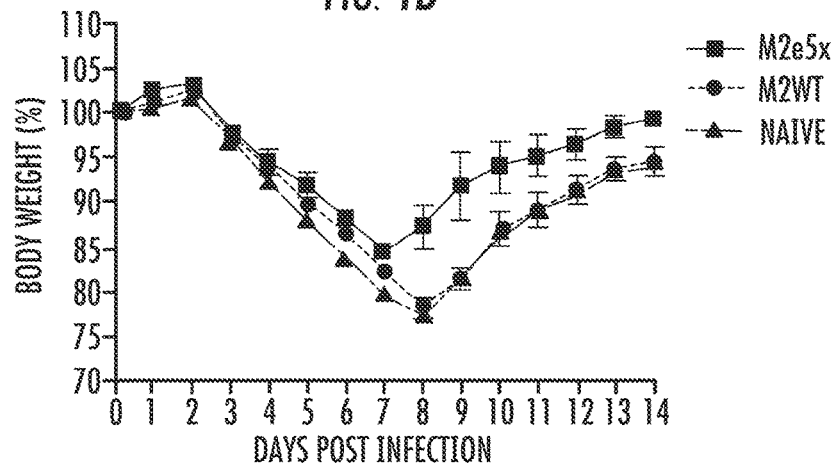
Figure 4D:
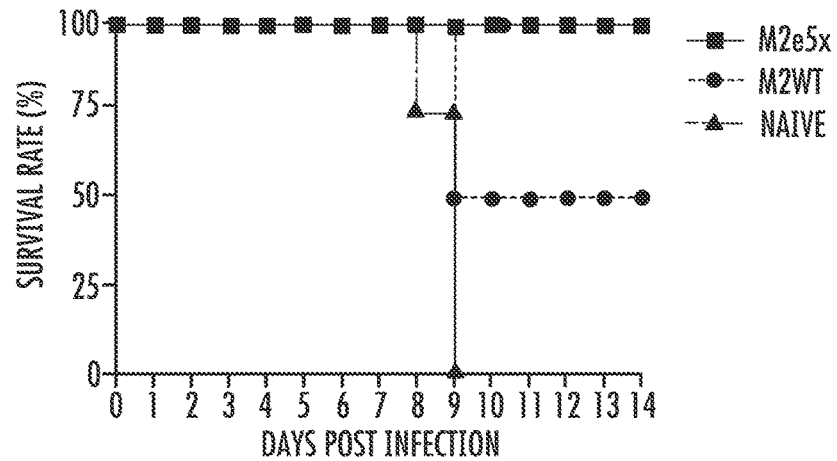

Example 4: TL-M2e5x VLPs Provide Protection Against Both H3N2 and H1N1 Viruses Results To compare the efficacy of TL-M2e5x VLPs with that of M2WT VLPs in conferring protection against lethal challenge infection, groups of mice were intramuscularly immunized and challenged with a lethal dose of A/Philippines/82 (H3N2) and A/California/4/2009 (H1N1) influenza viruses at 6 weeks after boosting (FIGS. 4A-4D). In the A/Philippines/2/82 protection experiment, the body weight changes and survival rates were monitored following challenge infection. All naïve mice lost over 25% in body weight and had to be euthanized (FIGS. 4A-4D). The TL-M2e5x VLP vaccinated mice showed a slight loss in body weight post challenge and then recovered to the normal body weight, resulting in 100% protection (FIG. 4A). In contrast, M2WT VLP vaccinated mice showed a significant loss of approximately 17% in body weight as well as a substantial delay in recovering body weight (FIG. 4A). The M2WT VLP group showed 75% protection against lethal challenge with A/Philippines H3N2 virus (FIG. 4B). The TL-M2e5x VLP group also showed 100% survival after lethal challenge with A/California/4/2009 (H1N1) influenza virus (FIG. 4C, 4D). Despite a body weight loss of 15%, all mice recovered to normal body weight in the TL-M2e5x VLP group (FIG. 4C). However, the M2WT VLP group showed approximately 22% body weight loss and only a survival rate of 50%, and a delay in recovery of body weight after lethal challenge with A/California/4/2009 (H1N1) influenza virus (FIG. 4C,4D). These results demonstrate that TL-M2e5x VLPs are superior to M2WT VLPs in conferring cross protection after intramuscular vaccination.

Example 5: Intramuscular Immunization with TL-M2e5x VLPs Induces Recall Mucosal Antibodies Materials and Methods Preparation of Bronchoalveolar Lavage Fluids and Lung Extracts Lung tissues were isolated from mice sacrificed at day 5 post challenge with influenza A/Philippines/2/1982 (H3N2) virus. Lung extracts were prepared using a mechanical tissue grinder with 1.5 ml of PBS per each lung and viral titers were determined using 10-day-old embryonated chicken eggs (Wen H S, et al. (1959). *J Infect Disease* 105: 9-17). Lung cells were recovered from mechanically grinded lung samples by centrifugation (12000 rpm, 5 min) for the determination of T cell response. Bronchoalveolar lavage fluids (BALF) were obtained by infusing 1 ml of PBS using a 25-gauge catheter (Exelint International Co., Los Angeles, Calif.) into the lungs via the trachea, and used for antibody response.

Results

Figure 5A:
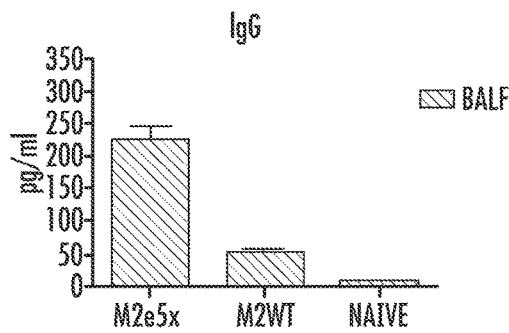
FIGS. 5A to 5D show antibody responses, virus and inflammatory cytokine levels in lungs after challenge. Levels of IgG and IgA antibodies, and lung viral titers and IL-6 cytokine in bronchoalveolar lavage fluids (BALF) were determined from TL-M2e5x VLP or M2WT VLP immunized mice at day 5 after challenge with $4 \times LD_{50}$ of A/Philippines/2/83 (H3N2) virus (N=3).
Figure 5B:
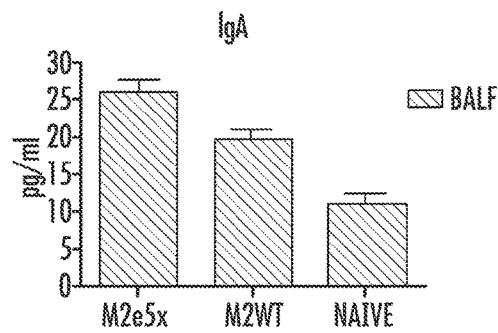

Mucosal immunity is important for conferring protection against influenza virus. M2e specific IgG and IgA antibody responses in BALF were therefore evaluated (FIG. 5A, 5B). Significant levels of IgG antibody responses specific to M2e were observed in BALF in TL-M2e5x VLP immunized mice at day 5 post challenge (A/Philippines/2/82 virus) (FIG. 5A). M2WT VLP group showed low levels of IgG antibodies recognizing antibodies after challenge, indicating less effective recall immune responses (FIG. 5A). Interestingly, a rapid increase in IgA antibodies specific to M2e peptide was observed in BALF after challenge (FIG. 5B). As expected, both mucosal IgG and IgA antibody responses were higher in the TL-M2e5x VLP group than those in M2WT group (FIG. 5A, 5B).

Figure 5C:
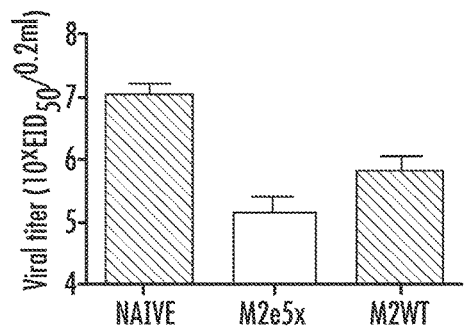

Example 6: TL-M2e5x VLP Vaccination Lower Lung Viral Titers and Inflammatory Cytokine Levels Results To better assess the protective efficacy against A/Philippines/2/82 (H3N2), lung viral titers were determined at day 5 after challenge. The group of mice intramuscularly immunized with TL-M2e5x VLPs showed approximately 4-fold and 100-fold lower lung viral titers (A/Philippines/2/82 virus) compared to those in the M2WT VLP and naïve challenge control group respectively (FIG. 5C). Therefore, it is likely that M2e specific immune responses in systemic and mucosal sites can effectively contribute to controlling virus replication after intramuscular immunization.

Figure 5D:
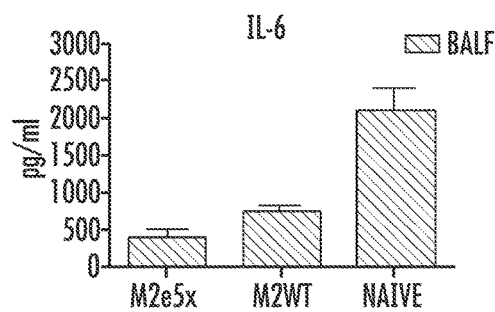

Pro-inflammatory cytokines are involved in causing tissue damage, which may lead to death. Cytokines in BALF from TL-M2e5x VLP or M2WT VLP immunized mice after challenge were determined (FIG. 5D). Significantly higher levels of interleukin (IL)-6 were observed in BALF from naïve mice infected with A/Philippines/2/82 virus than TL-M2e5x VLP or M2WT VLP immunized mice, indicating lung inflammatory responses probably due to high viral replication (FIG. 5D). The level of IL-6 in BALF from TL-M2e5x VLP immunized mice was lower than that of M2WT VLP immunized mice. Therefore, these results indicate that modulation of cytokine production as a result of TL-M2e5x VLP immunization plays a role in improving cross protection upon lethal challenge.

Example 7: TL-M2e5x VLPs are an Effective Vaccine for Inducing M2e Specific T Cell Responses Materials and Methods Determination of T Cell Responses Splenocytes and lung cells were isolated from the same mice sacrificed at 5 day post challenge and post vaccination and single cell suspensions were prepared as described (Quan F S, et al. (2009). *PLoS One* 4: e7152). Interferon (IFN)-γ and interleukin (IL)-4 secreting cell spots were determined on Multi-screen 96 well plates (Millipore, Billerica, Mass.) coated with cytokine specific capture antibodies as described (Song J M, et al. (2010). *Virology* 405: 165-175). Briefly, $0.5 \times 10^6$ spleen cells per well and $0.2 \times 10^6$ lung cells were cultured with M2e human type peptide (2 μm/ml) as an antigenic stimulator. After 36 h incubation, the spots of IFN-γ or IL-4 secreting T cells were counted using an ELISpot reader (BioSys, Miami, Fla.).

Results

Figure 6A:
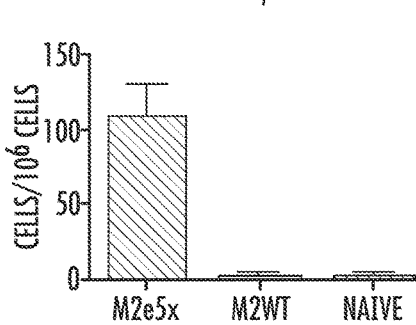
FIGS. 6A to 6D show enhanced anamnestic cellular immune responses by TL-M2e5x VLP vaccination.
Figure 6B:
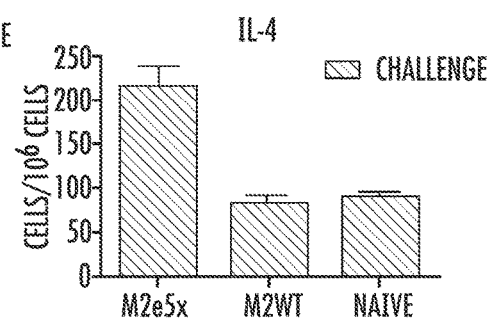
Figure 6C:
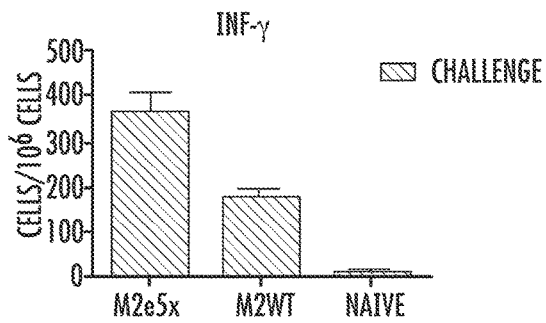
Figure 6D:
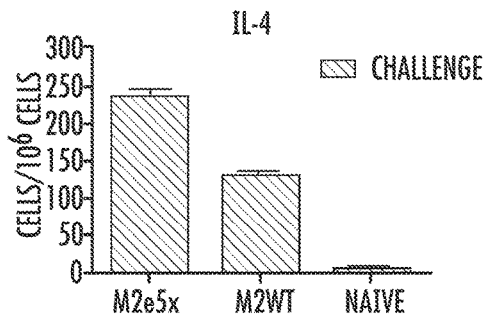

T cell responses are known to contribute to broadening cross protective immunity. After in vitro stimulation of cells with an M2e specific peptide, cytokine producing spots of lymphocytes from spleen were measured as an indicator of T cell responses (FIGS. 6A-6D). Mice were challenged with A/Philippines/2/82 virus at 8 weeks after boost and cells from tissues or BALF samples were collected at day 5 post challenge to determine recall immune responses of M2e specific T cells. Over 10 fold higher levels of IFN-γ secreting spleen cells were observed in the TL-M2e5x VLP vaccinated mice compared to those in the M2WT VLP or naïve group (FIG. 6A). Approximately 3 fold higher levels of IL-4 secreting cells were observed in the TL-M2e5x VLP vaccinated mice compared to those in the M2WT or infected naive mice that were displaying some levels of IL-4 secreting spots (FIG. 6B). Also, in cells of mixed lung and BALF samples, spot numbers of IFN-γ and IL-4 secreting cells were higher in TL-M2e5x VLP vaccinated mice than in M2WT VLP vaccinated mice (FIGS. 6C, 6D). Importantly, the M2WT VLP group showed substantial levels of IFN-γ and IL-4 secreting cell spots in mucosal tissue cells compared to the naïve infected control (FIG. 6C, 6D). It is interesting to note that spots of IFN-γ were higher than those of IL-4 (FIG. 6C, 6D) whereas the reverse pattern was observed with spleen cells (FIG. 6A, 6B). These results provide evidence that TL-M2e5x VLP immunization more effectively induced M2e specific INF-γ and IL-4 secreting T cell recall responses in spleens and lung cells compared to M2WT VLP vaccination.

Example 8: TL-M2e5x Immunity is Long-Lived

Results

Figure 7A:
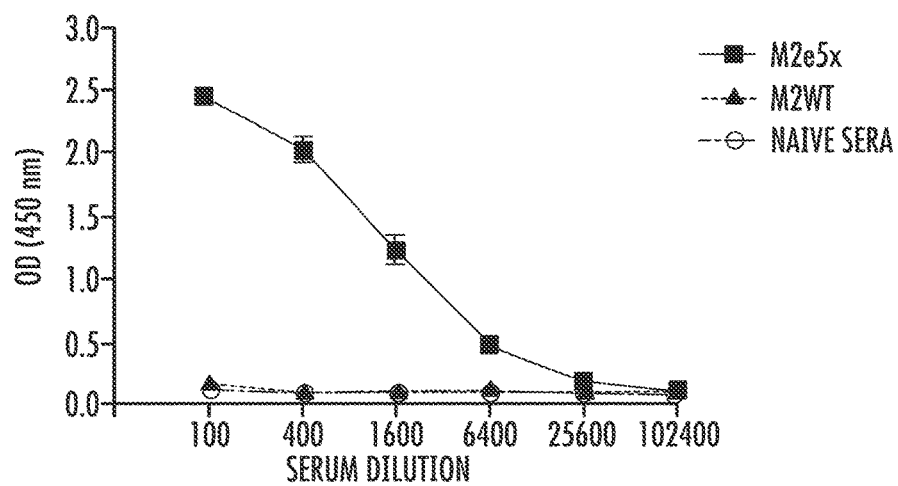
FIGS. 7A to 7D show TL-M2e5x VLP vaccination induces long-term protection.
Figure 7B:
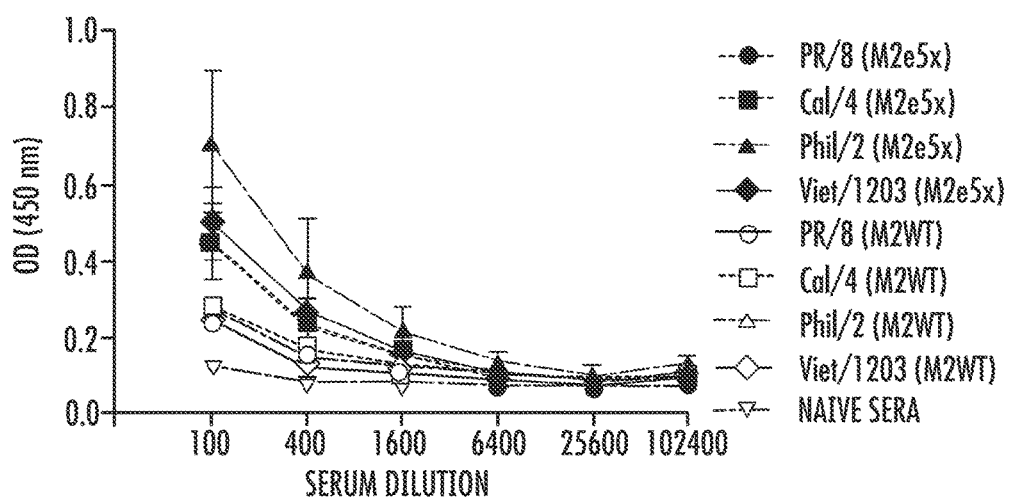
Figure 7C:
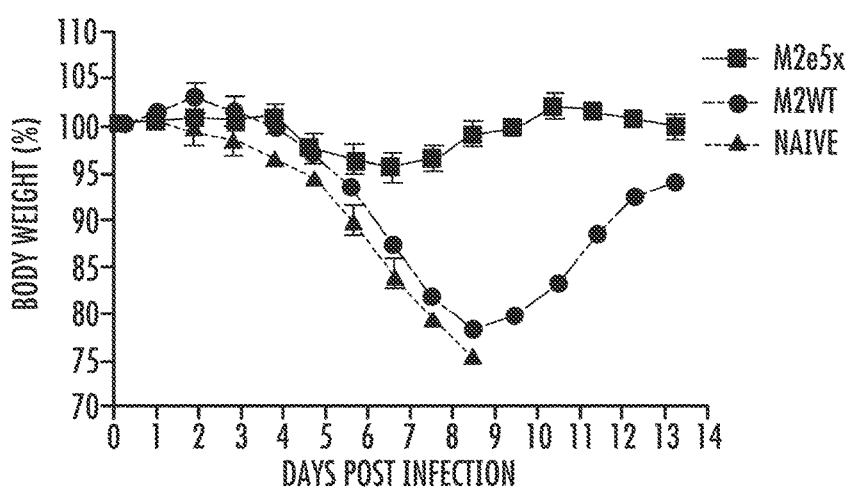
Figure 7D:
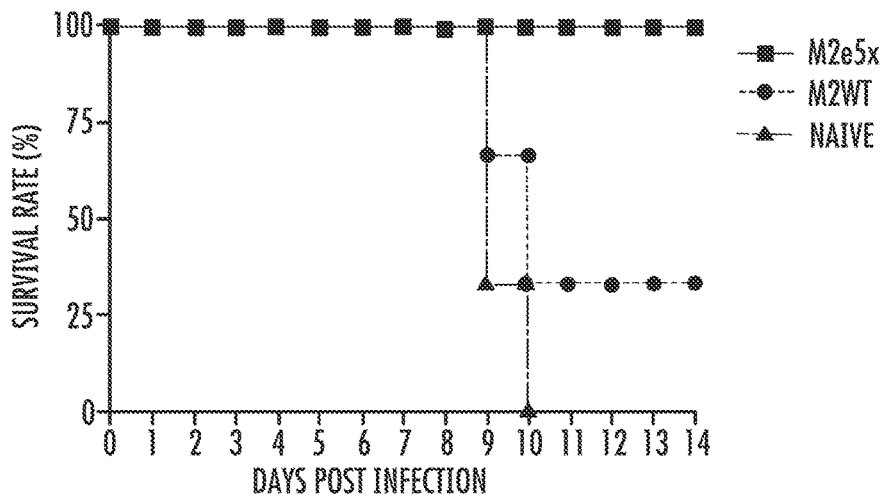

One of the goals for vaccination is to induce long-term protective immunity. Thus, the longevity of M2e antibody responses induced by TL-M2e5x VLP vaccination was determined. The M2e specific antibody responses to TL-M2e5x immunized sera were maintained at significantly high levels (FIG. 7A) and influenza virus M2-specific antibody responses were also maintained at higher levels than that of M2WT VLPs (FIG. 7B) for over 8 months, indicating that M2 immunity can be long-lived. To assess the long-term protective efficacy, groups of mice that were intramuscularly immunized with TL-M2e5x or M2WT VLPs were challenged with a lethal dose of A/Philippines/82 (FIG. 7C, 7D) at 8 months after vaccination. Mice that were immunized with TL-M2e5x VLPs (10 µg of total protein) using a prime boost regimen were 100% protected without significant weight loss (FIG. 7C, 7D). However a group of mice that was immunized with M2WT VLPs (10 µg of total protein) was only 33% protected, and accompanied by severe weight loss up to 22% in surviving mice (FIG. 7D). These results indicate that TL-M2e5x VLP vaccines are more effective in inducing long-lasting protection against mortality as well as morbidity after intramuscular immunization.

Figure 8A:
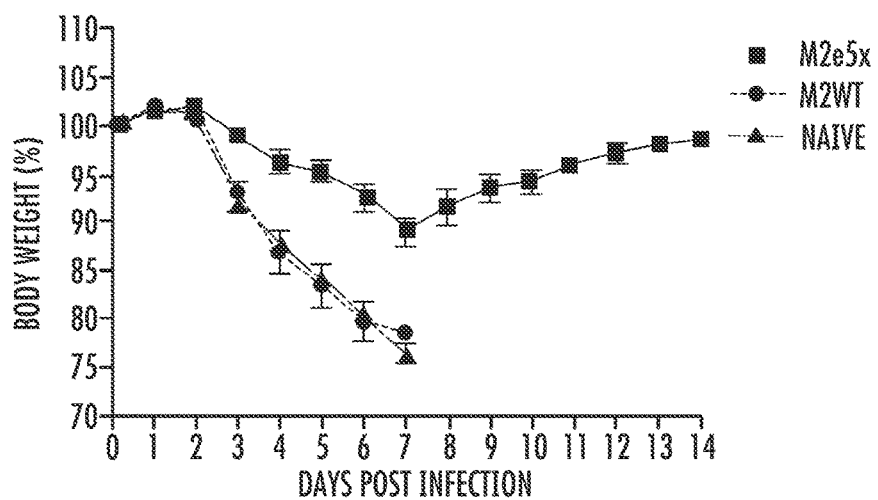
FIGS. 8A to 8D show that TL-M2e5x VLP immune sera confer protection to naïve mice.
Figure 8B:
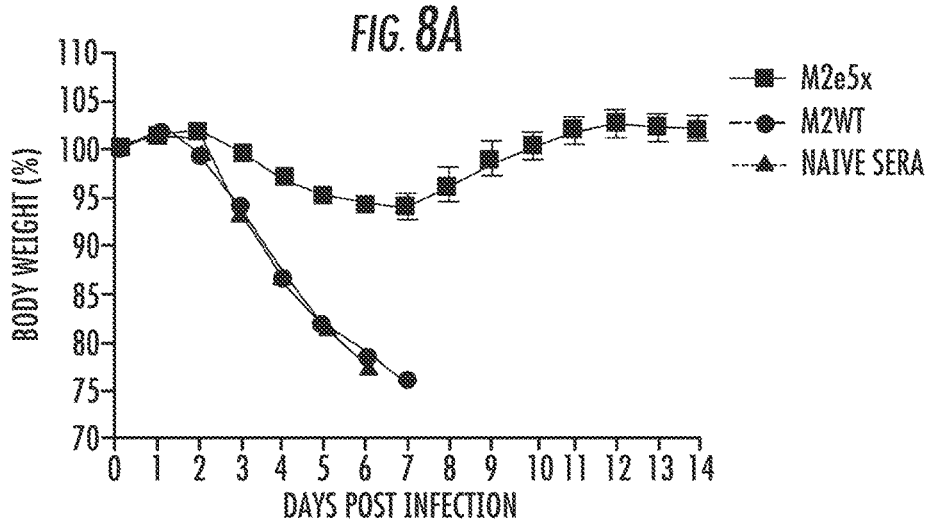
Figure 8C:
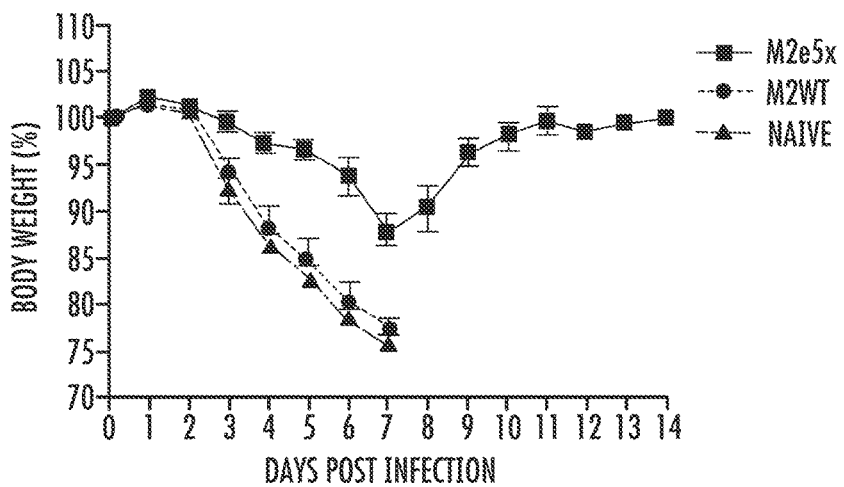
Figure 8D:
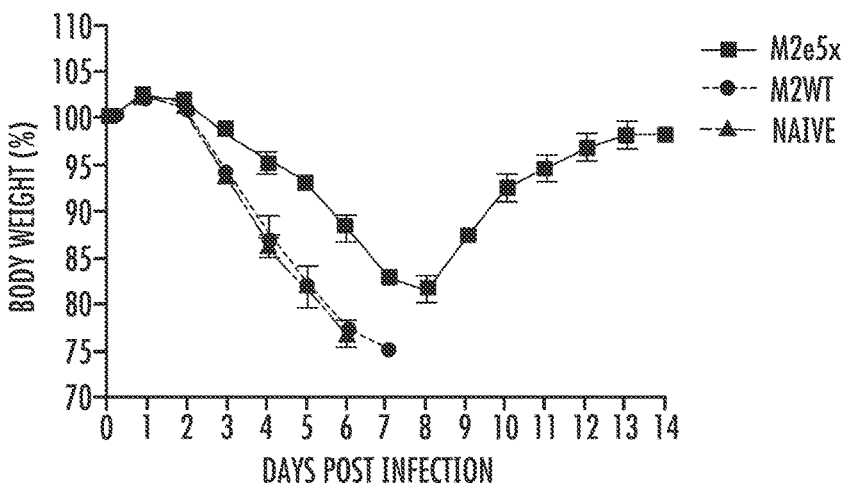

Example 9: TL-M2e5x VLP Immune Sera Play an Important Role in Conferring Protection Results To further determine the protective role of anti-M2e5x or M2WT immune sera, an in vivo protection assay was conducted. Naïve mice were infected with a mixture of immune sera and a lethal dose of different strains of influenza A virus. Immune sera collected at different time points 3 weeks (FIG. 8A, 8B) or 8 months (FIG. 8C, 8D) were used to assess the cross protective effect of M2 immune sera. In addition, to test the breadth of cross-protection, the protection studies were extended to the following viruses: A/Vietnam/1203/2004 (H5N1) reassortant virus and A/PR8/34 (H1N1). Naïve mouse sera and M2WT VLP immune sera did not confer any protection to mice (FIGS. 8A-8D). In contrast, TL-M2e5x VLP immune sera provided 100% protection to naive mice that were infected with a lethal dose of A/PR/8/34 (H1N1) (FIG. 8A) or A/Vietnam/1203/2004 (H5N1) reassortant virus (FIG. 8B). Low levels of morbidity (5-10% weight loss) were observed in protected mice. With sera from TL-M2e5x VLP immunized mice collected at 8 months after boost, naïve mice were 100% protected against A/PR/8/34 (H1N1) (FIG. 8C) or reassortant A/Vietnam/1203/2004 (H5N1) virus (FIG. 8D). Body weight loss was in the range of 10-18% depending on the virus strain used for infection, implying that these surviving mice experienced more morbidity compared to those treated with TL-M2e5x VLP immune sera collected at 3 weeks after boost (FIG. 8A, 8B). Nonetheless, these results further support the evidence that TL-M2e5x VLP vaccination can induce antibody responses which confer long-term protective immunity to different subtypes of influenza viruses. Therefore, VLPs with a tandem repeat of M2e sequences from multiple strains are a promising universal vaccine candidate compared to the wild type M2 VLP vaccine.

Figure 9A:
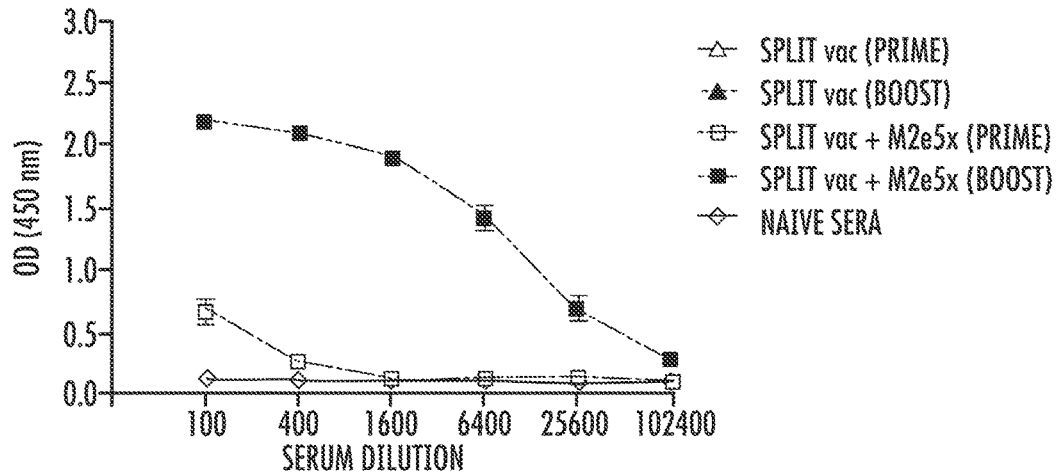
FIGS. 9A and 9B are graphs showing M2e specific antibody (FIG. 9A) and antibody responses to 2009 pandemic influenza virus (FIG. 9B) in mice that were immunized with commercial human split vaccine (2009 H1N1 monovalent) supplemented with newly developed TL-M2e5x VLPs via intramuscular immunization. Supplemented vaccines (Split Vac+TL-M2e5x) showed high levels of antibodies specific to both 2009 pandemic influenza virus vaccine antigen and M2e as a conserved epitope. Split vac+TL-M2e5x: supplemented vaccines of commercial human 2009 H1N1 monomeric influenza vaccine (Novartis) plus TL-M2e5x VLPs, Split vac: commercial human 2009 H1N1 monomeric influenza vaccine only. Naïve: unimmunized mice.
Figure 9B:
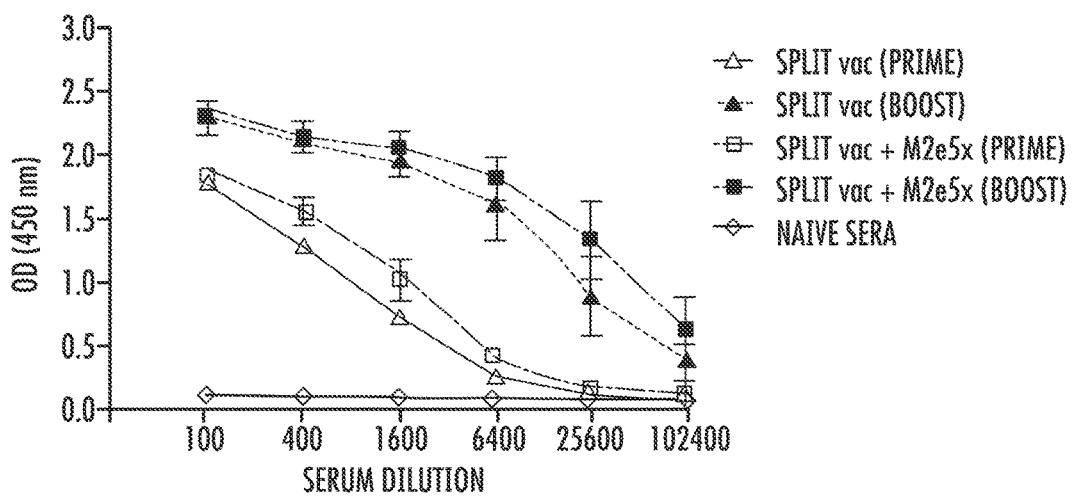

Example 10: Supplementing with TL-M2e5x VLP Vaccine Increases M2e Immunity of Human Influenza Vaccines Results A new concept for overcoming strain-specific protection of current influenza vaccines was examined by supplementing with VLPs of the wild type M2 protein, a highly conserved epitope (Song, J. M., et al. 2011. Proc Natl Acad Sci USA 108:757-761). The amounts of M2e epitopes in the newly developed TL-M2e5x VLP vaccine were found to be several hundred-folds higher than those in the M2 wild type VLPs. To extend this concept of overcoming strain-specific protection of current influenza vaccines, commercial human split vaccine (2009 H1N1 monovalent) was supplemented with newly developed TL-M2e5x VLPs. Groups of mice were intramuscularly immunized with split vaccine alone or supplemented vaccine (split human vaccine+TL-M2e5x VLPs) by a prime-boost regimen (FIG. 9). The human vaccine (Split vac, commercial human split vaccine) alone immunized group of mice showed a high level of antibodies binding to the vaccine strain specific HA antigen (FIG. 9B). However, the human vaccine alone group did not induce any levels of antibodies recognizing the conserved M2e antigen (FIG. 9A). The TL-M2e5x VLP supplemented human split vaccination induced high levels of antibodies binding to both the M2e antigen and the influenza vaccine antigen. Therefore, supplementing human vaccine with TL-M2e5x VLPs induces antibodies reactive to the conserved antigen M2 as well as the influenza viral antigens relating to the vaccine.

Figure 10A:
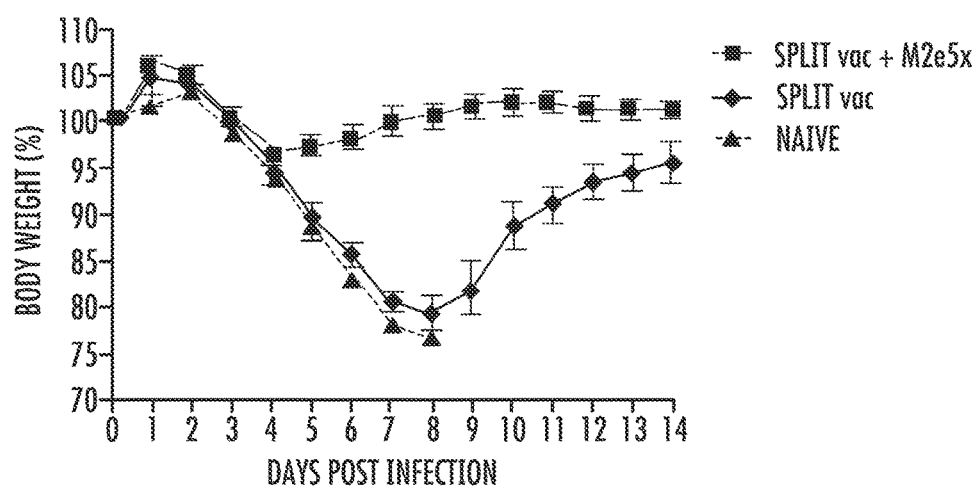
FIGS. 10A to 10D show body weight changes (FIG. 10A, 10C) and survival rates (FIG. 10B, 10D) after challenge with a lethal dose of A/Philippines/2/82 H3N2 virus (FIG. 10A, 10B) or with reassortant A/Vietnam/1203/2004, avian derived influenza A H5N1 virus (FIG. 10C, 10D). Splic vac+TL-M2e5x: supplemented vaccines of commercial human 2009 H1N1 monomeric influenza vaccine (Novartis) plus TL-M2e5x VLPs, Split vac: commercial human 2009 H1N1 monomeric influenza vaccine only.
Figure 10B:
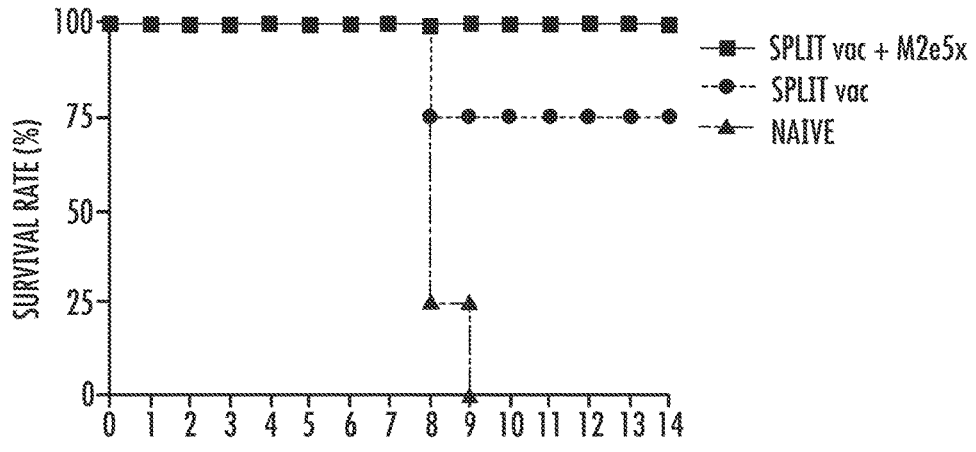
Figure 10C:
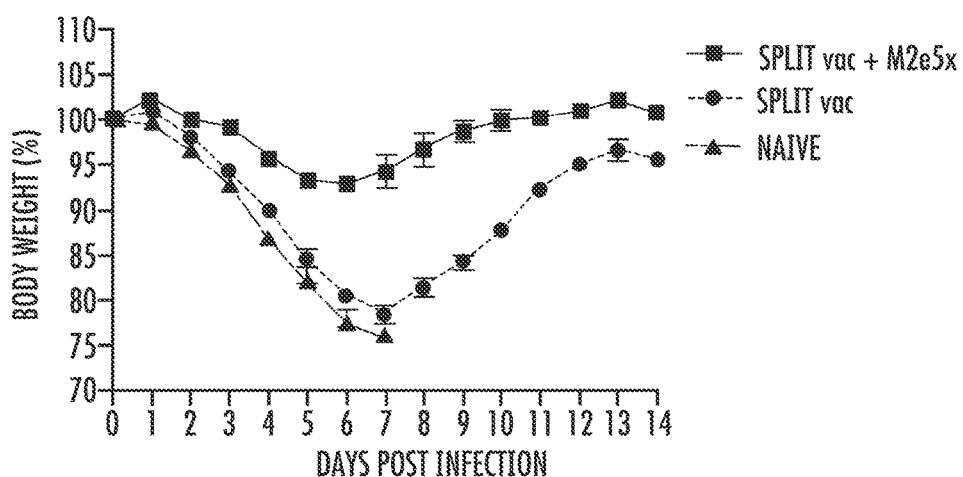
Figure 10D:
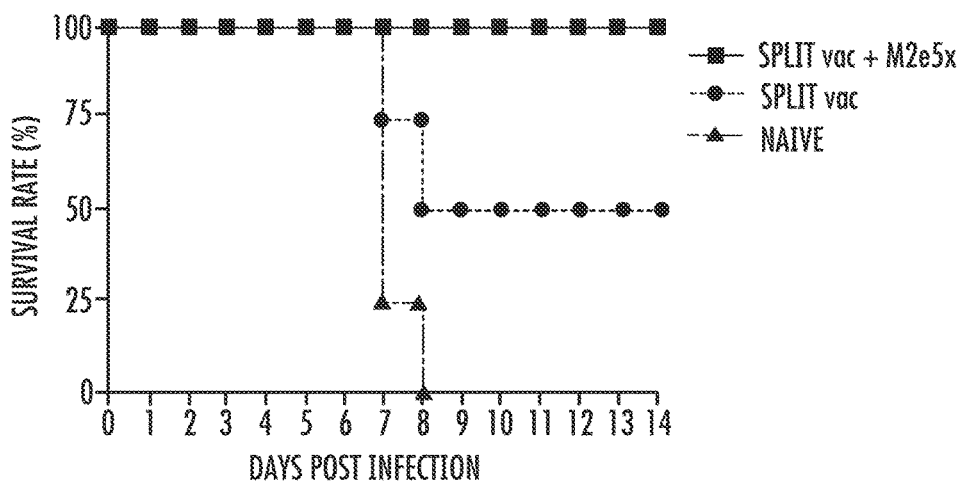

Example 11: Supplementing TL-M2e5x VLP Vaccines Significantly Enhanced the Cross Protective Efficacy of Human Influenza Vaccines Results To determine the efficacy of heterosubtypic cross protection, groups of mice were immunized with human split vaccine alone (Split Vac, FIG. 10) or supplemented vaccines containing both human split vaccine and TL-M2e5x VLPs (Split Vac+TL-M2e5x, FIG. 10). After 6 weeks post boost vaccination, these immunized mice were challenged with a lethal dose of H3N2 A/Philippines/82 virus. Split H1N1 vaccine (2009 pandemic virus) alone was not effective in preventing weight losses against lethal challenge with the different subtypic H3N2 A/Philippines/82 virus (FIG. 10A). In contrast, the TL-M2e5x VLP supplemented vaccine group (Split Vac+TL-M2e5x, FIG. 10A, 10B) showed significantly improved protection preventing weight loss and 100% mice in this supplemented group were protected.

Figure 11A:
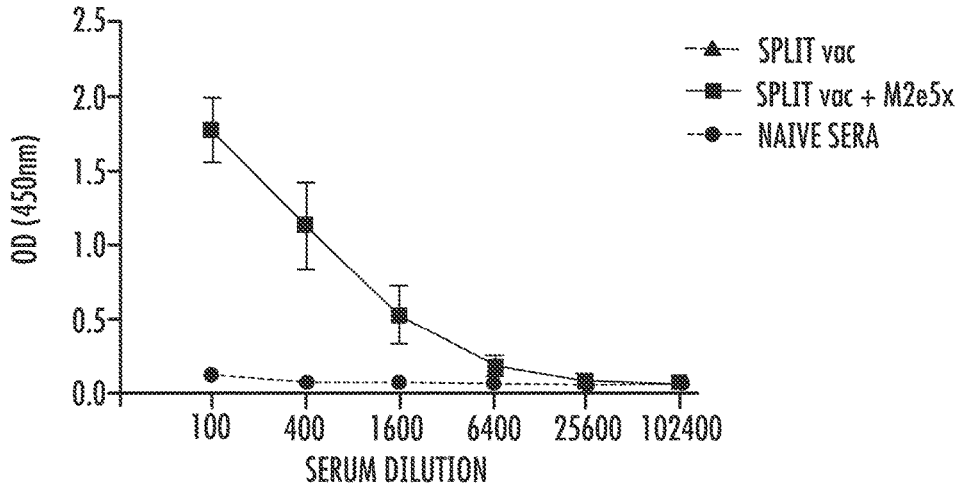
FIGS. 11A and 11B are graphs showing M2e specific antibody responses (FIG. 11A) or Vaccine (2009 pandemic virus) specific antibody responses (FIG. 11B) of immune sera after 12 months of supplemented vaccination (Split vac+TL-M2e5x).
Figure 11B:
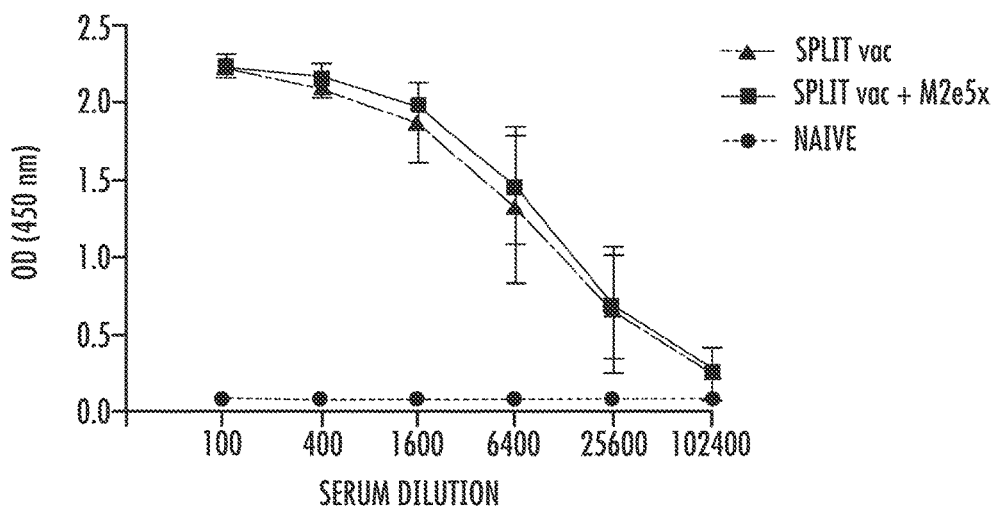

To further extend this improved cross protection against a different subtype virus, TL-M2e5x VLP vaccinated mice were challenged with a lethal dose of an avian subtype H5N1 virus (A/Vietnam/1203). The vaccine only group showed a severe weight loss similar to unvaccinated naïve mice and only a partial protection was observed. As expected, the TL-M2e5x VLP supplemented vaccination group prevented weight loss and all mice were protected from lethal infection. Therefore, supplementing commercial human vaccines with TL-M2e5x VLPs significantly enhances the cross protective efficacy of human influenza vaccines Example 12: TL-M2e5x VLP Supplemented Human Vaccine (2009 Pandemic Vaccine) Confers Long-Term (12 Months) Cross Protection Results Because of low immunogenicity of M2 antigen, inducing M2 specific long-term immunity has been a challenging difficulty in the influenza vaccine field. To determine whether TL-M2e5x VLP supplemented vaccination would induce long-lasting M2 immunity, serum antibody responses specific to M2e specific were determined in mice that had been immunized with TL-M2e5x VLP-supplemented commercial human vaccine (Split vac+TL-M2e5x) or human vaccine alone (Split Vac) 12 months earlier. High levels of M2e specific antibodies as well as influenza vaccine antigen binding antibodies were maintained in the supplemented vaccination group for over 12 months (FIG. 11A, 11B).

Figure 11C:
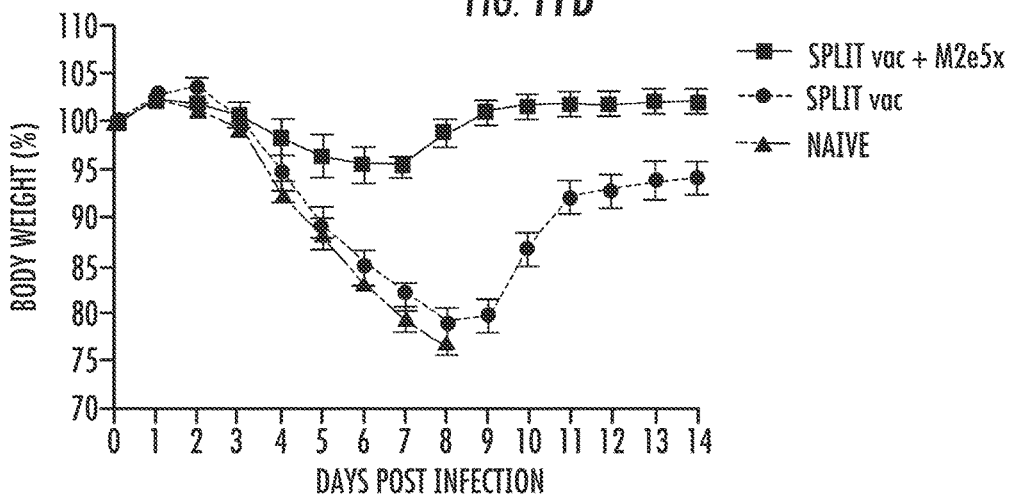
FIGS. 11C and 11D are graphs showing bBody weight changes (FIG. 11C) and survival rates (FIG. 11D) after challenge with a lethal dose of A/Philippines/2/82, H3N2 virus. Splic vac+TL-M2e5x: supplemented vaccines of commercial human 2009 H1N1 monomeric influenza vaccine (Novartis) plus TL-M2e5xVLPs, Split vac: commercial human 2009 H1N1 monomeric influenza vaccine only.
Figure 11D:
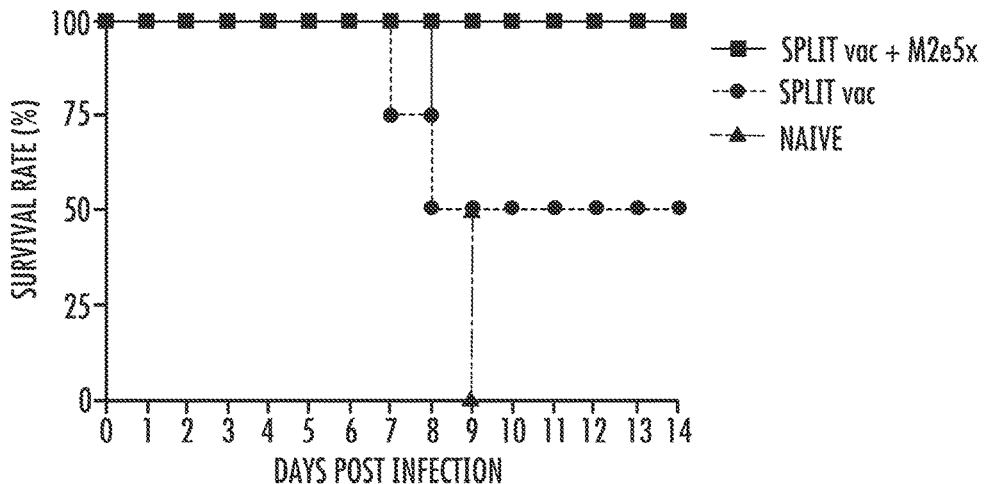

Development of vaccines inducing long-term cross protection is highly desirable. After 12 months of TL-M2e5x VLP supplemented vaccination, a lethal dose of heterosubtypic challenge virus (A/Philippines/2/82, H3N2 virus) was used to infect vaccinated mice (FIG. 11C, 11D). The TL-M2e5x supplemented group of mice showed significantly improved cross protection after 12 months of vaccination compared to the vaccine only group (FIG. 11C, 11D).

Example 13: Skin Vaccination of TL-M2e5x VLP Supplemented Commercial Human Vaccine (2009 Pandemic Virus) Enhanced Cross Protection Results Hypodermic needle injection is associated with low coverage of vaccination, pains, requirement of medical personnel, and needle-injuries. Therefore, needle-free vaccine delivery is highly desirable for enabling mass vaccination easy. Skin vaccination with inactivated whole virus vaccines or influenza VLP vaccines using solid microneedles induces equivalent or better protective immune responses (Quan, F. S., et al. 2010. Journal of controlled release: official journal of the Controlled Release Society 147:326-332; Quan, F. S., et al. 2010. J Virol 84:7760-7769; Song, J. M., et al. 2010. Clin Vaccine Immunol 17:1381-1389). In particular, testing skin vaccination with universal influenza vaccines has its significance. But, universal influenza vaccine candidates had not been tested.

Figure 12A:
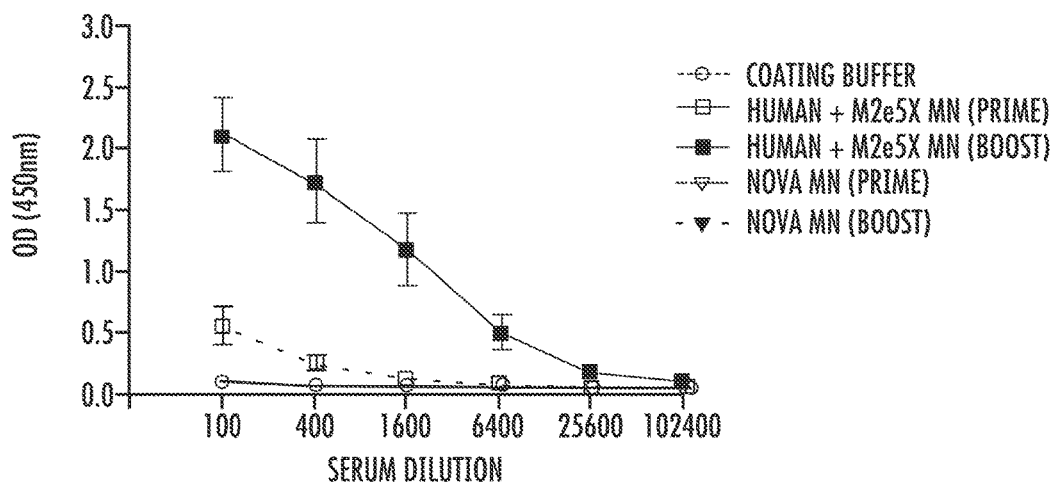
FIGS. 12A and 12B are graphs showing M2e specific antibody responses (FIG. 12A) or Vaccine (2009 pandemic virus) specific antibody responses (FIG. 12B) of immune sera after microneedle skin vaccination of supplemented vaccines (Split vac+TL-M2e5x) of commercial human 2009 H1N1 monomeric influenza vaccine (Novartis) plus TL-M2e5x VLPs.
Figure 12B:
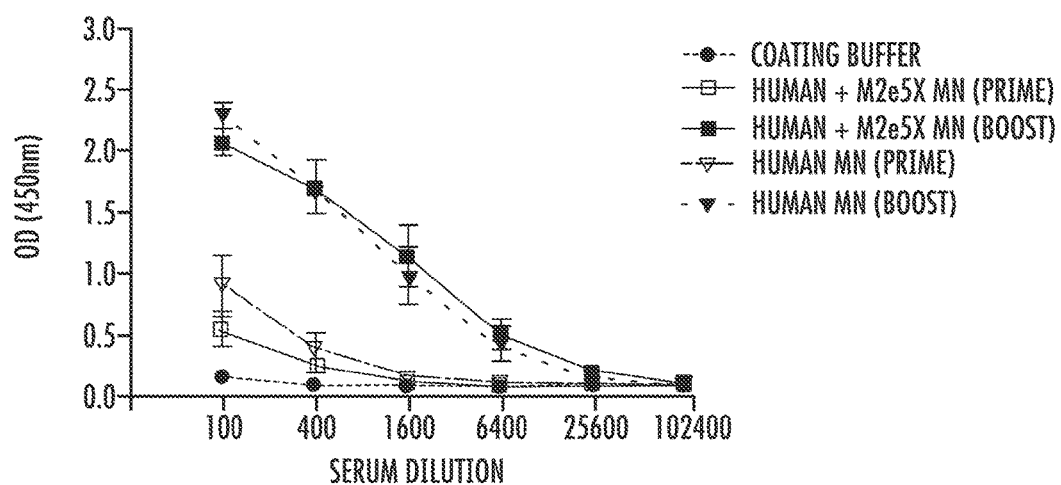

Groups of mice were immunized on the skin via microneedle skin vaccination of supplemented vaccines (Split vac+TL-M2e5x) of commercial human 2009 H1N1 monomeric influenza vaccine (Novartis) plus TL-M2e5x VLPs. After prime boost skin vaccination of mice, serum antibodies specific to M2e peptide antigen were determined (FIG. 12A). TL-M2e5x VLP supplemented skin vaccination (Human+M2e5x MN) induced high levels of antibodies specific to M2e antigens as well as whole viral antigens (FIG. 12A, 12B). Vaccine only group induced antibodies reactive to the viral HA antigen but not to an M2e antigen.

Figure 12C:
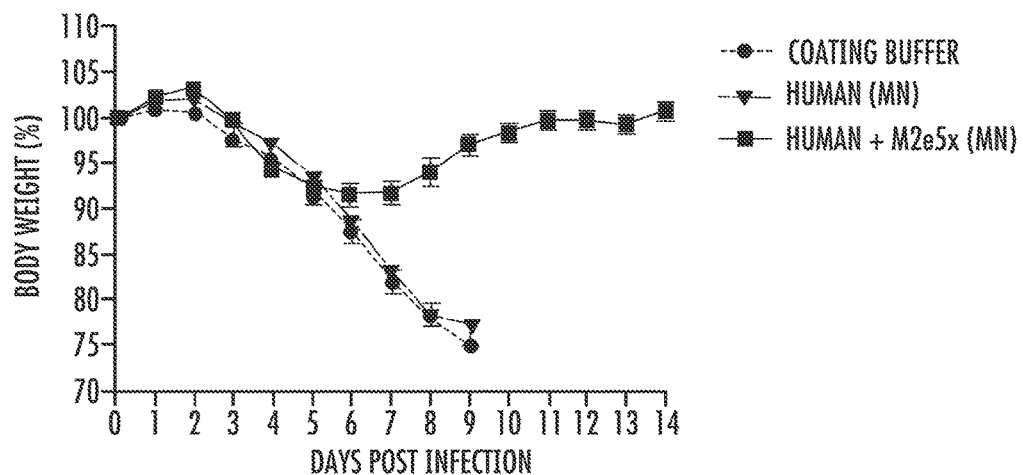
FIGS. 12C and 12D are graphs showing body weight changes (FIG. 12C) or survival rates (FIG. 12D) after challenge with A/Philippines/2/82, H3N2 virus. Splic vac+TL-M2e5x: supplemented vaccines of commercial human 2009 H1N1 monomeric influenza vaccine (Novartis) plus TL-M2e5x VLPs, Split vac: commercial human 2009 monomeric influenza vaccine only.
Figure 12D:
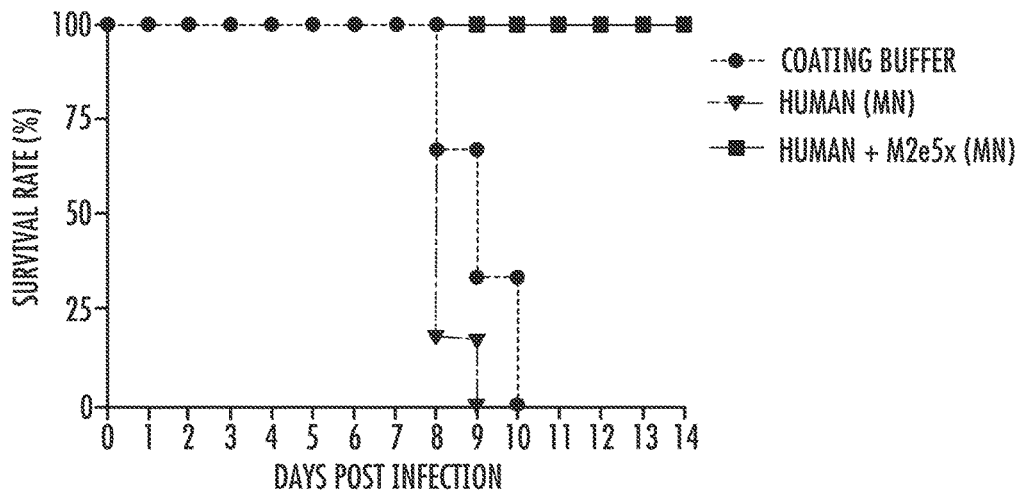

To determine cross protection, these skin vaccinated mice were challenged with a lethal dose of A/Philippines/2/82, H3N2 virus, and then body weight changes and survival rates were monitored daily for 14 days. The group of mice that were skin-immunized with human vaccine only coated microneedles (Human (MN), FIG. 12C) was not protected against a different subtype virus, all mice lost body weight significantly and had to be euthanized. This supports the general concept that current human vaccines based on HA immunity is not protective to an antigenically different influenza virus. In the group of mice that were supplemented with universal influenza vaccine TL-M2e5x VLPs, only moderate levels of weight loss and 100% mice were protected (Human+M2e5x (MN), FIG. 12C). Supplementing with TL-M2e5x VLP vaccine was required for cross protection.

Figure 13A:
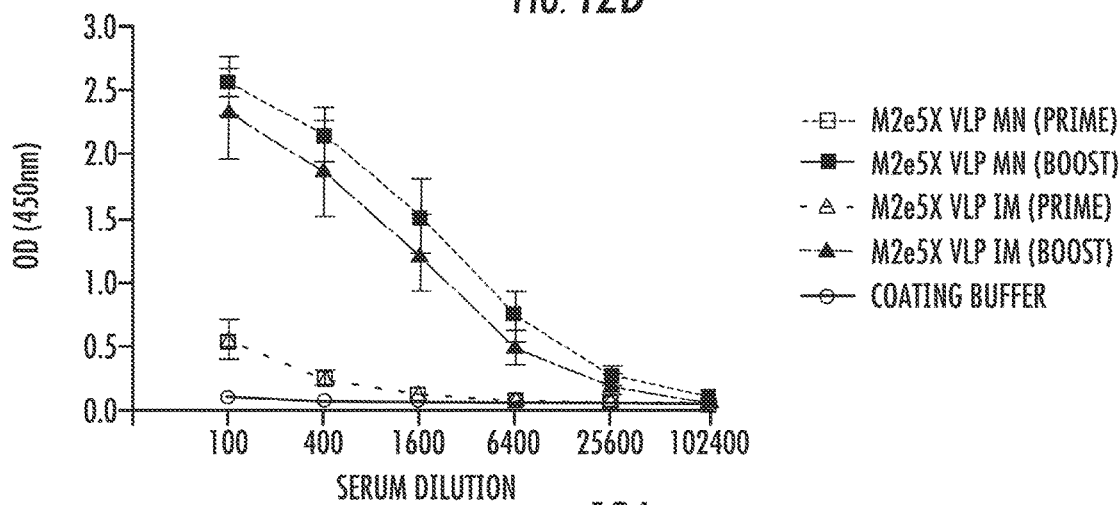
FIG. 13A is a graph showing M2e specific antibody responses of immune sera after microneedle skin vaccination or conventional intramuscular injection with TL-M2e5x VLP universal vaccine.
Figure 13B:
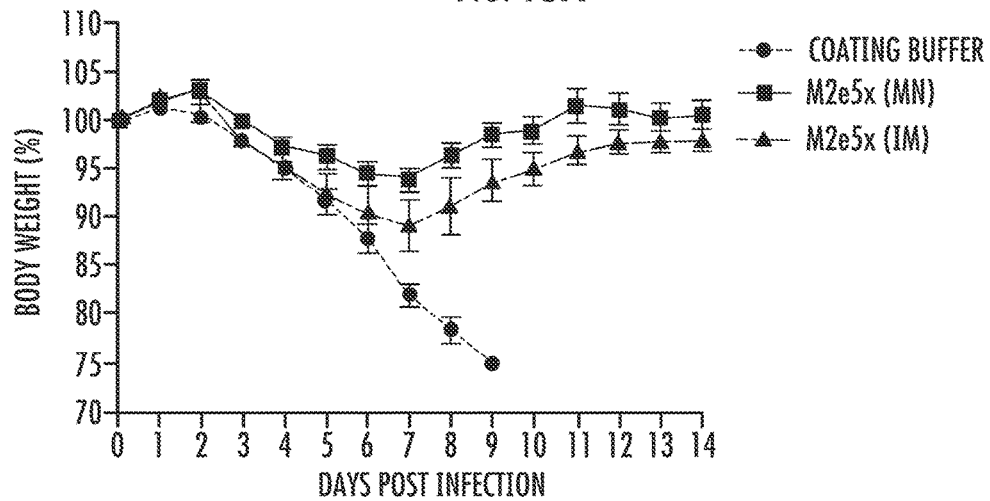
FIGS. 13B and 13C are graphs showing body weight changes (FIG. 13B) or survival rates (FIG. 13C) after challenge with A/Philippines/2/82, H3N2 virus. TL-M2e5x (IM): TL-M2e5x VLP vaccine was intramuscularly injected to mice. TL-M2e5x (MN): TL-M2e5x VLP vaccine was vaccinated on the skin using microneedles (MN). Coating buffer: Mice were immunized on the skin using mock microneedles without TL-M2e5x vaccine.
Figure 13C:
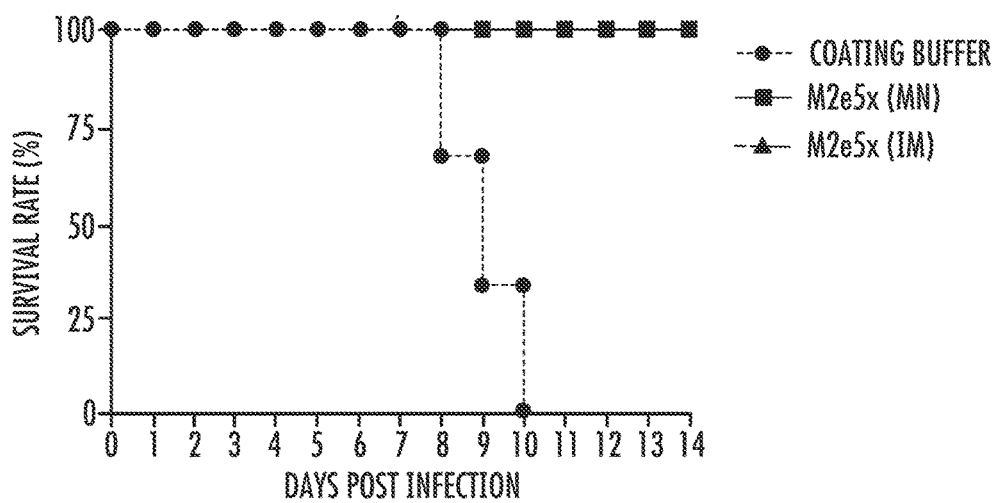

Example 14: Microneedle Skin Vaccination with TL-M2e5x VLP Vaccine Induced Comparable or Better Cross Protection Compared to Conventional Intramuscular Injection Results It is important to determine whether skin vaccination with TL-M2e5x VLP vaccines would induce comparable or better protection compared to conventional needle injection (FIG. 13). The induction of M2e specific antibody responses in mice after vaccination with TL-M2e5x VLPs (5 µg) either in the skin using microneedles (M2e5x(MN)) or intramuscular needle injection (M2e5x(IM, intramuscular) (FIG. 13) was examined. Microneedle skin vaccination of mice induced comparable or higher levels of antibodies specific to M2e antigens compared to those by conventional intramuscular immunization (FIG. 13A). To determine the efficacy of cross protection, these mice that were vaccinated with TL-M2e5x VLPs in the skin or muscle were subjected to lethal dose challenge with H3N2 virus, A/Philippines/2/82 (FIG. 13B, 13C). The group of mice with TL-M2e5x VLP skin immunization showed a trend of less weight loss compared to that with intramuscular immunization. Therefore, TL-M2e5x VLP vaccines can be delivered to the skin for vaccination using solid microneedles.

Example 15: TL-M2e5x VLP Vaccines are Highly Effective Even in the Presence of Pre-Existing Immunity Results Human populations are highly heterogeneous in terms of immunity to influenza virus probably due to previous exposures or vaccinations. Therefore, it is significant to determine whether TL-M2e5x VLP vaccines would be effective in inducing cross protection in the presence of pre-existing immunity to influenza. To induce pre-existing immunity, groups of mice were immunized with commercial human vaccines in advance (4 weeks earlier) before TL-M2e5x VLP vaccination. After 4 weeks of immunization with commercial human vaccine, a group of mice was intramuscularly immunized with TL-M2e5x VLPs. To determine the cross protective efficacy of TL-M2e5x VLP immunization later in the presence of immunity to human vaccines, an antigenically different H3N2 subtype of influenza virus A/Philippines/2/82 was used to do lethal challenge. The group of mice that were immunized with TL-M2e5x showed less body weight loss and 100% protection against a lethal dose of A/Philippines/2/82 H3N2 virus (FIG. 14A, B: Split Vac+TL-M2e5x VLP). However, the group of mice that were immunized with commercial human vaccine (2009

Figure 14A:
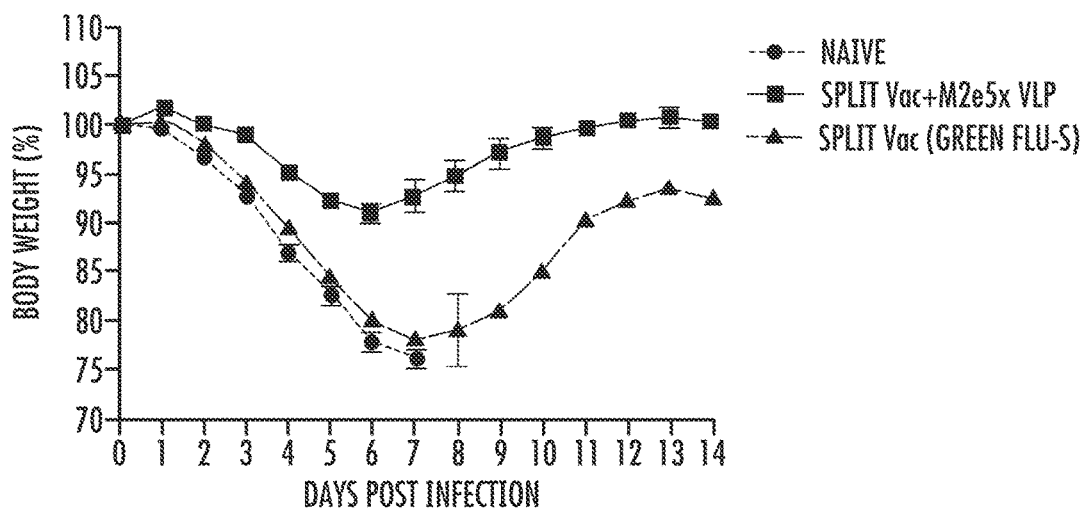
FIGS. 14A and 14B are graphs showing body weight changes (FIG. 14A) and survival rates (FIG. 14B) after challenge with a lethal dose of A/Philippines/2/82, H3N2 virus. Naïve: unvaccinated mice. Split Vac (Green Flu-S) (Green Cross Co. Ltd.): human commercial vaccine (2009 pandemic virus monomeric vaccine) was used to immunize a group of mice intramuscularly to induce pre-existing immunity. After vaccination with 2009 pandemic virus vaccine, there was no TL-M2e5x VLP vaccination. Split Vac+TL-M2e5x VLP: After vaccination of mice with 2009 pandemic virus vaccine, TL-M2e5x VLP universal vaccine was used to intramuscularly immunize the mice that had received human vaccine (2009 pandemic virus monomeric vaccine) 4 weeks earlier.
Figure 14B:
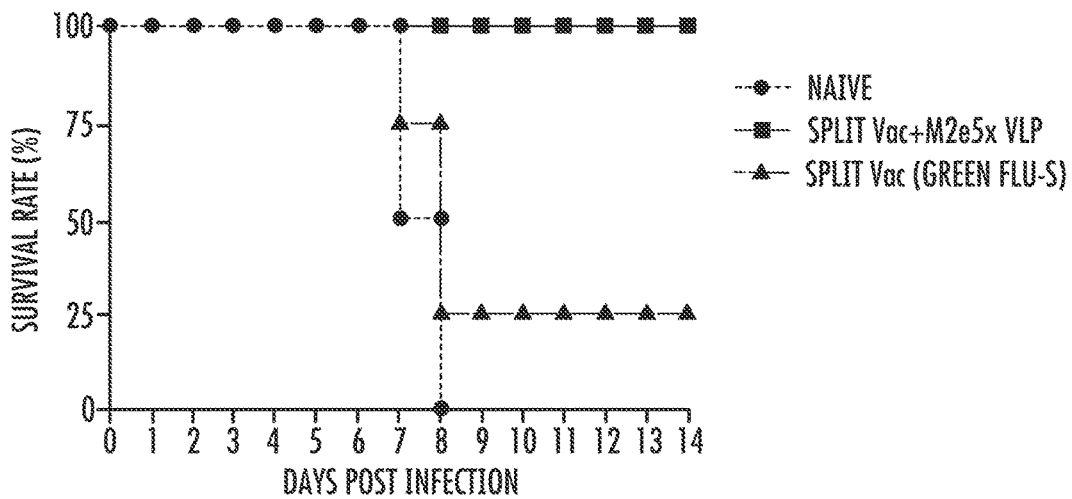

H1N1 influenza vaccine) exhibited severe weight loss similar to that observed in the unvaccinated mice after challenge with a lethal dose of A/Philippines/2/82 H3N2 virus (FIG. 14A). Also, only 25% partial survival protection was observed in the mice that were not later vaccinated TL-M2e5x VLPs (Split Vac (Green Flu-S), FIG. 14A, 14B).

Example 16: M2e5x Vaccine Construct with and without Toll-Like Receptor Ligand (TL)

Figure 15A:
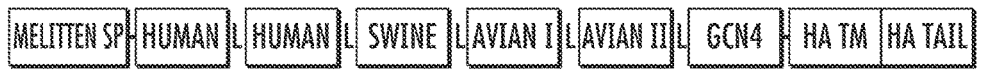
FIGS. 15A and 15B are schematics of M2e5x VLP (FIG. 15A) and TL-M2e5x VLP (FIG. 15B) constructs.
Figure 15B:
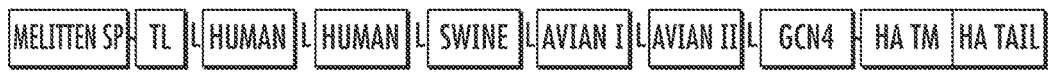

To determine the effect of Toll-like receptor ligand (TL), VLP constructs with (TL-M2e5x VLP) and without (M2e5x VLP) a TL domain were compared (FIG. 15). Unexpectedly, M2e5x VLP was highly effective in stimulating the production of M2e specific antibody responses compared to TL-M2e5x VLP.

Materials
Cells, Viruses, and Reagents
*Spodoptera frugiperda* sf9 insect cells (ATCC, CRL-1711) were maintained in SF900-II serum free medium (Invitrogen, Carlsbad, Calif.) at 27° C. and used for production of recombinant baculoviruses (rBVs) and VLPs. A gene fragment encoding for Toll-like receptor ligand (TL) contained the TL sequence INNNLQRVRELAVQSANS (SEQ ID NO:22) and the linker AAPGAA (SEQ ID NO:23). This gene fragment was inserted between the restriction enzyme sites SpeI and SalI in the M2e5x VLP construct.

The TL-M2e5x VLP had the following amino acid sequence:

```
                                           (SEQ ID NO: 24)
MKFLVNVALVFMVVYISYIYADPINMTTSINNNLQRVRELAVQSANSAAA

PGAAVDGTSLLTEVETPTRNEWESRSSDSSDAAAGGAASLLTEVETPTRN

EWESRSSDSSDAAAPGAASLLTEVETPTRHEWESRSSDSSDAAAGGAASL

LTEVETPTRHEWESRSSDSSDAAAPGAASLLTEVETPTRNGWKCKCSDSS

DGGLKQIEDKLEEILSKLYHIENELARIKKLLGELEILAIYSTVASSLVL

LVSLGAISFWMCSNGSLQCRICI.
```

The TL-M2e5x VLP was encoded by the following nucleic acid sequence:

```
                                           (SEQ ID NO: 25)
ATGAAGTTTCTGGTGAACGTTGCCCTGGTTTTTATGGTTGTTTACATTTC

CTACATTTACGCTGACCCGATTAACATGACGACTAGTATTAACAATAACC

TGCAGCGTGTCCGCGAACTGGCCGTGCAAAGTGCAAATTCCGCAGCAGCA

CCGGGTGCTGCAGTCGACGGTACCAGCCTGCTGACGGAAGTCGAAACCCC

GACGCGTAACGAATGGGAATCTCGCAGCTCTGATAGTTCCGACGCAGCAG

CTGGCGGTGCAGCCAGTCTGCTGACCGAAGTGGAAACCCCGACGCGTAAT

GAATGGGAATCCCGCTCATCGGATAGCTCTGACGCAGCTGCACCGGGTGC

AGCATCACTGCTGACGGAAGTTGAAACCCCGACGCGTCATGAATGGGAAT

CGCGCAGTTCCGATTCATCGGACGCTGCAGCCGGCGGTGCAGCCAGCCTG

CTGACCGAAGTTGAAACGCCGACCCGTCATGAATGGGAAAGCCGTTCTAG

CGACAGTTCCGATGCCGCAGCACCGGGTGCTGCGAGCCTGCTGACCGAAG

TCGAAACGCCGACGCGTAATGGTTGGAAATGCAAGTGTAGCGATTCATCG

GACGGCGGTCTGAAACAGATTGAAGATAAGCTGGAAGAAATCCTGAGTAA
```

-continued
```
ACTGTACCATATCGAAAACGAACTGGCGCGCATCAAAAAGCTGCTGGGCG

AACTCGAGATTCTGGCCATCTACTCAACCGTGGCGAGCTCTCTGGTGCTG

CTGGTTTCGCTGGGTGCAATCTCCTTCTGGATGTGTTCTAACGGTTCCCT

GCAATGTCGTATCTGTATC.
```

Comparison of Immunogenicity Between M2e5x VLP and TL-M2e5x VLP.

Figure 15C:
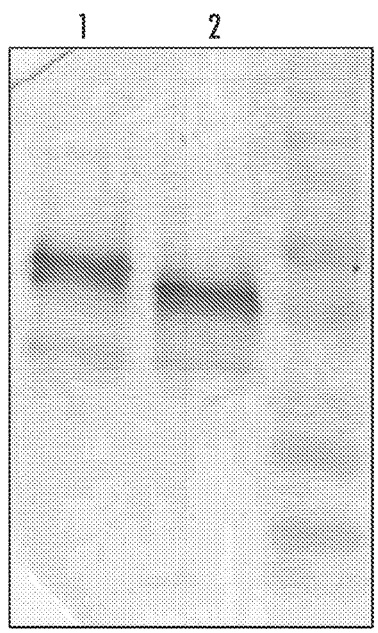
FIG. 15C is a Western blot for M2e5x protein using the M2e5x VLP (lane 2) and TL-M2e5x VLP (lane 1) constructs.

In western blot result, M2e reactivity to M2e monoclonal antibody (14C2) was similar between M2e5x VLP and TL-M2e5x VLP (FIG. 15C). To compare immunogenicity, the concentration of VLPs was reduced to 2 μg and the mice were vaccinated via the intramuscular route. Blood was taken at 3 weeks after each prime, boost and re-boost vaccination to check antibody response using human type M2e peptide.

Results

Figure 16:
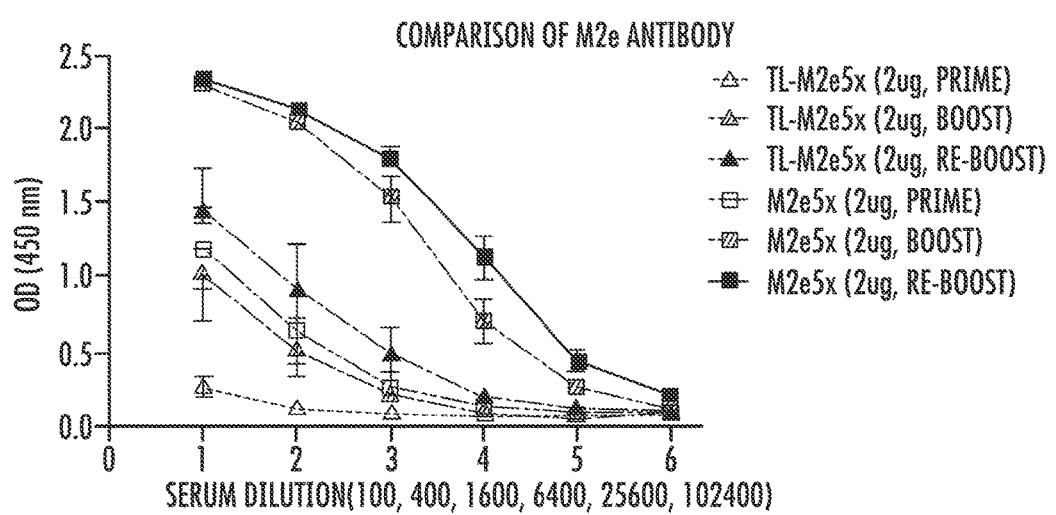
FIG. 16 is a graph showing M2e antibody concentration (OD 450 nm) as function of serum dilution (100, 400, 1600, 6400, 25600, and 102400) after induction with M2e5x (squares) or TL-M2e5x (triangles) VLPs.

Optical density (OD) value to human type M2e peptide was compared between M2e5x VLP and TL-M2e5x VLP using low level (2 μg) of VLPs. After prime vaccination, mice vaccinated with M2e5x VLP showed approximately 16 fold higher OD values than the mice that were vaccinated with TL-M2e5x VLP based on serum dilution factors giving similar OD values (FIG. 16). After boost or re-boost vaccination, M2e antibody was detected at approximately 64 fold higher levels from mice that were vaccinated with M2e5x VLP comparing to mice vaccinated with TL-M2e5x VLP (based on serum dilution factors giving similar OD values). These results showed that M2e5x VLP was more immunogenic and effective in producing M2e antibodies than TL-M2e5x VLP at least 16 to 64 times. Therefore, it is likely that the presence of Toll-like receptor ligand (TL) in the TL-M2e5x VLP might be blocking the exposure of M2e epitopes to the immune system. Removing this structural hindrance in the M2e5x VLP may have better exposed the M2e epitopes more favorably to the immune system, thus producing higher levels of M2e antibodies after immunization of mice (FIG. 16).

Figure 17A:
FIGS. 17A and 17B are schematics of two monomeric vectors (FIG. 17A) or a dual expression vector (FIG. 17B) for M2e5x vaccine production.
Figure 17B:
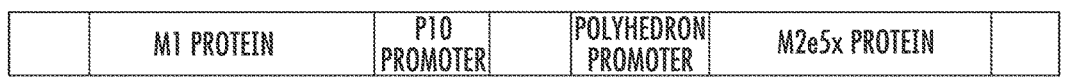

Example 17: Construction of a Dual Vector for the Production of M2e5x VLP Vaccines Materials and Methods
Cells, Viruses, and Reagents
*Spodoptera frugiperda* sf9 insect cells (ATCC, CRL-1711) were maintained in SF900-II serum free medium (Invitrogen, Carlsbad, Calif.) at 27° C. and used for production of recombinant baculoviruses (rBVs) and VLPs. In this study, pFastBac dual vector was used to make one baculovirus expressing both M2e5x surface protein and M1 inner core protein. Gene for M1 protein was from A/PR/2/82 influenza virus and amplified using PCR. The amplified M1 product was inserted into a region under the p10 promoter (FIG. 17A) and M2e5x protein expressing gene domain was inserted into a region under the polyhedron promoter, respectively (FIG. 17B).

The M1 nucleic acid sequence is as follows:

```
                                           (SEQ ID NO: 26)
GCCGCCACCATGAGTCTTCTAACCGAGGTCGAAACGTACGTTCTCTCTAT

CATCCCGTCAGGCCCCCTCAAAGCCGAGATCGCACAGAGACTTGAAGATG

TCTTTGCAGGGAAGAACACCGATCTTGAGGTTCTCATGGAATGGCTAAAG
```

-continued

```
ACAAGACCAATCCTGTCACCTCTGACTAAGGGGATTTTAGGATTTGTGTT

CACGCTCACCGTGCCCAGTGAGCGAGGACTACAGCGTAGACGCTTTGTCC

AAAATGCCCTTAATGGGAACGGCGATCCAAATAACATGGACAAAGCAGTT

AAACTGTATAGGAAGCTCAAGAGGGAGATAACATTTCATGGGCCAAAGA

AATCTCACTCAGTTATTCTGCTGGTGCACTTGCCAGTTGTATGGCCTCA

TATACAACAGGATGGGGCTGTGACCACTGAAGTGGCATTTGGCCTGGTA

TGTGCAACCTGTGAACAGATTGCTGACTCCCAGCATCGGTCTCATAGGCA

AATGGTGACAACAACCAACCCACTAATCAGACATGAGAACAGAATGGTTT

TAGCCAGCACTACAGCTAAGGCTATGGAGCAAATGGCTGGATCGAGTGAG

CAAGCAGCAGAGGCTATGGAGGTTGCTAGTCAGGCTAGGCAAATGGTGCA

AGCGATGAGAACCATTGGGACTCATCCTAGCTCCAGTGCTGGTCTGAAAA

ATGATCTTCTTGAAAATTTGCAGGCCTATCAGAAACGAATGGGGGTGCAG

ATGCAACGGTTCAAGTGATGA.
```

The M1 amino acid sequence (M1 from A/PR/8/43, H1N1) is as follows:

(SEQ ID NO: 27)
```
MSLLTEVETYVLSIIPSGPLKAEIAQRLEDVFAGKNTDLEVLMEWLKTRP

ILSPLTKGILGFVFTLTVPSERGLQRRRFVQNALNGNGDPNNMDKAVKLY

RKLKREITFHGAKEISLSYSAGALASCMGLIYNRMGAVTTEVAFGLVCAT

CEQIADSQHRSHRQMVTTTNPLIRHENRMVLASTTAKAMEQMAGSSEQAA

EAMEVASQARQMVQAMRTIGTHPSSSAGLKNDLLENLQAYQKRMGVQMQR

FK.
```

Preparation of Dual Vector-Expressed M2e5x VLP Vaccines

The M2e5x gene and M1 gene were cloned into polyhedron promoter and p10 promoter, respectively, in the pFastBac™ dual vector plasmid, which was subsequently used to make recombinant Bacmid baculovirus DNAs (rAcNPV) using DH10Bac competent cells (Invitrogen, Carlsbad, Calif.). A recombinant baculovirus (rBV) expressing both M2e5x and M1 was generated by transfection of sf9 insect cells following the manufacturer's instruction. To produce influenza M2e5x VLPs containing M2e5x and M1 protein, a single dual rBV expressing both M2e5x and M1 protein was infected into sf9 insect cells at multiplication of infection of 2. For the production of M2e5x VLP vaccine using monomeric rBV expression system, insect cells were infected with one rBVs expressing M1 inner core protein and another rBVs expressing M2e5x surface proteins. At 2 days post-infection, the infected cell culture supernatants were clarified by centrifugation (6000 rpm, 30 min) and then were concentrated by the QuixStand™ hollow fiber based ultrafiltration system (GE Healthcare, Piscataway, N.J.). M2e5x VLPs were purified by sucrose gradient ultracentrifugation with layers of 20% and 60% (wt/vol) as previously described (Song J M, et al. (2011). PLoS One 6: e14538). Influenza A virus M2 monoclonal antibody 14C2 (Abcam Inc., Cambridge, Mass.) was used for detection of M2e5x protein by western blot.

Results

Comparison of M2e Protein Between Dual M2e5x VLP and M2e5x VLP

Figure 17C:
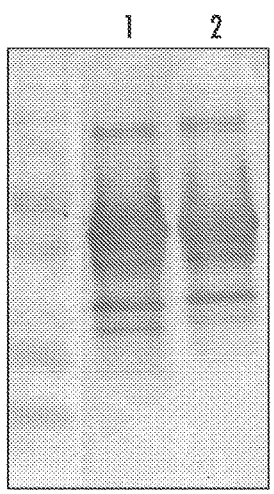
FIG. 17C is a Western blot for M2e5x protein using the monomeric vectors (lane 2) and the dual expression vector (lane 1).

It can be challenging to make a good quality VLP with combination of M2e5x baculovirus and M1 baculovirus. A dual M2e5x baculovirus was therefore designed to avoid the combination of each baculoviruses and the designed dual M2e5x and M1 baculovirus was used to infect sf9 cell with 2 moi. In western blot result, M2e reactivity to M2e monoclonal antibody (14C2) was about 2 times higher in dual M2e5x VLP than in M2e5x VLP (FIG. 17C).

Figure 18A:
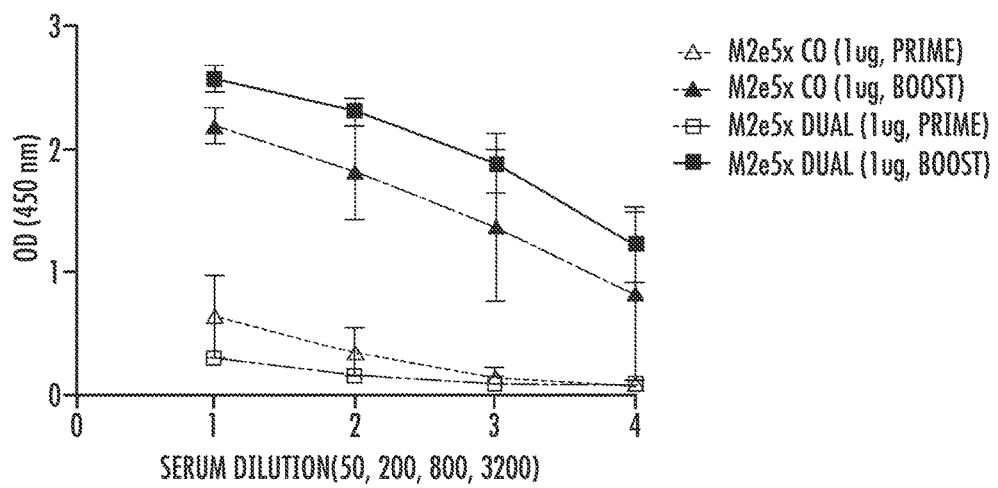
FIGS. 18A and 18B are graphs showing M2e antibody concentration (OD 450 nm) as function of serum dilution (50, 200, 800, 3200) after induction with M2e5x dual expression vector (squares) or M2e5x monomeric vectors (triangles).
Figure 18B:
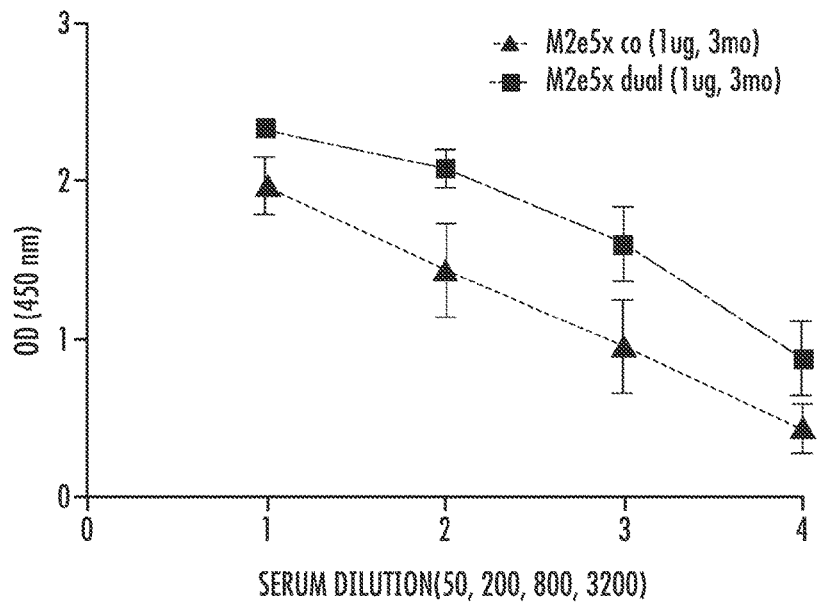

Comparison of Immunogenicity Between Dual Vector-Expressed M2e5x VLP and 2 Monomeric Vector-Expressed M2e5x VLP To compare immunogenicity of dual vector-expressed M2e5x VLP and 2 monomeric vectors co-infection expressed M2e5x VLP, mice were vaccinated with 1 µg of each VLPs by intramuscular route. Blood was taken at 3 weeks after each prime and boost vaccination to check antibody response and antibody level was checked 3 months after boost vaccination (FIG. 18). Optical density (OD) value of sera in mice that were vaccinated with dual vector-expressed M2e5x VLP showed 4 times higher than that of sera in mice that were vaccinated with M2e5x VLP by co-infecting 2 monomeric vectors of M1 and M2e5x. These results showed that dual M2e5x VLP from pFastBac dual vector was more immunogenic to produce M2e antibody than M2e5x VLP from co-infection with monomeric expression pFastBac vectors. Therefore, it is likely that the quality of dual M2e5x VLP is better than that of M2e5x VLP to produce M2e antibody by 4 folds.

Example 18: Preparation of Recombinant M2e4x-PR8HA Influenza Virus

Materials and Methods
Design of M2e4x-HA Gene

Figure 19:
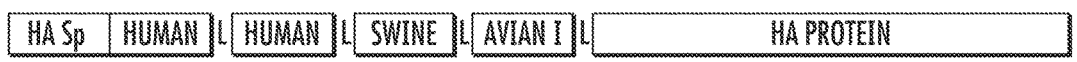
FIG. 19 is a schematic of a recombinant M2e4x-PR8HA construct.

A gene fragment encoding for four tandem repeats of M2 ectodomain (M2e5x) fused to the A/PR8 HA protein was chemically synthesized (GenScript, Piscataway, N.J.) and used in this study. The M2e4x protein domain was located between HA signal peptide (MKANLLVLLCALAAADA; SEQ ID NO:28) and HA0 domain (FIG. 19).

Cells, Viruses and Reagents

Figure 20:
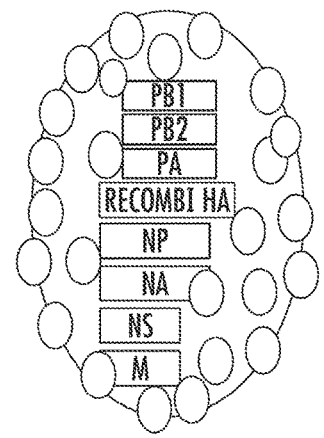
FIG. 20 is a schematic diagram of a recombinant M2e4x-PR8HA influenza virus.

Ten-day-old embryonated chicken eggs were used for virus propagation. A reassortant virus, termed rgM2e4x-PR8 virus, contains synthesized M2e4x-PR8 hemagglutinin and neuraminidase and 6 internal proteins from A/PR/8/34 (H1N1) virus (FIG. 20). Eight gene segments of influenza virus were transfected into 293T cell and infected 293T cells were incubated for 2 days at 5% CO$_2$ incubator. The supernatant was inoculated into ten-day-old embryonated chicken eggs and the inoculated eggs were incubated at 37° C. for 4 days. Allantoic fluid was harvested and hemagglutination (HA) assay was done to identify generation of recombinant influenza virus, M2e4x-PR8 influenza virus.

Results

M2e Reactivity to Inactivated M2e4x-PR8HA Influenza Virus

Figure 21:
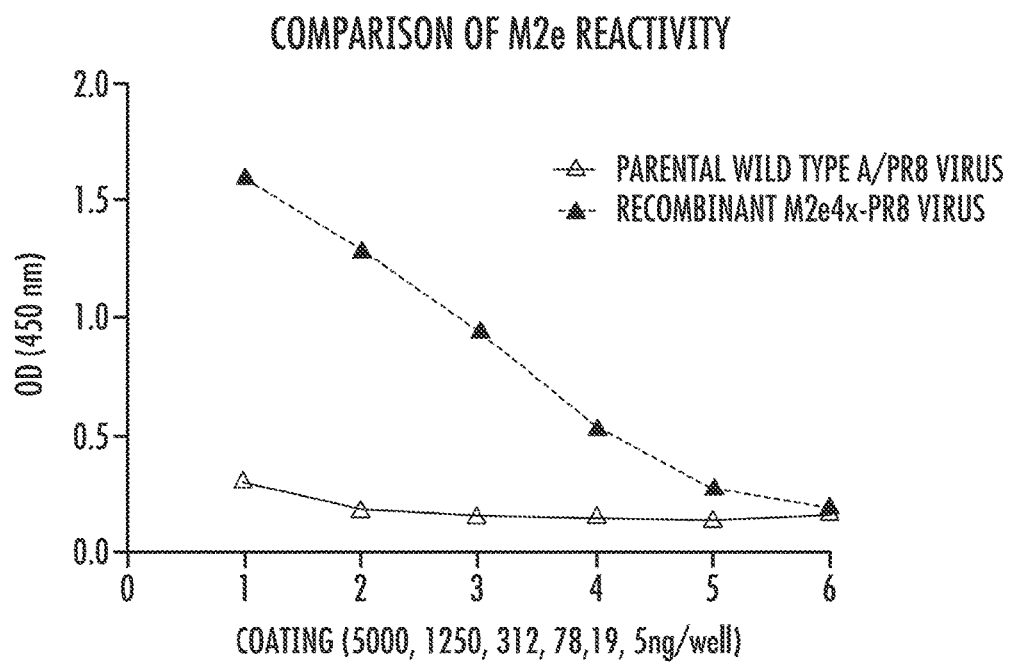
FIG. 21 is a graph showing M2e antibody reactivity to A/PR8 (open diamond) and recombinant M2e4x-PR8 virus (solid diamond).

Usually, the M2e protein (extracellular domain of M2) is associated with actively replicating virus which is exuberantly synthesized in infected cells but is not incorporated into the infectious viral particle at high levels. Therefore M2 protein was not easily detected with M2 monoclonal antibody (14C2) although M2 protein was exposed on the surface. Here, M2e reactivity was compared between M2e4x-PR8HA virus and A/PR/8 virus (FIG. 21). Inactivated M2e4x-PR8HA or A/PR8 influenza viruses were serially coated in ELISA immuno-plate from 5000 ng to 5 ng/100 μl/well. M2e reactivity was not detected to parental wild type A/PR8 virus up to 1250 ng/100 μl/well concentration and showed a positive value at the highest concentration of 5000 ng/100 μl/well. However M2e reactivity was significantly detected in recombinant M2e4x-PR8HA virus even at the low concentration of 20 ng/100 μl/well, which is almost 250 fold higher than that of the parental wild type A/PR8 virus (FIG. 21). Therefore, the approach of generating M2e4x-PR8HA virus can provide a new universal vaccine candidate targeting to M2e protein for influenza universal vaccine.

Example 19: M2e4x-PR8HA Influenza Virus Induces M2e Specific Antibody Responses

Figure 22A:
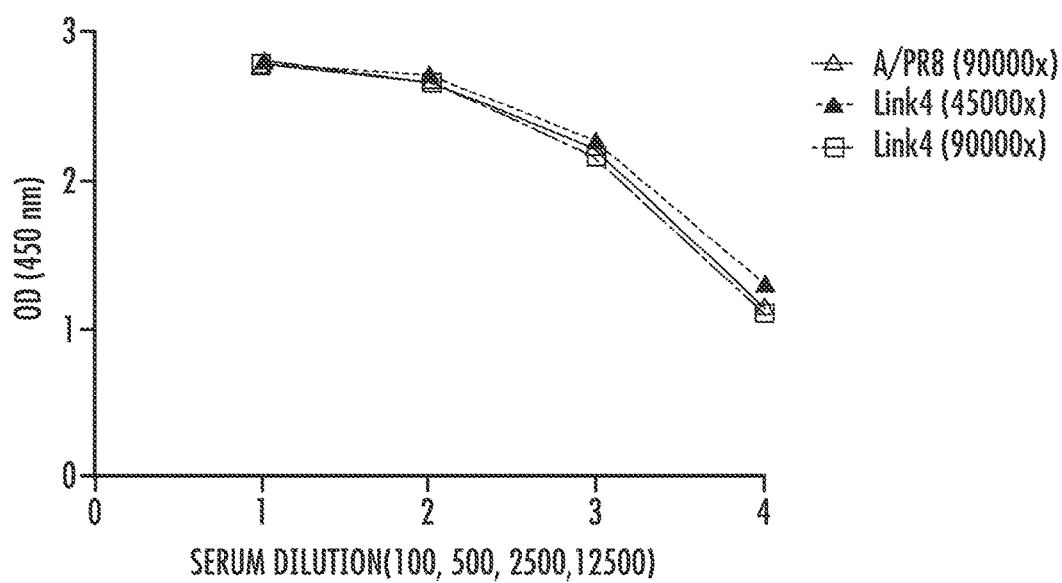
FIG. 22A is a graph showing antibody response for A/PR8 (90000×, open diamond) or Link 4 (45000, solid diamond; 90000, open square).
Figure 22B:
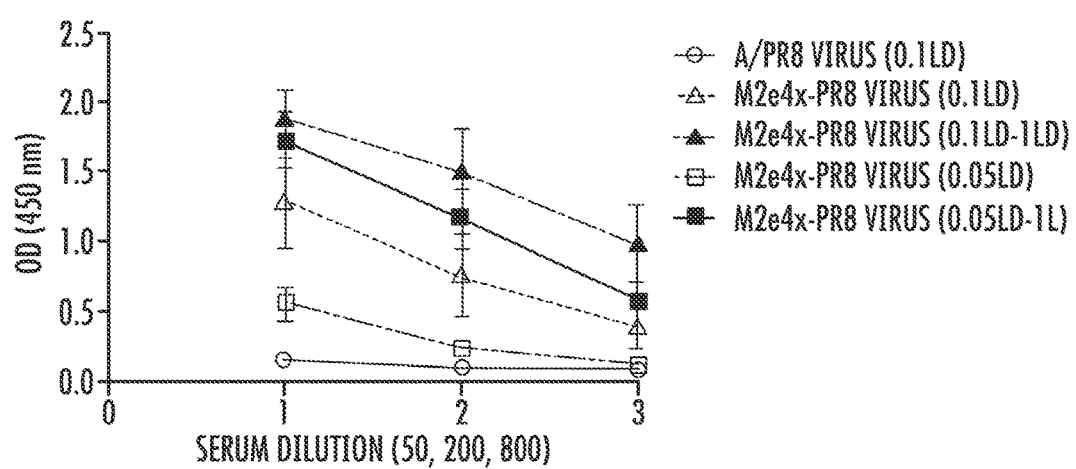
FIG. 22B is a graph showing antibody response specific to M2e for A/PR8 virus (open circle) or M2e4x-PR8 virus at 0.1LD (open triangle), 01.LD-1LD (solid triangle), 0.05LD (open square), or 0.05LD-1LD (solid square).

Materials and Methods
Immunization
For animal experiments, 6-8 week old female BALB/c mice (Harlan Laboratories, Indianapolis, Ind.) were intranasally immunized with 0.1 or 0.2LD of live M2e4x-PR8HA virus or 0.1LD of live A/PR8 virus at a 4-week interval. At 3 weeks after prime or boost immunization, mice were bled to test immune responses to M2e.
Determination of Antibody Responses
M2e specific serum antibody responses were determined by ELISA using inactivated purified A/PR8 virions or synthetic human type M2e peptides (2 μg/ml) as a coating antigen as previously described (Song J M, et al. (2011). *PLoS One* 6: e14538). Briefly, HRP-conjugated goat anti-mouse IgG was used as secondary antibodies to determine total IgG antibodies. The substrate TMB (Sigma-Aldrich, St. Louis, Mo.) was used to develop color and 1M $H_3PO_4$ was used to stop developing color reaction. The optical density at 450 nm was read using an ELISA reader.
Results
Mice were intranasally immunized with recombinant M2e4x-PR8HA virus or wild type A/PR8 virus, and then collected immune sera were used to determine antibody levels by using human M2e peptide or virus as an ELISA coating antigen (FIG. 22). Immune sera collected from both mice groups showed substantial levels of antibody reactivity to A/PR8 virus (FIG. 22A). However the reactivity to the human type M2e peptide was only observed in sera immunized with M2e4x-PR8HA influenza virus. Antibody response was dependent upon immunization dose of live M2e4x-PR8HA influenza virus. Therefore production of M2e antibody was due to M2e4x protein fused to HA protein in M2e4x-PR8 HA virus, implicating positional effects on immunogenicity.

DISCUSSION

The above studies involved the use of an influenza M2e5x VLP that contains tandem repeats of M2e comprising heterologous M2e sequences in a membrane-anchored form. There are few amino acid changes in residues 10-23 of M2e, depending on host species where influenza viruses are isolated (Liu W, et al. (2005). *Microbes Infect* 7: 171-177; Fiers W, et al. (2004). *Virus Res* 103: 173-176). Thus, an additional strategy was introduced into the M2e5x construct to enhance the breadth of cross protection by including M2e sequences originated from influenza A viruses of swine and avian species. A heterologous tandem repeat of M2e on VLPs is capable of broadening and extending cross reactivity after vaccination. Immune sera to M2e5x VLP vaccination were cross-reactive to M2e peptide sequences of swine and avian origins in addition to the human type. The disclosed M2e5x construct with an HA-derived transmembrane domain was found to be incorporated into VLPs at a much higher level compared to the whole influenza virus particles. The disclosed M2e5x VLP construct significantly improved the immunogenicity and efficacy compared to M2WT VLP. Therefore, molecular engineering of an M2e vaccine construct and presenting it on VLPs is useful for presenting viral vaccine antigens and developing an effective vaccine.

Intramuscular administration is the common route of influenza vaccination in humans. However, it is difficult to induce heterosubtypic cross protection by intramuscular immunization with non-replicating subunit vaccines. Heterosubtypic protection was observed with inactivated influenza virus vaccines in the presence of endotoxin mucosal adjuvants via intranasal immunization but not via intramuscular immunization (Takada A, et al. (2003). *Vaccine* 21: 3212-3218; Tumpey T M, et al. (2001). *J Virol* 75: 5141-5150). Intranasal immunization with non-replicating or inactivated subunit vaccines has not been approved for human use yet and its efficacy in humans remains unknown. In clinical studies, some side effects were reported to be associated with intranasal influenza vaccination with an inactivated virosomal vaccine (Sendi P, et al. (2004). *Am J Med* 116: 856-858; El Bakkouri K, et al. (2011). *J Immunol* 186: 1022-1031). Thus, it is highly significant to demonstrate heterosubtypic cross protection after intramuscular immunization with molecularly designed M2e5x VLP vaccines.

The disclosed vaccine containing tandem repeats of M2e on VLPs presented in a membrane-anchored form, mimicks its native-like conformation since M2 is a membrane protein. The M2e5x VLPs were highly immunogenic and able to induce broad cross-protection in the absence of adjuvants. This is in contrast to previous studies reporting chemical or genetic fusion of M2e to carrier vaccines with multiple immunizations at high doses of M2e vaccines in the presence of potent adjuvants inappropriate for human use. In particular, immune sera to M2e5x VLP vaccination showed cross-reactivity to different strains of influenza virus particles. Protection was observed in the A/Philippines/2/82 H3N2 virus challenge with less body weight loss (approximately 5%), which might be due to the high reactivity of M2e5x VLP immune sera to that virus. Antibodies induced by M2e conjugate vaccines such as M2e-HBVc were not able to bind to virus particles despite high titers to M2e peptide antigens, which explains weak protection by M2e-HBVc immunization (Jegerlehner A, et al. (2004). *J Immunol* 172: 5598-5605). It is speculated that cross-reactivity to virus is likely to be one mechanism for providing protection. Importantly, long-term protection even after 8 months post vaccination was observed without significant morbidity (FIG. 7C, 7D).

Protective immune correlates have not been well understood after influenza M2 vaccination. Serum antibodies specific to M2e were shown to play an important role in providing protection as evidenced by effects of M2e5x VLP immune sera on conferring protection in naive mice (FIGS. 8A-8D). Fc receptor was shown to be an important immune mediator for conferring protection by M2 immune sera as shown using a Fc receptor knockout mouse model. Nonetheless, there is a high possibility that mucosal immune responses and INF-γ secreting T cell responses induced by intramuscular immunization with M2e5x VLPs contributed to improving the protection against viral challenge infection.

Significant levels of BALF IgG antibodies were observed in the group of M2e5x VLP immunization even prior to challenge but not IgA antibody levels (FIG. 5A, 5B). In particular, BALF IgA antibodies were rapidly increased to high levels at an early time point day 5 post-challenge. Thus, these results suggest that intramuscular vaccination with an immunogenic vaccine such as M2e5x VLPs can prime mucosal immunity, which was shown to induce rapid recall mucosal immunity upon exposure to a pathogen. It is also interesting to note that high levels of spleen and particularly lung cells secreting IFN-γ were rapidly induced at day 5 post challenge (FIGS. 6A-6D). Therefore, in addition to serum antibodies specific to M2e, it is likely that multiple systemic and mucosal immune parameters contribute to cross protection after M2e5x VLP intramuscular immunization.

In summary, this study demonstrates several important advancements in the field of developing universal influenza vaccines. Heterologous tandem repeats of M2e epitope sequences (M2e5x) genetically designed to be expressed in a membrane-anchored form were effectively incorporated into VLPs at a much higher level than that on influenza virions or M2WT VLPs. Intramuscular immunization with M2e5x VLP vaccines was proved to be effective in inducing cross protection regardless of HA subtypes. Immune sera to M2e5x VLP vaccination were highly reactive to influenza virions and sufficient to transfer cross protection to naïve mice. This protection was achieved in the absence of adjuvant. Intramuscular immunization with M2e5x VLP vaccines was able to elicit antibodies in mucosal sites and IFN-γ secreting cellular immune responses upon viral challenge. This cross protection was found to be long-lived without significant signs of disease. Thus, genetically designed M2e5x VLP vaccines could be more effective in inducing M2e immune responses than live virus infection.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A cross-protective influenza vaccine comprising a fusion protein immobilized on the surface of a virus-like particle (VLP) or in a secreted form, wherein the fusion protein comprises three or more heterologous influenza virus matrix protein 2 extracellular (M2e) domains, wherein the fusion protein comprises one or more M2e domains from a human influenza A subtype, one or more M2e domains from a swine influenza A subtype, and one or more M2e domains from an avian influenza A subtype, and wherein the vaccine is cross-protective against two or more subtypes of influenza A without the use of an adjuvant.

2. The vaccine of claim 1, wherein the human M2e domain comprises the amino acid sequence SEQ ID NO:1 or an amino acid sequence having at least 90% sequence identity to SEQ ID NO:1.

3. The vaccine of claim 1, wherein the swine M2e domain comprises the amino acid sequence SEQ ID NO:2 or an amino acid sequence having at least 90% sequence identity to SEQ ID NO:2.

4. The vaccine of claim 1, wherein the avian M2e domains are from H5, H7, or H9 influenza A subtypes.

5. The vaccine of claim 1, wherein the avian M2e domain comprises the amino acid sequence SEQ ID NO:3 or SEQ ID NO:4 or an amino acid sequence having at least 90% sequence identity to SEQ ID NO:3 or SEQ ID NO:4.

6. The vaccine of claim 1, wherein at least one M2e domain comprises an avian M2e domain comprising the amino acid sequence SEQ ID NO:3 or an amino acid sequence having at least 90% sequence identity to SEQ ID NO:3, and wherein at least one M2e domain comprises an avian M2e domain comprising the amino acid sequence SEQ ID NO:4 or an amino acid sequence having at least 90% sequence identity to SEQ ID NO:4.

7. The vaccine of claim 1, wherein the fusion protein further comprises a signal peptide at the N-terminus.

8. The vaccine of claim 7, wherein the signal peptide comprises mellitin signal peptide.

9. The vaccine of claim 8, wherein the signal peptide comprises the amino acid sequence SEQ ID NO:12 or an amino acid sequence having at least 90% sequence identity to SEQ ID NO:12.

10. The vaccine of claim 1, wherein the fusion protein further comprises an oligomer stabilization domain.

11. The vaccine of claim 10, wherein the oligomer stabilization domain comprises a leucine zipper tetramerization motif.

12. The vaccine of claim 11, wherein the oligomer stabilization domain comprises GCN4.

13. The vaccine of claim 12, wherein the oligomer stabilization domain comprises the amino acid sequence SEQ ID NO:13 or a an amino acid sequence having at least 90% sequence identity to SEQ ID NO:13.

14. The vaccine of claim 1, wherein the fusion protein further comprises a membrane anchor.

15. The vaccine of claim 14, wherein the membrane anchor is a transmembrane domain and optionally a cytoplasmic domain of a viral envelope protein.

16. The vaccine of claim 15, wherein viral envelope protein is an influenza A hemagglutinin (HA).

17. The vaccine of claim 15, wherein the transmembrane domain comprises the amino acid sequence SEQ ID NO:14 or SEQ ID NO:15 or an amino acid sequence having at least 90% sequence identity to SEQ ID NO:14 or SEQ ID NO:15.

18. The vaccine of claim 1, wherein the fusion protein comprises at least five heterologous M2e domains.

19. The vaccine of claim 18, wherein the fusion protein comprises at least ten heterologous M2e domains.

20. The vaccine of claim 1, wherein the fusion protein comprises an amino acid sequence having a formula selected from the group consisting of:

$$X_1\text{-}([hM2e]_n\text{-}[sM2e]_n\text{-}[aM2e]_n)_n\text{-}X_2\text{-}X_3,$$

$$X_1\text{-}([hM2e]_n\text{-}[aM2e]_n\text{-}[sM2e]_n)_n\text{-}X_2\text{-}X_3,$$

$$X_1\text{-}([sM2e]_n\text{-}[hM2e]_n\text{-}[aM2e]_n)_n\text{-}X_2\text{-}X_3,$$

$$X_1\text{-}([sM2e]_n\text{-}[aM2e]_n\text{-}[hM2e]_n)_n\text{-}X_2\text{-}X_3,$$

$$X_1\text{-}([aM2e]_n\text{-}[sM2e]_n\text{-}[hM2e]_n)_n\text{-}X_2\text{-}X_3, \text{ and}$$

$$X_1\text{-}([aM2e]_n\text{-}[hM2e]_n\text{-}[sM2e]_n)_n\text{-}X_2\text{-}X_3,$$

wherein "$X_1$" consists of nothing or a signal peptide,
wherein "hM2e" consists of a human M2e domain,
wherein "sM2e" consists of a swine M2e domain,
wherein "sM2e" consists of an avian M2e domain,
wherein "$X_2$" consists of nothing or an oligomer stabilization domain,
wherein "$X_3$" consists of nothing or a membrane anchor domain,
wherein each "n" is independently an integer from one to five, and
wherein "-" consists of a peptide linker or a peptide bond.

21. The vaccine of claim 20, wherein the fusion protein comprises an amino acid sequence having the following formula: $X_1\text{-}(hM2e\text{-}hM2e\text{-}sM2e\text{-}sM2e\text{-}aM2e)_n\text{-}X_2\text{-}X_3$.

22. The vaccine of claim 20, wherein the signal peptide comprises melittin.

23. The vaccine of claim 20, wherein the oligomer stabilization domain comprises GCN4.

24. The vaccine of claim 20, wherein the membrane anchor domain comprises the transmembrane-cytoplasmic domain from an influenza A hemaglutinin.

25. The vaccine of claim 21, wherein "n" is 2.

26. The vaccine of claim 1, wherein the fusion protein comprises the amino acid sequence SEQ ID NO:16, or an amino acid sequence having at least 90% sequence identity to SEQ ID NO:16.

27. The vaccine of claim 1, wherein the VLP comprises matrix protein 1 (M1).

28. The vaccine of claim 27, wherein the vaccine is produced by coinfecting insect cells with one or more recombinant baculoviruses expressing the M1 proteins and the fusion proteins, culturing the insect cells under physiological conditions, and purifying the VLPs from insect cell culture supernatants.

29. The vaccine of claim 27, wherein influenza virus hemagglutinin (HA) and neuraminidase (NA) are not immobilized on the surface of the VLP.

30. The vaccine of claim 1, further comprising an influenza virus-like particle (VLP) vaccine, a whole inactivated virus, split viral vaccine, or live attenuated influenza vaccine.

31. The vaccine of claim 1, formulated for delivery via intranasal, intramuscular, subcutaneous, transdermal or sublingual administration.

32. The vaccine of claim 1, further comprising an adjuvant.

33. The vaccine of claim 32, wherein the adjuvant is selected from the group consisting of ASO4 (alum plus monophosphoryl lipid A), bacterial cell wall components, MF59 (mineral oil based adjuvant), and a molecular adjuvant incorporated VLP in a membrane-anchored form.

34. The vaccine adjuvant of claim 33, wherein the molecular adjuvant is GM-CSF (granulocyte macrophage colony stimulating factor) or bacterial flagellin.

35. A method of vaccinating a subject for influenza A comprising administering the cross-protective influenza vaccine of claim 1 to a subject in need thereof by intranasal, intramuscular, subcutaneous, transdermal, or sublingual administration.

36. The method of claim 35, further comprising administering to the subject a composition comprising an influenza virus-like particle (VLP) vaccine, a whole inactivated virus, split viral vaccine, or live attenuated influenza vaccine.

37. The method of claim 36, wherein the cross-protective influenza vaccine and the influenza virus-like particle (VLP) vaccine, the whole inactivated virus, the split viral vaccine, or the live attenuated influenza vaccine are in the same composition.

38. The method of claim 36, wherein the composition comprising influenza virus-like particle (VLP) vaccine, a whole inactivated virus, split viral vaccine, or live attenuated influenza vaccine is administered before or after the cross-protective influenza vaccine.

39. The method of claim 36, wherein the cross-protective influenza vaccine is administered prior to influenza seasonal vaccination or after influenza seasonal vaccination.

40. The method of claim 39, wherein the period between cross-protective influenza vaccine and seasonal vaccination administration is one day to 10 years.

* * * * *

UNITED STATES PATENT AND TRADEMARK OFFICE
CERTIFICATE OF CORRECTION

PATENT NO. : 9,889,189 B2
APPLICATION NO. : 14/440114
DATED : February 13, 2018
INVENTOR(S) : Kang et al.

It is certified that error appears in the above-identified patent and that said Letters Patent is hereby corrected as shown below:

In the Specification

Statement Regarding Federally Sponsored Research & Development:

Column 1, Lines 17-18: "This invention was made with Government Support under Grant No. AI093772 and Grant No. A1087782 awarded to ..." should read "This invention was made with Government Support under under Grant No. AI093772 and Grant No. AI087782 awarded to ..."

Signed and Sealed this
Twenty-first Day of June, 2022

Katherine Kelly Vidal
*Director of the United States Patent and Trademark Office*